(12) United States Patent
Mochly-Rosen et al.

(10) Patent No.: US 9,102,651 B2
(45) Date of Patent: *Aug. 11, 2015

(54) MITOCHONDRIAL ALDEHYDE DEHYDROGENASE-2 MODULATORS AND METHODS OF USE THEREOF

(75) Inventors: Daria Mochly-Rosen, Menlo Park, CA (US); Che-Hong Chen, Fremont, CA (US); Xiaohu Ouyang, Fremont, CA (US)

(73) Assignee: The Board of Trustees-Leland Stanford Junior University, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/214,937

(22) Filed: Aug. 22, 2011

(65) Prior Publication Data

US 2012/0010248 A1    Jan. 12, 2012

Related U.S. Application Data

(63) Continuation of application No. 12/044,870, filed on Mar. 7, 2008, now abandoned.

(60) Provisional application No. 60/905,963, filed on Mar. 8, 2007.

(51) Int. Cl.

| C07D 317/44 | (2006.01) |
|---|---|
| A01N 43/30 | (2006.01) |
| A61K 31/36 | (2006.01) |
| C07D 405/00 | (2006.01) |
| C07D 317/58 | (2006.01) |
| C07D 405/12 | (2006.01) |

(52) U.S. Cl.
CPC ............ *C07D 317/58* (2013.01); *C07D 405/12* (2013.01)

(58) Field of Classification Search
None
See application file for complete search history.

(56) References Cited

U.S. PATENT DOCUMENTS

| 2,319,808 A | 5/1943 | Fernholz et al. |
| 4,861,891 A | 8/1989 | Saccomano et al. |
| 5,260,323 A | 11/1993 | Baader et al. |

(Continued)

FOREIGN PATENT DOCUMENTS

| CN | 1749415 A | 3/2006 |
| EP | 1 402 887 | 3/2004 |

(Continued)

OTHER PUBLICATIONS

Borgna et al. Preparation and study of the phytotoxic activity of N-arylalkyl substituted amines. (Farmaco, Edizione Scientifica, vol. 32, No. 11, pp. 813-826, 1977). Translation attached.*

(Continued)

*Primary Examiner* — Anna Pagonakis
(74) *Attorney, Agent, or Firm* — Rudy J. Ng; Paula A. Borden; Bozicevic, Field & Francis LLP

(57) ABSTRACT

The present invention provides compounds that function as modulators of mitochondrial aldehyde dehydrogenase-2 (ALDH2) activity; and pharmaceutical compositions comprising the compounds. The present invention provides therapeutic methods involving administering a subject compound, or a subject pharmaceutical composition. The present invention further provides assays for identifying agonists of ALDH2.

3 Claims, 12 Drawing Sheets

```
  1 mlraaarfgp rlgrrllsaa atqavpapnq qpevfcnqif innewhdavs rktfptvnps
 61 tgevicqvae gdkedvdkav kaaraafqlg spwrrmdash rgrllnrlad lierdrtyla
121 aletldngkp yvisylvdld mvlkclryya gwadkyhgkt ipidgdffsy trhepvgvcg
181 qiipwnfpll mqawklgpal atgnvvvmkv aeqtpltaly vanlikeagf ppgvvnivpg
241 fgptagaaia shedvdkvaf tgsteigrvi qvaagssnlk rvtlelggks pniimsdadm
301 dwaveqahfa lffnqgqccc agsrtfvqed iydefversv araksrvvgn pfdskteqgp
361 qvdetqfkki lgyintgkqe gakllcgggi aadrgyfiqp tvfgdvqdgm tiakeeifgp
421 vmqilkfkti eevvgranns tyglaaavft kdldkanyls qalqagtvwv ncydvfgaqs
481 pfggykmsgs grelgeyglq aytevktvtv kvpqkns (SEQ ID NO:1)
```

```
  1 mlraaarfgp rlgrrllsaa atqavpapnq qpevfcnqif innewhdavs rktfptvnps
 61 tgevicqvae gdkedvdkav kaaraafqlg spwrrmdash rgrllnrlad lierdrtyla
121 aletldngkp yvisylvdld mvlkclryya gwadkyhgkt ipidgdffsy trhepvgvcg
181 qiipwnfpll mqawklgpal atgnvvvmkv aeqtpltaly vanlikeagf ppgvvnivpg
241 fgptagaaia shedvdkvaf tgsteigrvi qvaagssnlk rvtlelggks pniimsdadm
301 dwaveqahfa lffnqgqccc agsrtfvqed iydefversv araksrvvgn pfdskteqgp
361 qvdetqfkki lgyintgkqe gakllcgggi aadrgyfiqp tvfgdvqdgm tiakeeifgp
421 vmqilkfkti eevvgranns tyglaaavft kdldkanyls qalqagtvwv ncydvfgaqs
481 pfggykmsgs grelgeyglq aytkvktvtv kvpqkns (SEQ ID NO:2)
```

(56) References Cited

U.S. PATENT DOCUMENTS

| | | | |
|---|---|---|---|
| 5,360,806 A | | 11/1994 | Toki et al. |
| 5,374,605 A | * | 12/1994 | Hallenbach et al. ........... 504/252 |
| 5,409,907 A | * | 4/1995 | Blase et al. ...................... 514/54 |
| 6,762,176 B1 | | 7/2004 | Lassauniere et al. |
| 6,780,883 B2 | | 8/2004 | Booth et al. |
| 6,900,338 B1 | | 5/2005 | Haj-Yehia |
| 6,939,882 B1 | | 9/2005 | Cooke et al. |
| 8,354,435 B2 | * | 1/2013 | Chen et al. ...................... 514/338 |
| 8,389,522 B2 | * | 3/2013 | Mochly-Rosen et al. .... 514/248 |
| 2002/0034783 A1 | | 3/2002 | Meyers et al. |
| 2002/0156281 A1 | | 10/2002 | Booth et al. |
| 2003/0100034 A1 | | 5/2003 | Hunter |
| 2004/0234622 A1 | | 11/2004 | Muto et al. |
| 2005/0171043 A1 | | 8/2005 | Mochly-Rosen et al. |
| 2005/0215548 A1 | | 9/2005 | Wang |
| 2005/0215645 A1 | | 9/2005 | Muto et al. |
| 2006/0106051 A1 | | 5/2006 | Dyckman et al. |
| 2006/0173050 A1 | | 8/2006 | Liu et al. |
| 2008/0153926 A1 | | 6/2008 | Mochly-Rosen et al. |
| 2008/0200461 A1 | | 8/2008 | Anderson et al. |
| 2009/0082431 A1 | | 3/2009 | Mochly-Rosen et al. |
| 2009/0163545 A1 | | 6/2009 | Goldfarb |
| 2010/0113423 A1 | | 5/2010 | Mochly-Rosen et al. |
| 2011/0105602 A2 | | 5/2011 | Mochly-Rosen et al. |
| 2013/0253010 A1 | * | 9/2013 | Chen et al. ...................... 514/338 |
| 2013/0267501 A1 | * | 10/2013 | Mochly-Rosen et al. ........................ 514/217.03 |

FOREIGN PATENT DOCUMENTS

| | | |
|---|---|---|
| EP | 1 402 888 | 3/2004 |
| EP | 2018863 | 1/2009 |
| JP | 1-203351 | 8/1989 |
| JP | 2-115168 | 4/1990 |
| JP | 6-321903 | 11/1994 |
| JP | 08208615 | 8/1996 |
| JP | 2009544742 A | 12/2009 |
| WO | WO 99/54284 * | 10/1998 |
| WO | WO99/23063 | 5/1999 |
| WO | 99-32444 A1 | 7/1999 |
| WO | 99-54284 A1 | 10/1999 |
| WO | WO 01/12604 | 2/2001 |
| WO | WO-01-32928 | 5/2001 |
| WO | WO02/22599 | 3/2002 |
| WO | WO02/053544 | 7/2002 |
| WO | WO 02/064568 | 8/2002 |
| WO | WO03/007931 | 1/2003 |
| WO | 03-030937 A1 | 4/2003 |
| WO | WO03/064391 | 8/2003 |
| WO | WO03/086377 | 10/2003 |
| WO | WO2004/022523 | 3/2004 |
| WO | WO2005/014550 | 2/2005 |
| WO | WO2005/037782 A2 | 4/2005 |
| WO | WO2005/037792 A1 | 4/2005 |
| WO | 2005057213 | 6/2005 |
| WO | WO2005/007889 | 8/2005 |
| WO | 2005084392 | 9/2005 |
| WO | 2005-110422 A1 | 11/2005 |
| WO | WO2007/034312 A2 | 3/2007 |
| WO | WO2007/110237 | 10/2007 |
| WO | 2008-002725 A1 | 1/2008 |
| WO | WO2008/014497 A2 | 1/2008 |
| WO | 2008-024497 A2 | 2/2008 |
| WO | WO2008/021388 A1 | 2/2008 |
| WO | WO 2008/071397 | 6/2008 |
| WO | WO 2008/082487 | 7/2008 |
| WO | WO2009/146555 | 12/2009 |
| WO | WO2009/156484 | 12/2009 |

OTHER PUBLICATIONS

Williams et al. Foye's Principles of Medicinal Chemistry. 5th edition. pp. 50 and 59-61, 2002.*
Williams et al. (Foye's Principles of Medicinal Chemistry, 5th edition, pp. 50 and 59-61). 2002.*
Borgna, et al., "Preparation and Study of the Phytotoxic Activity of N-arylalkyl Substituted Amides", Farmaco, Edizione Scientifica, 1977, vol. 32, No. 11, pp. 813-826.
Larson, et al., "Distruption of the Coenzyme Binding Site and Dimer Interface Revealed in the Crystal Structure of Mitochondrial Aldehyde Dehydrogenase "Asian" Variant", The Journal of Biological Chemistry, 2005, vol. 280, No. 34, pp. 30550-30556.
Li, et al., "Mitochondrial Aldehyde Dehydrogenase-2 (ALDH2) Glu504Lys Polymorphism Contributes to the Variation in Efficacy of Sublingual Nitroglycerin", The Journal of Clinical Investigation, 2006, vol. 116, No. 2, pp. 506-511.
Pantani, et al., "Bioisoterism: A Rational Approach to Drug Design", Chem. Rev., 1996, vol. 96, pp. 3146-3176.
Stella, et al. ,"Prodrug Strategies to Overcome Poor Water Solubility", Advanced Drug Deliver Reviews, 2007, vol. 59, pp. 677-694.
Registry (STN) [online], Apr. 24, 2001 (searched date: Apr. 25, 2013), CAS Registry No. 332129-81-4.
Registry (STN) [online], Jul. 29, 2001 (searched date: Apr. 25, 2013), CAS Registry No. 349438-38-6.
Registry (STN) [online], May 14, 2003 (searched date: Apr. 25, 2013), CAS Registry No. 514816-37-6.
Registry (STN) [online], Aug. 1, 2001 (searched date: Apr. 25, 2013), CAS Registry No. 349615-88-9.
Registry (STN) [online], Jan. 2, 2001 (searched date: Apr. 25, 2013), CAS Registry No. 312526-08-2.
Registry (STN) [online], Jul. 25, 2006 (searched date: Apr. 25, 2013), CAS Registry No. 895680-72-5.
Registry (STN) [online], Jul. 25, 2006 (searched date: Apr. 25, 2013), CAS Registry No. 895680-64-5.
Registry (STN) [online], Nov. 5, 2004 (searched date: Apr. 25, 2013), CAS Registry No. 775317-15-2.
Registry (STN) [online], Jun. 7, 2004 (searched date: Apr. 25, 2013), CAS Registry No. 690210-80-1.
Registry (STN) [online], Jul. 26, 2001 (searched date: Apr. 25, 2013), CAS Registry No. 348604-08-0.
Registry (STN) [online], Apr. 2, 2004 (searched date: Apr. 25, 2013), CAS Registry No. 670271-74-6.
Zhang, et al., "Automation of Fluorous Solid-Phase Extraction for Parallel Synthesis", J. Comb. Chem. (Nov.-Dec. 2006), 8(6):890-896.
Konoplitskaya, et al., "Influence of Cyclopropylethyl-Containing Amines and Amides of the Isoenzyme Forms of Rat Liver Aldehyde Dehydrogenase", 1994, vol. 28, No. 1, pp. 7-10.
Furata, et al., "Efficient Synthesis of Phenanthridinone Derivatives via a Palladium-Catalyzed Coupling Process", Org. Lett. (Jan. 2007), 9(2):183-6.
Grigg, et al., "Synthesis of Cyclopropanes by Intramolecular Attack of N-Nucleophiles on the Central Carbon of (π-Allyl)palladium Complexes", Eur. J. Org. Chem. (Feb. 2001), 4:707-712.
Satoh, et al., "Comparison of the inhibitory action of synthetic capsaicin analogues with various NADH-ubiquinone oxidoreductases", Biochimica et Biophysica Acta (Jan. 1996), 1273(1):21-30.
U.S. Appl. No. 13/747,106, filed Jan. 22, 2013, Mochly-Rosen, et al.
U.S. Appl. No. 13/717,056, filed Dec. 17, 2012, Mochly-Rosen, et al.
Himel, et al., "Fluorescent Analogs of Insecticides and Synergists. Synthesis and Reactions of Active-Site-Directed Fluorescent Probes", J. Agr. Food Chem., 1971, 19(6):1175-1180.
Moussa et al. CAS: 146: 337551, 2007.
Weintraub et al. CAS: 143: 405804, 2005.
Huigsen et al. CAS: 46: 45365, 1952.
Budas, et. al., "Activation of Aldehyde Dehydrogenase 2 (ALDH2) Confers Cardioprotection in Protein Kinase C Epsilon (PkCε) Knockout Mice", Journal of Molecular and Cellular Cardiology, 2009, vol. 48, pp. 757-764.
Bukhitiarova, et al., "Structure and Anti-inflammatory Activity of Isonicotinic and Nicotine Amides", Pharmaceutical Chemistry Journal, 1997, vol. 31, No. 11, pp. 597-598.
Bukhitiarova, et al., "Possibilities for search for New Analagesics in the series of Arylamides of Isoniotinic and Nocotine Acids", Dopovidi Natsional'Noi Akademii Nauk Ukraini, 1998, No. 8, pp. 162-164.
Chen, et al., CAS:149:548594, 2008.

(56) References Cited

OTHER PUBLICATIONS

Chen, et. al., "An Activator of Mutant and Wildtype Aldehyde Dehydrogenase Reduces Ischemic Damage to the Heart",Science, 2008, vol. 321, No. 5895, pp. 1493-1495.
Cutshall, et. al., "Nicotinamide N-Oxides as CXCR2 Antagonists", Bioorganic & Medicinal Chemistry Letters, 2001, vol. 11, pp. 1951-1954.
Davis, et. al., "Requirement for Pax6 in Corneal Morphogenesis: a Role in Adhesion", Journal of Cell Science, 2003, vol. 116, No. 11, pp. 2157-2167.
Deng, et al., "Distinct Expression Levels and patterns of Stem Cell Marker, Aldehyde Dehydrogenase Isoform 1 (ALDH1), in Human Epithelial Cancers", PLoS One, 2010, vol. 5, No. 4, pp. 1-11.
Feng, et al., "Isolation and Characterization of Human Salivary Glands for Stem Cell Transplantation to Reduce Radiation-Induced Hyposalivation", Radiotherapy and Oncology, 2009, vol. 92, pp. 466-471.
Fernholz, et. al., "Stigmastadienone-22, 23-dibromide and related compounds", 1943, Accession No. 1943: 40468.
Gilman et. al. "Organometallic Compounds in the Kolbe and Reimer-Tiemann Reactions", Journal of Organic Chemistry, 1945, Accession No. 1946:2074.
Hess, et al., "Functional Characterization of Highly Purified Human Hematopoietic Repopulating Cells Isolated According to Aldehyde Dehydrogenase Activity", Blood, 2004, vol. 104, No. 6, pp. 1648-1655.
Johnson, et al., "Metabolism, Excretion, and Pharmacokinetics of (3-{[4-Tert-Butylbenzy)-(Pyridine-3-sulfonyl)-Amino]-Methyl}-Phenoxy)-Acetic Acid, An Ep2recepto-Selective Prostaglandin E2 Agonist, in Male and Female Sprague-Dawley Rats", 2005, Drug Metabolism and Disposition, vol. 33, No. 8, pp. 1191-1201.
Katritzky, et al., "N-Oxides and Related Compounds. Part X. The Hydrogenation pd some Polyridine 1-oxides", 1958, J. Chem. Soc., pp. 1-18.
Lombaert, et al., "Rescue of Salivary Gland Function after Stem Cell Transplantation in Irradiated Glands", PLoS One, 2008, vol. 3, No. 4, pp. 1-13.
Nicoll-Griffith, "Stereoelectronic Model to Explain the Resolution of Enantiomeric Ibuprofen Amides on the Pirkle Chiral Stationary Phase", Journal of Chromatography,1987, vol. 402, pp. 179-187.
Nicoll-Griffith's CAS: 107: 141210, 1987.
Palacios, "Diuretic Action of New Sulfonamide Compounds", 1964, Arch. Inst. Farmacol. Exptl., vol. 16, No. 1, pp. 1-18.
Paruszewski, et al., "Anticonvulsant Activity of Benzylamides of Some Amino Acids and Heterocyclic Acids", Protein and Peptide and Peptide Letters, 2003, vol. 10, No. 5, pp. 475-482.
Perez-Miller, et al., "Alda-1 is an Agonist and Chemical Chaperone for the Common Human Aldehyde Dehydrogenase 2 Variant", Nat Struct Mol Biol, 2010, vol. 17, No. 2, pp. 159-164.
Sato, et. al., "2-Hydroxymethylnicotinic Acid Lactone, 2-Hydroxymethylpyridine-3-acetic Acid Lactone, and Some of their Derivatives", Chem. Pharm. Bull., 1960, vol. 8, No. 5, pp. 427-435.
Seto, et. al., "Design and Synthesis of Novel 9-substituted -7-aryl-3,4,5,6-tetrahydro-2H-pyrido [4,3-b]-and [2,3-b]-1,5-oxazocin-6-ones as NK1 Antagonists", 2005, Bioorganic & Medicinal Chemistry Letters, vol. 15, pp. 1479-1484.
Stella et. al., "Prodrug Strategies to Overcome Poor Water Solubility", Advanced Drug Delivery Reviews, 2007, vol. 59, pp. 677-694.
STN:11/16, 1984, RN 7500-45-0.
Tracey et al. "Product class 4: N-Arylalkanamides, ynamides, enamides, dienamides and allenamides", Science of Synthesis, 2005, Accession No. 2006:359121.
Registry (STN) [online], Jun. 5, 2001(searched date:Dec. 19, 2013), CAS Registry No. 339335-56-7.
Messiha and Hughes "Liver Alcohol and Aldehyde Dehydrogenase Inhibition and Potentiation by histamine Agonists and Antagonists," Clinical and Experimental Pharmacology and physiology 6(3) 281-292 (1979).

* cited by examiner

```
  1 mlraaarfgp rlgrrllsaa atqavpapnq qpevfcnqif innewhdavs rktfiptvnps
 61 tgevicqvae gdkedvdkav kaaraafqlg spwrrmdash rgrilnriad lierdrtyla
121 aletldngkp yvisylvdid mvlkciryya gwadkyhgkt ipidgdffsy trhepvgvcg
181 qiipwnfpll mqawklgpal atgnvvvmkv aeqtpltaly vanlikeagf ppgvvnivpg
241 fgptagaaia shedvdkvaf tgsteigrvi qvaagssnik rvtieiggks pniimsdadm
301 dwaveqahfa lffnggqccc agsrtfvqed iydefversv araksrvvgn pfdskteqgp
361 qvdetqfkki lgyintgkqe gakilcgggi aadrgyfiqp tvfgdvqdgm tiakeeifgp
421 vmqilkfkti eevvgranns tyglaaavft kdldkanyis qalqagtvwv ncydvfgaqs
481 pfggykmsgs grelgeygiq aytevktvtv kvpqkns (SEQ ID NO:1)
```

FIG. 1A

```
  1 mlraaarfgp rlgrrllsaa atqavpapnq qpevfcnqif innewhdavs rktfiptvnps
 61 tgevicqvae gdkedvdkav kaaraafqlg spwrrmdash rgrilnriad lierdrtyla
121 aletldngkp yvisylvdid mvlkciryya gwadkyhgkt ipidgdffsy trhepvgvcg
181 qiipwnfpll mqawklgpal atgnvvvmkv aeqtpltaly vanlikeagf ppgvvnivpg
241 fgptagaaia shedvdkvaf tgsteigrvi qvaagssnik rvtieiggks pniimsdadm
301 dwaveqahfa lffnggqccc agsrtfvqed iydefversv araksrvvgn pfdskteqgp
361 qvdetqfkki lgyintgkqe gakilcgggi aadrgyfiqp tvfgdvqdgm tiakeeifgp
421 vmqilkfkti eevvgranns tyglaaavft kdldkanyis qalqagtvwv ncydvfgaqs
481 pfggykmsgs grelgeygiq aytkvktvtv kvpqkns (SEQ ID NO:2)
```

FIG. 1B

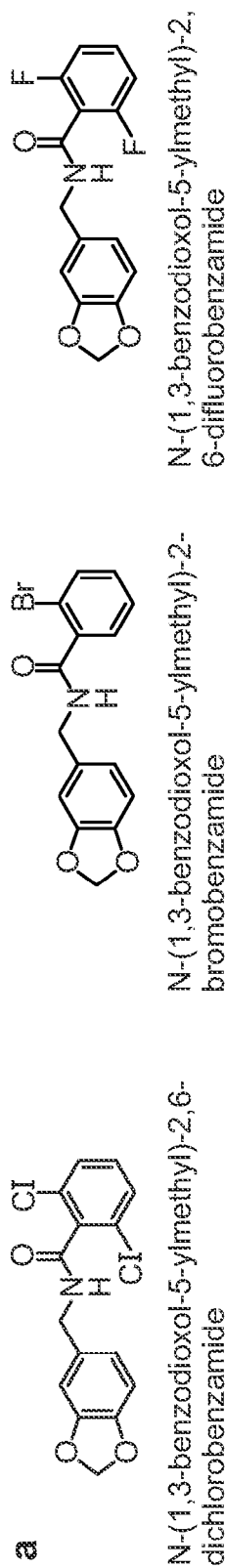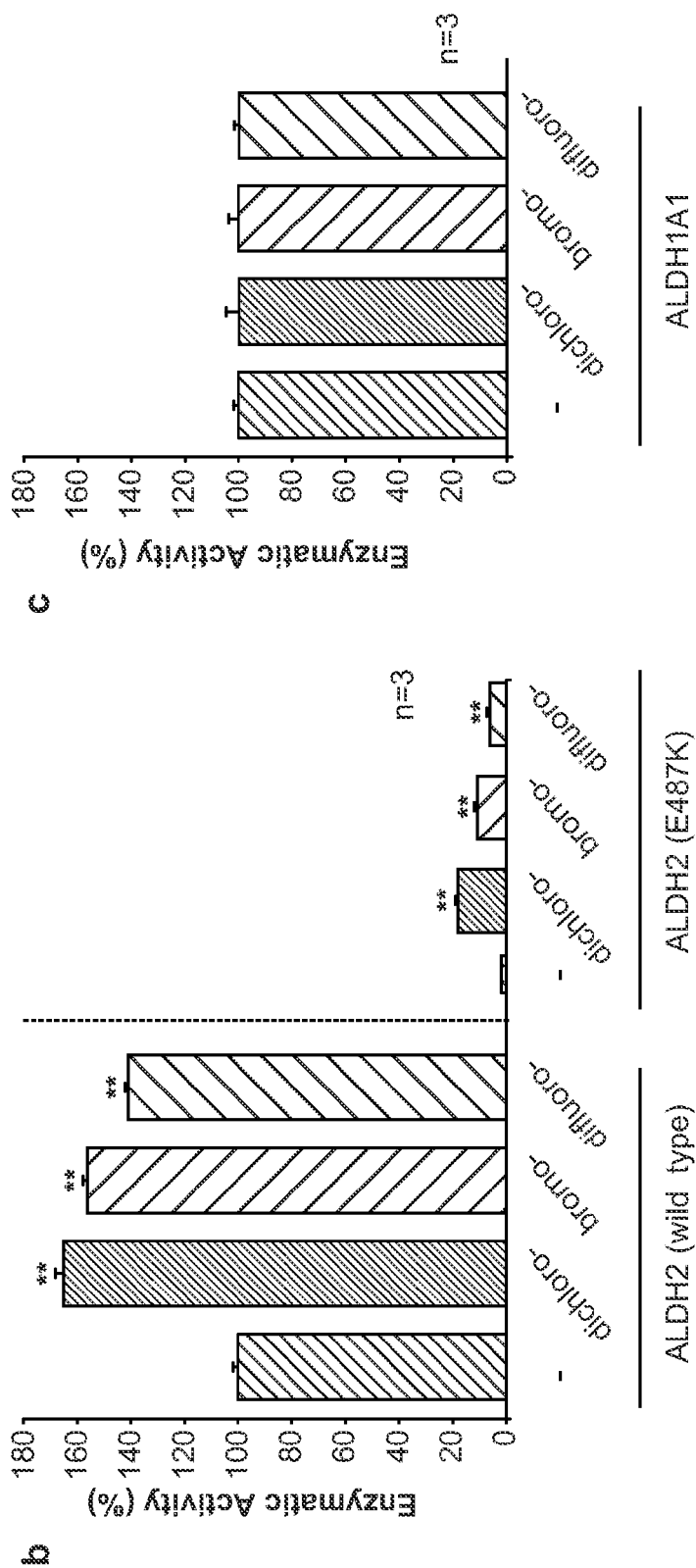
FIG. 5

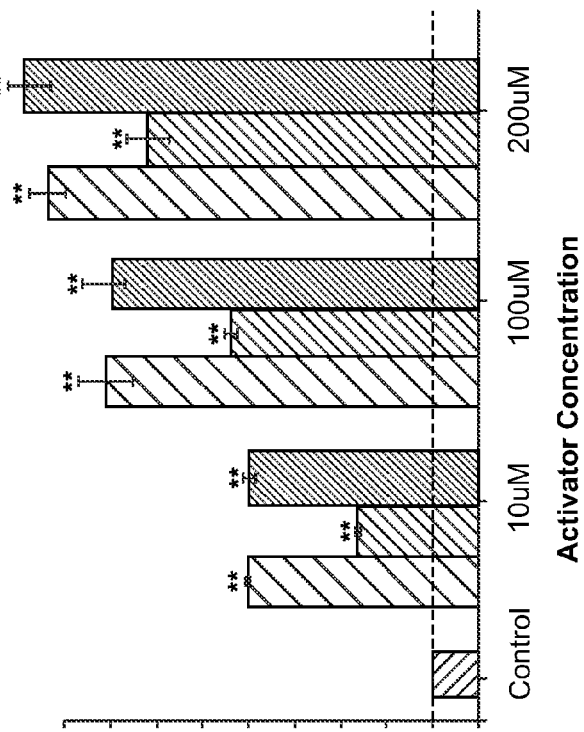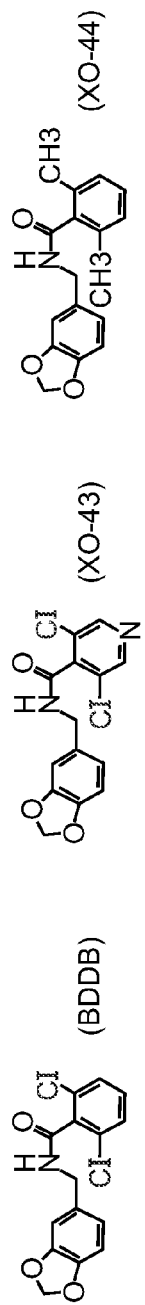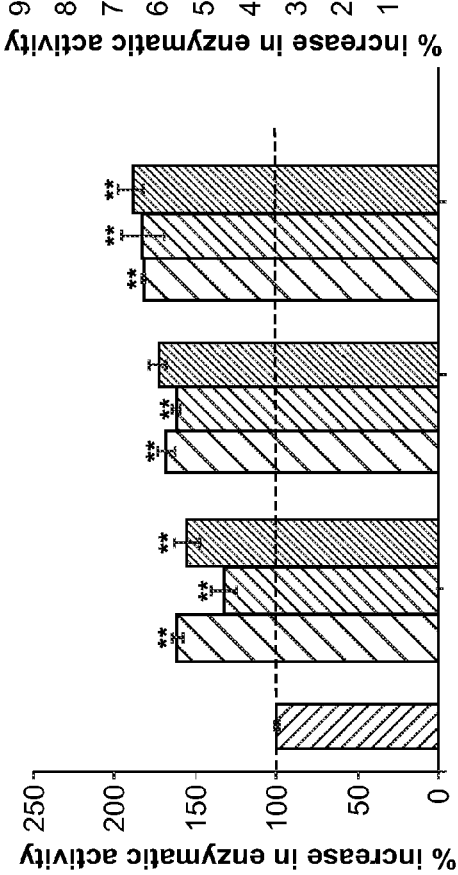
FIG. 12

MITOCHONDRIAL ALDEHYDE DEHYDROGENASE-2 MODULATORS AND METHODS OF USE THEREOF

CROSS-REFERENCE

This application is a continuation of U.S. patent application Ser. No. 12/044,870, filed Mar. 7, 2008, which claims the benefit of U.S. Provisional Patent Application No. 60/905, 963, filed Mar. 8, 2007, which applications are incorporated herein by reference in their entirety.

STATEMENT REGARDING FEDERALLY SPONSORED RESEARCH

The invention was made with government support under Grant Number AA11147 awarded by the National Institutes of Health. The government has certain rights in the invention.

BACKGROUND

Tissues deprived of blood and oxygen undergo ischemic necrosis or infarction with possible irreversible organ damage. In some circumstances, such as during surgery, interruption of blood flow resulting in ischemia of some organ is unavoidable. In addition, in the case of solid tumors, it is desirable to interrupt the blood flow and actually induce ischemia. Once the flow of blood and oxygen is restored to the organ or tissue (reperfusion), the organ does not immediately return to the normal preischemic state. For example, in the case of the ischemic myocardium, reperfused postischemic non-necrotic myocardium is poorly contractile and has reduced concentrations of high energy nucleotides, depressed subcellular organelle function and membrane damage that resolves only slowly.

Mitochondrial aldehyde dehydrogenase-2 (ALDH2) is encoded in the nuclear genome and is transported into mitochondria. ALDH2 is a tetrameric protein composed of four identical subunits, each consisting of 500 amino acid residues. This tetramer can be regarded as a dimer of dimers. The interface between monomers that form a dimer is different and more extensive than the interface between the two dimers that form the tetramer. Each subunit is composed of three main domains: the catalytic domain, the coenzyme or NAD$^+$-binding domain, and the oligomerization domain.

LITERATURE

Larson et al. (2005) *J. Biol. Chem.* 280:30550; Li et al. (2006) *J. Clin. Invest.* 116:506; US Patent Publication No. 2005/0171043; PCT Publication No. WO 2005/057213.

SUMMARY OF THE INVENTION

The present invention provides compounds that function as modulators of mitochondrial aldehyde dehydrogenase-2 (ALDH2) activity; and pharmaceutical compositions comprising the compounds. The present invention provides therapeutic methods involving administering a subject compound, or a subject pharmaceutical composition. The present invention further provides assays for identifying agonists of ALDH2.

BRIEF DESCRIPTION OF THE DRAWINGS

FIG. 1A and FIG. 1B provide the amino acid sequence of human ALDH2 (SEQ ID NO:1) and the amino acid sequence of an E487K variant of human ALDH2, respectively.

FIGS. 5A-C depict the structure of exemplary ALDH2 agonists (FIG. 5A); and results showing the specificity of exemplary ALDH2 agonists for ALDH2 (FIGS. 5B and 5C).

FIG. 12 depicts the effect of compounds BDDB, XO-43, and XO-44 on ALDH2 activity.

DEFINITIONS

Figure 2:
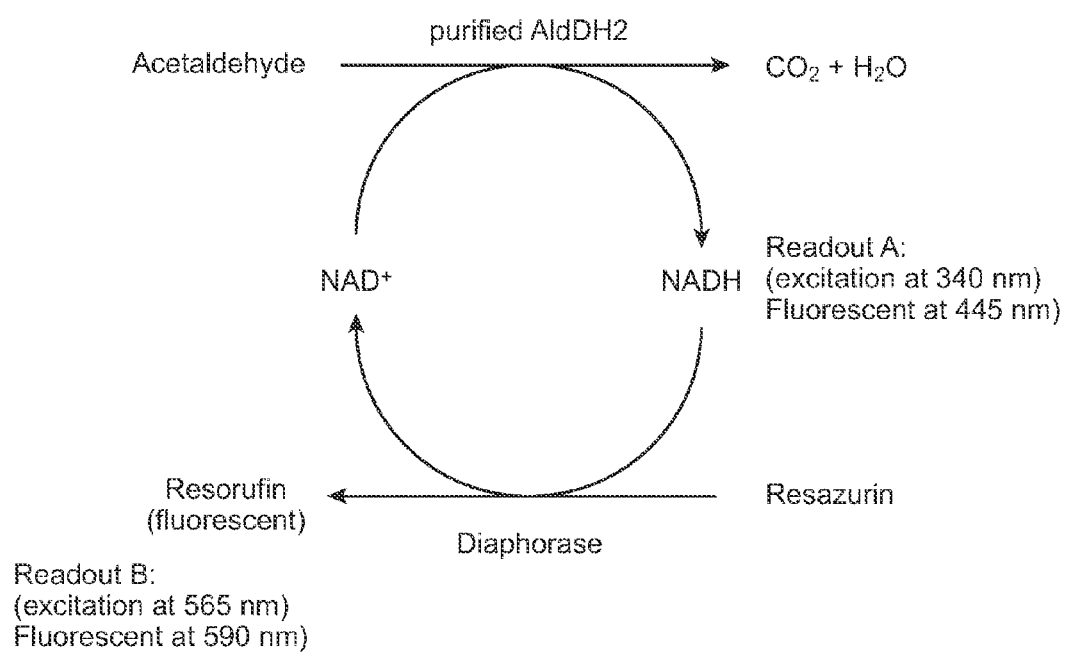
FIG. 2 schematically depicts a fluorescent aldehyde dehydrogenase enzymatic assay.

As used herein, the term "mitochondrial aldehyde dehydrogenase-2" or "ALDH2" refers to an enzyme that oxidizes an aldehyde (e.g., a xenogenic aldehyde, a biogenic aldehyde, or an aldehyde produced from a compound that is ingested, inhaled, or absorbed) to its corresponding acid in an NAD$^+$-dependent reaction. For example, ALDH2 oxidizes aldehydes derived from the breakdown of compounds, e.g., toxic compounds that are ingested, that are absorbed, that are inhaled, or that are produced during normal metabolism.

The term "ALDH2" encompasses ALDH2 from various species. Amino acid sequences of ALDH2 from various species are publicly available. For example, a human ALDH2 amino acid sequence is found under GenBank Accession Nos. AAH02967 and NP_000681; a mouse ALDH2 amino acid sequence is found under GenBank Accession No. NP_033786; and a rat ALDH2 amino acid sequence is found under GenBank Accession No. NP_115792. The term "ALDH2" as used herein also encompasses fragments, fusion proteins, and variants (e.g., variants having one or more amino acid substitutions, addition, deletions, and/or insertions) that retain ALDH2 enzymatic activity. Specific enzymatically active ALDH2 variants, fragments, fusion proteins, and the like can be verified by adapting the methods described herein. An example of an ALDH2 variant is an ALDH2 polypeptide that comprises a Glu-to-Lys substitution at amino acid position 487 of human ALDH2, as depicted in FIG. 1B (amino acid 504 of SEQ ID NO:2), or at a position corresponding to amino acid 487 of human ALDH2. This mutation is referred to as the "E487K mutation"; the "E487K variant"; or as the "Glu504Lys polymorphism". See, e.g., Larson et al. (2005) *J. Biol. Chem.* 280:30550; and Li et al. (2006) *J. Clin. Invest.* 116:506. An ALDH2 variant retains at least about 1% of the enzymatic activity of a corresponding wild-type ALDH2 enzyme. For example, the E487K variant retains at least about 1% of the activity of an enzyme comprising the amino acid sequence depicted in FIG. 1A (SEQ ID NO:1).

The term "isolated compound" means a compound which has been substantially separated from, or enriched relative to, other compounds with which it occurs in nature. Isolated compounds are at least about 80%, at least about 90% pure, at least about 98% pure, or at least about 99% pure, by weight. The present invention is meant to comprehend diastereomers as well as their racemic and resolved, enantiomerically pure forms and pharmaceutically acceptable salts thereof.

"Treating" or "treatment" of a condition or disease includes: (1) preventing at least one symptom of the conditions, i.e., causing a clinical symptom to not significantly develop in a mammal that may be exposed to or predisposed to the disease but does not yet experience or display symptoms of the disease, (2) inhibiting the disease, i.e., arresting or reducing the development of the disease or its symptoms, or (3) relieving the disease, i.e., causing regression of the disease or its clinical symptoms.

A "therapeutically effective amount" or "efficacious amount" means the amount of a compound that, when administered to a mammal or other subject for treating a disease, is sufficient, in combination with another agent, or alone in one or more doses, to effect such treatment for the disease. The "therapeutically effective amount" will vary depending on the compound, the disease and its severity and the age, weight, etc., of the subject to be treated.

The terms "subject," "individual," and "patient" are used interchangeably herein to a member or members of any mammalian or non-mammalian species that may have a need for the pharmaceutical methods, compositions and treatments described herein. Subjects and patients thus include, without limitation, primate (including humans), canine, feline, ungulate (e.g., equine, bovine, swine (e.g., pig)), avian, and other subjects. Humans and non-human mammals having commercial importance (e.g., livestock and domesticated animals) are of particular interest.

"Mammal" refers to a member or members of any mammalian species, and includes, by way of example, canines; felines; equines; bovines; ovines; rodentia, etc. and primates, particularly humans. Non-human animal models, particularly mammals, e.g. a non-human primate, a murine (e.g., a mouse, a rat), lagomorpha, etc. may be used for experimental investigations.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The term "physiological conditions" is meant to encompass those conditions compatible with living cells, e.g., predominantly aqueous conditions of a temperature, pH, salinity, etc. that are compatible with living cells.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes one and more than one such excipient, diluent, carrier, and adjuvant.

As used herein, a "pharmaceutical composition" is meant to encompass a composition suitable for administration to a subject, such as a mammal, especially a human. In general a "pharmaceutical composition" is sterile, and is free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal and the like. In some embodiments the composition is suitable for administration by a transdermal route, using a penetration enhancer other than dimethylsulfoxide (DMSO). In other embodiments, the pharmaceutical compositions are suitable for administration by a route other than transdermal administration. A pharmaceutical composition will in some embodiments include a subject compound and a pharmaceutically acceptable excipient. In some embodiments, a pharmaceutically acceptable excipient is other than DMSO.

As used herein, "pharmaceutically acceptable derivatives" of a compound of the invention include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs.

A "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

A "pharmaceutically acceptable ester" of a compound of the invention means an ester that is pharmaceutically acceptable and that possesses the desired pharmacological activity of the parent compound, and includes, but is not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids.

A "pharmaceutically acceptable enol ether" of a compound of the invention means an enol ether that is pharmaceutically acceptable and that possesses the desired pharmacological activity of the parent compound, and includes, but is not limited to, derivatives of formula C═C(OR) where R is hydrogen, alkyl, alkenyl, alkynyl, aryl, heteroaryl, aralkyl, heteroaralkyl, cycloalkyl or heterocyclyl.

A "pharmaceutically acceptable solvate or hydrate" of a compound of the invention means a solvate or hydrate complex that is pharmaceutically acceptable and that possesses the desired pharmacological activity of the parent compound, and includes, but is not limited to, complexes of a compound of the invention with one or more solvent or water molecules, or 1 to about 100, or 1 to about 10, or one to about 2, 3 or 4, solvent or water molecules.

"Pro-drugs" means any compound that releases an active parent drug according to one or more of the generic formulas shown below in vivo when such prodrug is administered to a mammalian subject. Prodrugs of a compound of one or more of the generic formulas shown below are prepared by modifying functional groups present in the compound of the generic formula in such a way that the modifications may be cleaved in vivo to release the parent compound. Prodrugs include compounds of one or more of the generic formulas shown below wherein a hydroxy, amino, or sulfhydryl group in one or more of the generic formulas shown below is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylaminocarbonyl) of hydroxy functional groups in compounds of one or more of the generic formulas shown below, and the like.

The term "organic group" and "organic radical" as used herein means any carbon-containing group, including hydrocarbon groups that are classified as an aliphatic group, cyclic group, aromatic group, functionalized derivatives thereof and/or various combinations thereof. The term "aliphatic group" means a saturated or unsaturated linear or branched hydrocarbon group and encompasses alkyl, alkenyl, and alkynyl groups, for example. The term "alkyl group" means a substituted or unsubstituted, saturated linear or branched hydrocarbon group or chain (e.g., $C_1$ to $C_8$) including, for example, methyl, ethyl, isopropyl, tert-butyl, heptyl, iso-propyl, n-octyl, dodecyl, octadecyl, amyl, 2-ethylhexyl, and the like. Suitable substituents include carboxy, protected carboxy, amino, protected amino, halo, hydroxy, protected hydroxy, nitro, cyano, monosubstituted amino, protected monosubstituted amino, disubstituted amino, $C_1$ to $C_7$ alkoxy, $C_1$ to $C_7$ acyl, $C_1$ to $C_7$ acyloxy, and the like. The term "substituted alkyl" means the above defined alkyl group substituted from one to three times by a hydroxy, protected hydroxy, amino, protected amino, cyano, halo, triflorom-ethyl, mono-substituted amino, di-substituted amino, lower alkoxy, lower alkylthio, carboxy, protected carboxy, or a carboxy, amino, and/or hydroxy salt. As used in conjunction with the substituents for the heteroaryl rings, the terms "substituted (cycloalkyl)alkyl" and "substituted cycloalkyl" are as defined below substituted with the same groups as listed for a "substituted alkyl" group. The term "alkenyl group" means an unsaturated, linear or branched hydrocarbon group with one or more carbon-carbon double bonds, such as a vinyl group. The term "alkynyl group" means an unsaturated, linear or branched hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polycyclic aromatic hydrocarbon group, and may include one or more heteroatoms, and which are further defined below. The term "heterocyclic group" means a closed ring hydrocarbon in which one or more of the atoms in the ring are an element other than carbon (e.g., nitrogen, oxygen, sulfur, etc.), and are further defined below.

"Organic groups" may be functionalized or otherwise comprise additional functionalities associated with the organic group, such as carboxyl, amino, hydroxyl, and the like, which may be protected or unprotected. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ethers, esters, haloalkyls, nitroalkyls, carboxyalkyls, hydroxyalkyls, sulfoalkyls, etc.

The terms "halo" and "halogen" refer to the fluoro, chloro, bromo or iodo groups. There can be one or more halogen, which are the same or different. Halogens of particular interest include chloro and bromo groups.

The term "haloalkyl" refers to an alkyl group as defined above that is substituted by one or more halogen atoms. The halogen atoms may be the same or different. The term "dihaloalkyl" refers to an alkyl group as described above that is substituted by two halo groups, which may be the same or different. The term "trihaloalkyl" refers to an alkyl group as describe above that is substituted by three halo groups, which may be the same or different. The term "perhaloalkyl" refers to a haloalkyl group as defined above wherein each hydrogen atom in the alkyl group has been replaced by a halogen atom. The term "perfluoroalkyl" refers to a haloalkyl group as defined above wherein each hydrogen atom in the alkyl group has been replaced by a fluoro group.

The term "cycloalkyl" means a mono-, bi-, or tricyclic saturated ring that is fully saturated or partially unsaturated. Examples of such a group included cyclopropyl, cyclobutyl, cyclopentyl, cyclohexyl, cycloheptyl, adamantyl, cyclooctyl, cis- or trans decalin, bicyclo[2.2.1]hept-2-ene, cyclohex-1-enyl, cyclopent-1-enyl, 1,4-cyclooctadienyl, and the like.

The term "(cycloalkyl)alkyl" means the above-defined alkyl group substituted for one of the above cycloalkyl rings. Examples of such a group include (cyclohexyl)methyl, 3-(cyclopropyl)-n-propyl, 5-(cyclopentyl)hexyl, 6-(adamantyl) hexyl, and the like.

The term "substituted phenyl" specifies a phenyl group substituted with one or more moieties, and in some instances one, two, or three moieties, chosen from the groups consisting of halogen, hydroxy, protected hydroxy, cyano, nitro, trifluoromethyl, $C_1$ to $C_7$ alkyl, $C_1$ to $C_7$ alkoxy, $C_1$ to $C_7$ acyl, $C_1$ to $C_7$ acyloxy, carboxy, oxycarboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_6$ alkyl)carboxamide, protected N—($C_1$ to $C_6$ alkyl)carboxamide, N,N-di($C_1$ to $C_6$ alkyl)carboxamide, trifluoromethyl, N—(($C_1$ to $C_6$ alkyl)sulfonyl)amino, N-(phenylsulfonyl)amino or phenyl, substituted or unsubstituted, such that, for example, a biphenyl or naphthyl group results.

Examples of the term "substituted phenyl" includes a mono- or di(halo)phenyl group such as 2, 3 or 4-chlorophenyl, 2,6-dichlorophenyl, 2,5-dichlorophenyl, 3,4-dichlorophenyl, 2, 3 or 4-bromophenyl, 3,4-dibromophenyl, 3-chloro-4-fluorophenyl, 2, 3 or 4-fluorophenyl and the like; a mono or di(hydroxy)phenyl group such as 2, 3, or 4-hydroxyphenyl, 2,4-dihydroxyphenyl, the protected-hydroxy derivatives thereof and the like; a nitrophenyl group such as 2, 3, or 4-nitrophenyl; a cyanophenyl group, for example, 2, 3 or 4-cyanophenyl; a mono- or di(alkyl)phenyl group such as 2, 3, or 4-methylphenyl, 2,4-dimethylphenyl, 2, 3 or 4-(isopropyl)phenyl, 2, 3, or 4-ethylphenyl, 2, 3 or 4-(n-propyl) phenyl and the like; a mono or di(alkoxy)phenyl group, for example, 2,6-dimethoxyphenyl, 2, 3 or 4-(isopropoxy)phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy)phenyl group such as 2, 3 or 4-carboxyphenyl or 2,4-di(protected carboxy)phenyl; a mono- or di(hydroxymethyl)phenyl or (protected hydroxymethyl)phenyl such as 2, 3 or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl)phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like.

The term "(substituted phenyl)alkyl" means one of the above substituted phenyl groups attached to one of the above-described alkyl groups. Examples of include such groups as 2-phenyl-1-chloroethyl, 2-(4'-methoxyphenyl)ethyl, 4-(2',6'-dihydroxy phenyl)n-hexyl, 2-(5'-cyano-3'-methoxyphenyl) n-pentyl, 3-(2',6'-dimethylphenyl)n-propyl, 4-chloro-3-aminobenzyl, 6-(4'-methoxyphenyl)-3-carboxy(n-hexyl), 5-(4'-aminomethylphenyl)-3-(aminomethyl)n-pentyl, 5-phenyl-3-oxo-n-pent-1-yl, (4-hydroxynapth-2-yl)methyl and the like.

As noted above, the term "aromatic" or "aryl" refers to six membered carbocyclic rings. Also as noted above, the term "heteroaryl" denotes optionally substituted five-membered or six-membered rings that have 1 to 4 heteroatoms, such as oxygen, sulfur and/or nitrogen atoms, in particular nitrogen, either alone or in conjunction with sulfur or oxygen ring atoms.

Furthermore, the above optionally substituted five-membered or six-membered rings can optionally be fused to an aromatic 5-membered or 6-membered ring system. For example, the rings can be optionally fused to an aromatic 5-membered or 6-membered ring system such as a pyridine or a triazole system, and preferably to a benzene ring.

The following ring systems are examples of the heterocyclic (whether substituted or unsubstituted) radicals denoted by the term "heteroaryl": thienyl, furyl, pyrrolyl, pyrrolidinyl, imidazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, oxazinyl, triazinyl, thiadiazinyl tetrazolo, 1,5-[b]pyridazinyl and purinyl, as well as benzo-fused derivatives, for example, benzoxazolyl, benzthiazolyl, benzimidazolyl and indolyl.

Substituents for the above optionally substituted heteroaryl rings are from one to three halo, trihalomethyl, amino, protected amino, amino salts, mono-substituted amino, di-substituted amino, carboxy, protected carboxy, carboxylate salts, hydroxy, protected hydroxy, salts of a hydroxy group, lower alkoxy, lower alkylthio, alkyl, substituted alkyl, cycloalkyl, substituted cycloalkyl, (cycloalkyl)alkyl, substituted (cycloalkyl)alkyl, phenyl, substituted phenyl, phenylalkyl, and (substituted phenyl)alkyl. Substituents for the heteroaryl group are as heretofore defined, or in the case of trihalomethyl, can be trifluoromethyl, trichloromethyl, tribromomethyl, or triiodomethyl. As used in conjunction with the above substituents for heteroaryl rings, "lower alkoxy" means a $C_1$ to $C_4$ alkoxy group, similarly, "lower alkylthio" means a $C_1$ to $C_4$ alkylthio group.

The term "(monosubstituted)amino" refers to an amino group with one substituent chosen from the group consisting of phenyl, substituted phenyl, alkyl, substituted alkyl, $C_1$ to $C_4$ acyl, $C_2$ to $C_7$ alkenyl, $C_2$ to $C_7$ substituted alkenyl, $C_2$ to $C_7$ alkynyl, $C_7$ to $C_{16}$ alkylaryl, $C_7$ to $C_{16}$ substituted alkylaryl and heteroaryl group. The (monosubstituted) amino can additionally have an amino-protecting group as encompassed by the term "protected (monosubstituted)amino." The term "(disubstituted)amino" refers to amino groups with two substituents chosen from the group consisting of phenyl, substituted phenyl, alkyl, substituted alkyl, $C_1$ to $C_7$ acyl, $C_2$ to $C_7$ alkenyl, $C_2$ to $C_7$ alkynyl, $C_7$ to $C_{16}$ alkylaryl, $C_7$ to $C_{16}$ substituted alkylaryl and heteroaryl. The two substituents can be the same or different.

The term "heteroaryl(alkyl)" denotes an alkyl group as defined above, substituted at any position by a heteroaryl group, as above defined.

"Optional" or "optionally" means that the subsequently described event, circumstance, feature, or element may, but need not, occur, and that the description includes instances where the event or circumstance occurs and instances in which it does not. For example, "heterocyclo group optionally mono- or di-substituted with an alkyl group" means that the alkyl may, but need not, be present, and the description includes situations where the heterocyclo group is mono- or disubstituted with an alkyl group and situations where the heterocyclo group is not substituted with the alkyl group.

Compounds that have the same molecular formula but differ in the nature or sequence of bonding of their atoms or the arrangement of their atoms in space are termed "isomers." Isomers that differ in the arrangement of their atoms in space are termed "stereoisomers." Stereoisomers that are not minor images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

A subject compound may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see, e.g., the discussion in Chapter 4 of "Advanced Organic Chemistry", 4th edition J. March, John Wiley and Sons, New York, 1992).

"In combination with" as used herein refers to uses where, for example, the first compound is administered during the entire course of administration of the second compound; where the first compound is administered for a period of time that is overlapping with the administration of the second compound, e.g. where administration of the first compound begins before the administration of the second compound and the administration of the first compound ends before the administration of the second compound ends; where the administration of the second compound begins before the administration of the first compound and the administration of the second compound ends before the administration of the first compound ends; where the administration of the first compound begins before administration of the second compound begins and the administration of the second compound ends before the administration of the first compound ends; where the administration of the second compound begins before administration of the first compound begins and the administration of the first compound ends before the administration of the second compound ends. As such, "in combination" can also refer to regimen involving administration of two or more compounds. "In combination with" as used herein also refers to administration of two or more compounds which may be administered in the same or different formulations, by the same of different routes, and in the same or different dosage form type.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a mitochondrial aldehyde dehydrogenase-2 agonist" includes a plurality of such agonists and reference to "the pharmaceutical composition" includes reference to one or more pharmaceutical compositions and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present invention provides compounds that function as modulators of mitochondrial aldehyde dehydrogenase-2 (ALDH2) activity; and pharmaceutical compositions comprising the compounds. Agonists of ALDH2 are useful for treating a variety of disorders, including, e.g., conditions involving ischemic stress, chronic free-radical associated diseases, acute free-radical associated diseases, insensitivity to nitroglycerin (e.g., in angina and heart failure), hypertension, diabetes, and osteoporosis. Agonists of ALDH2 are also useful for reducing the level in an individual of a compound such as ethanol, methanol, ethylene glycol monomethyl ether, polyvinyl chloride, xenogenic aldehydes, and biogenic aldehydes. Agonists of ALDH2 are also useful for reducing the level in an individual of a compound that, when ingested, absorbed, or inhaled, gives rise to an aldehyde substrate for ALDH2. Antagonists of ALDH2 are useful for treating disorders such as cancer, where the ALDH2 antagonist is used as an adjuvant to a standard cancer therapy. Antagonists of ALDH2 are also useful for treating alcoholism. Antagonists of ALDH2 are also useful for treating narcotic addiction. The present invention provides therapeutic methods involving administering a subject compound, or a subject pharmaceutical composition. The present invention further provides assays for identifying agonists of ALDH2.

In some embodiments, individuals to be treated are humans. In some embodiments, a human to be treated according to a subject method is one that has two "wild-type" ALDH2 alleles, e.g., the ALDH2 encoded by the two wild-type ALDH2 alleles has a glutamic acid at position 487, as depicted in FIG. 1A. In other embodiments, a human to be treated according to a subject method is one that has one or two "ALDH2*2" alleles, e.g., the ALDH2 encoded by one or both ALDH2 alleles comprises a lysine as amino acid position 487, as depicted in FIG. 1B. The E487K polymorphism is a semidominant polymorphism, and results in an ALDH2 tetramer that has significantly lower enzymatic activity than "wild-type" ALDH2. Thus, individuals who are heterozygous or homozygous for the ALDH2*2 allele have much lower in vivo ALDH2 activity levels than individuals who are homozygous for the "wild-type" ALDH2 allele. Individuals who are heterozygous or homozygous for the ALDH2*2 allele are expected to benefit from treatment with a subject ALDH2 agonist, because the level of ALDH2 activity in such individuals is particularly low, and any increase of ALDH2 activity levels would be expected to provide a therapeutic effect. Any increase in ALDH2 activity would be beneficial in treating conditions such as ischemic disorders, in increasing the responsiveness of such individuals to nitroglycerin, etc., as discussed in more detail below.

The use of ALDH2 variants, such as an E487K ALDH2 variant, in screening methods to identify ALDH2 activators (agonists) is also provided. Because the E487K ALDH2 variant has lower enzymatic activity than the "wild-type" ALDH2, the readout for agonist activity of a test compound is more sensitive.

Modulators of Mitochondrial Aldehyde Dehydrogenase-2

The present invention provides compounds that function as modulators of mitochondrial aldehyde dehydrogenase-2 (ALDH2) activity; and pharmaceutical compositions comprising the compounds. Modulators include agonists (also referred to herein as "activators") and antagonists (also referred to herein as "inhibitors").

In some embodiments, a compound that modulates ALDH2 activity modulates a dehydrogenase activity of ALDH2, e.g., the compound modulates dehydrogenase activity in oxidizing an aldehyde (e.g., a xenogenic aldehyde, a biogenic aldehyde, or an aldehyde produced from a compound that is ingested, inhaled, or absorbed) to the corresponding acid. In other embodiments, a compound that modulates ALDH2 activity modulates an esterase activity of ALDH2. In other embodiments, a compound that modulates ALDH2 activity modulates a reductase activity of ALDH2. For example, ALDH2 can convert nitroglycerin to nitric oxide (NO) via its reductase activity.

As noted above, in some embodiments, a compound that modulates ALDH2 activity modulates a dehydrogenase activity of ALDH2, e.g., the compound modulates dehydrogenase activity in oxidizing an aldehyde (e.g., a xenogenic aldehyde, a biogenic aldehyde, or an aldehyde produced from a compound that is ingested, inhaled, or absorbed) to the corresponding acid.

A variety of compounds can give rise to aldehyde substrates for ALDH2. Non-limiting examples of compounds that can give rise to aldehyde substrates for ALDH2 include ethanol; a variety of insecticides; industrial toxins such as vinyl chlorides (e.g., polyvinyl chloride); and pyruvate. For example, a compound is ingested, absorbed (e.g., through the skin), or inhaled, by a mammal and is subsequently converted in the mammal into an aldehyde substrate for ALDH2.

Biogenic aldehydes include aldehydes that are produced by a mammal, e.g., are produced metabolically by a mammal. Non-limiting examples of biogenic aldehydes include ω-6 polyunsaturated fatty acids, such as malondialdehyde (MDA); hexanal; acrolein; glyoxal; crotonaldehyde; trans-2-nonenal; 4-oxo-2-nonenal; and 4-hydroxy-2-nonenal (HNE) (see e.g., Ellis, Pharmacology & Therapeutics (2007) 115:13, Picklo and Montine (2007) J Alzheimers Dis. 12:185); 3-aminopropanal (3-AP), a product of polyamine oxidase; and aldehyde products of tyrosine, serine and threonine (see Wood et al, Brain Res (2006)1095; 190).

Xenogenic aldehydes include aldehydes ingested, absorbed, or inhaled by a mammal from source outside the mammal. Xenogenic aldehydes include, e.g., formaldehyde and glutaraldehyde (e.g., McGregor et al., Crit. Rev Toxicol (2006) 36:821 and Pandey et al Hum Exp. Toxicol. (2000) 19:360); chloroacetaldehyde (see e.g., Richardson et al., Mutat. Research (2007) 636:178); and reactive aldehydes present in cigarette smoke (see Simth et al., Inhal. Toxicol. (2006) 18:667).

Non-limiting examples of compounds that are substrates for mitochondrial ALDH2 include 3,4-dihydroxypheylacetaldehyde (DOPAL); formaldehyde; acetaldehyde; propionaldehyde; n-butyraldehyde; capronaldehyde; heptaldehyde; pentaldehyde; octylaldehyde; decylaldehyd; retinaldehyde; 3-hydroxybenzaldehyde; 2,5-dihydroxybenzaldehyde; phenylacetaldehyde; 3-phenylpropionaldehyde (see, e.g., Want et al. (2002) Drug Metabolism and Disposition 30:69); cinnamoyl and hydrocinnamoyl aldehydes and their derivative aldehydes (e.g. p-nitrocinnamaldehyde, p-(dimethylamino)cinnamaldehyde, hydrocinnamaldehyde, α-phenylpropionaldehyde); benzaldehyde and its derivative aldehydes (e.g. 2,4-dinitro-benzaldehyde, o-nitro-benzaldehyde, p-nitro-benzaldehyde, p-methyl-benzaldehyde, m-methyl-benzaldehyde, p-methoxy-benzaldehyde, p-(dimethylamino)-benzaldehyde, m-methoxy-benzaldehyde, m-hydroxy-benzaldehyde, 3,4-dimethoxy-benzaldehyde, o-methoxy-benzaldehyde); naphthaldehyde and its derivative aldehydes (e.g. 5-bromo-1-naphthaldehyde, 5-nitro-1-naphthaldehyde, 6-[O—(CH$_2$)$_5$—COOH]-2-naphthaldehyde, 6-(dimethylamino)-2-naphthaldehyde); coumarin-4-carboxaldehyde and its derivative aldehydes (e.g. 7-acetoxy-coumarin-4-carboxaldehyde, 7-(dimethylamino)-coumarin-4-carboxaldehyde, 7-methoxy-coumarin-4-carboxaldehyde, 6,7-dimethoxy-coumarin-4-carboxaldehyde); quinoline, quinolinonecarboxaldehyde, and their derivative aldehydes (e.g. quinoline-3-carboxaldehyde, 7-(dimethylamino)-2-quinolinone-4-carboxaldehyde, quinoline-4-carboxaldehyde, 6-methoxy-2-quinolinone-4-carboxaldehyde); phenanthrene-9-carboxaldehyde; indole-3-aldehyde, indole-3-actaldehyde; 5-methoxyindole-3-carboxaldehyde; 3-pyridinecarboxaldehyde; fluorene-2-carboxaldehyde (see, e.g., Klyosov, (1996) Biochemstry 35:4457); 4-hydroxynonenal; malondialdehyde; 3,4-dihydroxyphenylacetaldehyde; and 5-hydroxylindole-3-acetaldehyde. See, also, e.g., Williams et al. (2005) Anal. Chem. 77:3383; Marchitti et al. (2007) Pharmacol. Rev. 59:125; and Hoffman and Maser (2007) Drug Metab. Rev. 39:87.

ALDH2 Agonists

The present invention provides ALDH2 agonists (also referred to as "activators"); and pharmaceutical compositions comprising ALDH2 agonists. Agonists of ALDH2 are useful for treating a variety of disorders, including, e.g., conditions involving ischemic stress, chronic free-radical associated diseases, acute free-radical associated diseases, insensitivity to nitroglycerin (e.g., in angina and heart failure), hypertension, diabetes, and osteoporosis. Agonists are also useful in the detoxification of alcohol abuse, methanol poisoning, ethylene glycol monomethyl ether poisoning, and poisoning due to other xenogenic or biogenic aldehyde compounds.

An ALDH2 agonist increases an enzymatic activity of an ALDH2 polypeptide by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the enzymatic activity of the ALDH2 polypeptide in the absence of the agonist.

In some embodiments, an ALDH2 agonist increases a dehydrogenase activity (e.g., dehydrogenase activity in oxidizing an aldehyde (e.g., a xenogenic aldehyde, a biogenic aldehyde, or an aldehyde produced from a compound that is ingested, inhaled, or absorbed) to the corresponding acid) of an ALDH2 polypeptide by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the dehydrogenase activity of the ALDH2 polypeptide in the absence of the agonist.

In some embodiments, an ALDH2 agonist increases the esterase activity of an ALDH2 polypeptide by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the esterase activity of the ALDH2 polypeptide in the absence of the agonist.

In some embodiments, an ALDH2 agonist increases the reductase activity of an ALDH2 polypeptide by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the reductase activity of the ALDH2 polypeptide in the absence of the agonist.

In some embodiments, an ALDH2 agonist increases an enzymatic activity of an ALDH2 polypeptide comprising an amino acid sequence set forth in SEQ ID NO:1 (depicted in FIG. 1A), or as set forth in amino acids 18-517 of SEQ ID NO:1, by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the enzymatic activity of the ALDH2 polypeptide in the absence of the agonist.

In some embodiments, an ALDH2 agonist increases a dehydrogenase activity (e.g., dehydrogenase activity in oxidizing an aldehyde (e.g., a xenogenic aldehyde, a biogenic aldehyde, or an aldehyde produced from a compound that is ingested, inhaled, or absorbed) to the corresponding acid) of an ALDH2 polypeptide comprising an amino acid sequence set forth in SEQ ID NO:1 (depicted in FIG. 1A), or as set forth in amino acids 18-517 of SEQ ID NO:1, by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the dehydrogenase activity of the ALDH2 polypeptide in the absence of the agonist.

In some embodiments, an ALDH2 agonist increases an esterase activity of an ALDH2 polypeptide comprising an amino acid sequence set forth in SEQ ID NO:1 (depicted in FIG. 1A), or as set forth in amino acids 18-517 of SEQ ID NO:1, by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the esterase activity of the ALDH2 polypeptide in the absence of the agonist.

In some embodiments, an ALDH2 agonist increases a reductase activity of an ALDH2 polypeptide comprising an amino acid sequence set forth in SEQ ID NO:1 (depicted in FIG. 1A), or as set forth in amino acids 18-517 of SEQ ID NO:1, by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the reductase activity of the ALDH2 polypeptide in the absence of the agonist.

In some embodiments, an ALDH2 agonist increases an enzymatic activity of an ALDH2 polypeptide comprising an amino acid sequence set forth in SEQ ID NO:2 (depicted in FIG. 1B), or as set forth in amino acids 18-517 of SEQ ID NO:2, by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the enzymatic activity of the ALDH2 polypeptide in the absence of the agonist.

In some embodiments, an ALDH2 agonist increases a dehydrogenase activity (e.g., dehydrogenase activity in oxidizing an aldehyde (e.g., a xenogenic aldehyde, a biogenic aldehyde, or an aldehyde produced from a compound that is ingested, inhaled, or absorbed) to the corresponding acid) of an ALDH2 polypeptide comprising an amino acid sequence set forth in SEQ ID NO:2 (depicted in FIG. 1B), or as set forth in amino acids 18-517 of SEQ ID NO:2, by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the dehydrogenase activity of the ALDH2 polypeptide in the absence of the agonist.

In some embodiments, an ALDH2 agonist increases an esterase activity of an ALDH2 polypeptide comprising an amino acid sequence set forth in SEQ ID NO:2 (depicted in FIG. 1B), or as set forth in amino acids 18-517 of SEQ ID NO:2, by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the esterase activity of the ALDH2 polypeptide in the absence of the agonist.

In some embodiments, an ALDH2 agonist increases a reductase activity of an ALDH2 polypeptide comprising an amino acid sequence set forth in SEQ ID NO:2 (depicted in FIG. 1B), or as set forth in amino acids 18-517 of SEQ ID NO:2, by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the reductase activity of the ALDH2 polypeptide in the absence of the agonist.

In some embodiments, ALDH2 agonists are specific for (e.g., selective for) ALDH2, e.g., a subject ALDH2 agonist increases an enzymatic activity of an ALDH2 enzyme, but does not substantially increase the same enzymatic activity of cytosolic aldehyde dehydrogenase-1 (ALDH1), e.g., a subject ALDH2 agonist increases an enzymatic activity of an ALDH1 enzyme, if at all, by less than about 5%, less than about 2%, or less than about 1%, when used at a concentration that increases the same enzymatic activity of an ALDH2 enzyme by at least about 5% or more. In some embodiments, a subject ALDH2 agonist does not substantially increase the enzymatic activity of alcohol dehydrogenase (ADH), e.g., a subject ALDH2 agonist increases the enzymatic activity of an ADH, if at all, by less than about 5%, less than about 2%, or less than about 1%, when used at a concentration that increases the enzymatic activity of an ALDH2 enzyme by at least about 5% or more.

For example, in some embodiments, a subject ALDH2 agonist is specific for (e.g., selective for) ALDH2, e.g., a subject ALDH2 agonist increases dehydrogenase activity of an ALDH2 enzyme, but does not substantially increase the dehydrogenase activity of cytosolic aldehyde dehydrogenase-1 (ALDH1), e.g., a subject ALDH2 agonist increases dehydrogenase activity of an ALDH1 enzyme, if at all, by less than about 5%, less than about 2%, or less than about 1%, when used at a concentration that increases dehydrogenase activity of an ALDH2 enzyme by at least about 5% or more. In some embodiments, a subject ALDH2 agonist does not substantially increase dehydrogenase activity of alcohol dehydrogenase (ADH), e.g., a subject ALDH2 agonist increases the dehydrogenase activity of an ADH, if at all, by less than about 5%, less than about 2%, or less than about 1%, when used at a concentration that increases the dehydrogenase activity of an ALDH2 enzyme by at least about 5% or more.

In some embodiments, a subject ALDH2 agonist has an $EC_{50}$ of from about 1 nM to about 1 mM, e.g., from about 1 nM to about 10 nM, from about 10 nM to about 15 nM, from about 15 nM to about 25 nM, from about 25 nM to about 50 nM, from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, from about 450 nM to about 500 nM, from about 500 nM to about 750 nM, from about 750 nM to about from about 1 µM to about 10 µM, from about 10 µM to about 25 µM, from about 25 µM to about 50 µM, from about 50 µM to about 75 µM, from about 75 µM to about 100 µM, from about 100 µM to about 250 µM, from about 250 µM to about 500 µM, or from about 500 µM to about 1 mM.

For example, in some embodiments, a subject ALDH2 agonist has an $EC_{50}$ of from about 1 nM to about 1 mM, e.g., from about 1 nM to about 10 nM, from about 10 nM to about 15 nM, from about 15 nM to about 25 nM, from about 25 nM to about 50 nM, from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, from about 450 nM to about 500 nM, from about 500 nM to about 750 nM, from about 750 nM to about from about 1 µM to about 10 µM, from about 10 µM to about 25 µM, from about 25 µM to about 50 µM, from about 50 µM to about 75 µM, from about 75 µM to about 100 µM, from about 100 µM to about 250 µM, from about 250 µM to about 500 µM, or from about 500 µM to about 1 mM, for a dehydrogenase activity of mitochondrial ALDH2.

In some embodiments, a subject ALDH2 agonist has an $EC_{50}$ for an ALDH2 polypeptide comprising an amino acid sequence set forth in SEQ ID NO:1 (depicted in FIG. 1A), or as set forth in amino acids 18-517 of SEQ ID NO:1, of from about 1 nM to about 1 mM, e.g., from about 1 nM to about 10 nM, from about 10 nM to about 15 nM, from about 15 nM to about 25 nM, from about 25 nM to about 50 nM, from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, from about 450 nM to about 500 nM, from about 500 nM to about 750 nM, from about 750 nM to about from about 1 µM to about 10 µM, from about 10 µM to about 25 µM, from about 25 µM to about 50 µM, from about 50 µM to about 75 µM, from about 75 µM to about 100 µM, from about 100 µM to about 250 µM, from about 250 µM to about 500 µM, or from about 500 µM to about 1 mM.

For example, in some embodiments, a subject ALDH2 agonist has an $EC_{50}$ for dehydrogenase activity of an ALDH2 polypeptide comprising an amino acid sequence set forth in SEQ ID NO:1 (depicted in FIG. 1A), or as set forth in amino acids 18-517 of SEQ ID NO:1, of from about 1 nM to about 1 mM, e.g., from about 1 nM to about 10 nM, from about 10 nM to about 15 nM, from about 15 nM to about 25 nM, from about 25 nM to about 50 nM, from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, from about 450 nM to about 500 nM, from about 500 nM to about 750 nM, from about 750 nM to about from about 1 µM to about 10 µM, from about 10 µM to about 25 µM, from about 25 µM to about 50 µM, from about 50 µM to about 75 µM, from about 75 µM to about 100 µM, from about 100 µM to about 250 µM, from about 250 µM to about 500 µM, or from about 500 µM to about 1 mM.

In some embodiments, a subject ALDH2 agonist has an $EC_{50}$ for an ALDH2 polypeptide comprising an amino acid sequence set forth in SEQ ID NO:2 (depicted in FIG. 1B), or as set forth in amino acids 18-517 of SEQ ID NO:2, of from about 1 nM to about 1 mM, e.g., from about 1 nM to about 10 nM, from about 10 nM to about 15 nM, from about 15 nM to about 25 nM, from about 25 nM to about 50 nM, from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, from about 450 nM to about 500 nM, from about 500 nM to about 750 nM, from about 750 nM to about 1 µM to about 10 µM, from about 10 µM to about 25 µM, from about 25 µM to about 50 µM, from about 50 µM to about 75 µM, from about 75 µM to about 100 µM, from about 100 µM to about 250 µM, from about 250 µM to about 500 µM, or from about 500 µM to about 1 mM.

In some embodiments, a subject ALDH2 agonist has an EC$_{50}$ for dehydrogenase activity of an ALDH2 polypeptide comprising an amino acid sequence set forth in SEQ ID NO:2 (depicted in FIG. 1B), or as set forth in amino acids 18-517 of SEQ ID NO:2, of from about 1 nM to about 1 mM, e.g., from about 1 nM to about 10 nM, from about 10 nM to about 15 nM, from about 15 nM to about 25 nM, from about 25 nM to about 50 nM, from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, from about 450 nM to about 500 nM, from about 500 nM to about 750 nM, from about 750 nM to about from about 1 µM to about 10 µM, from about 10 µM to about 25 µM, from about 25 µM to about 50 µM, from about 50 µM to about 75 µM, from about 75 µM to about 100 µM, from about 100 µM to about 250 µM, from about 250 µM to about 500 µM, or from about 500 µM to about 1 mM.

In some embodiments, a subject ALDH2 agonist is an N-benzyl-benzamide compound. In some embodiments, a subject ALDH2 agonist is a compound of generic Formula I, as shown below:

Formula I

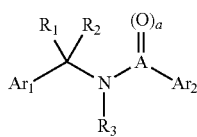

where each of $R_1$, $R_2$, and $R_3$ is independently selected from H; a halo (e.g., bromo, fluoro, chloro, iodo); a substituted or unsubstituted phenyl group; an aliphatic group, an alkyl group; a substituted alkyl group; an alkenyl group; an alkynyl group; a substituted or unsubstituted cyclic group; a substituted or unsubstituted heterocyclic group; a substituted or unsubstituted aryl group; and a substituted or unsubstituted heteroaryl group;

where A is C or S and where a=1 when A=C; and where a=2 when A=S; and where $Ar_1$ and $Ar_2$ are independently selected from a substituted aryl group, an unsubstituted aryl group, a substituted heteroaryl group, and an unsubstituted heteroaryl group;

or a pro-drug, a pharmaceutically acceptable salt, an analog, or a derivative thereof.

For example, in some embodiments, $Ar_1$ and $Ar_2$ of Formula I are independently:

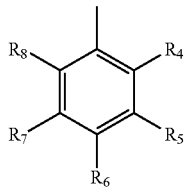

where $R_4$-$R_8$ are each independently selected from H; a halo (e.g., bromo, fluoro, chloro, iodo); a substituted or unsubstituted phenyl group; an aliphatic group, an alkyl group; a substituted alkyl group; an alkenyl group; an alkynyl group; a substituted or unsubstituted cyclic group; a substituted or unsubstituted heterocyclic group; a substituted or unsubstituted aryl group; and a substituted or unsubstituted heteroaryl group. In other embodiments, $Ar_1$ and $Ar_2$ of Formula I are independently a substituted or unsubstituted heterocyclic group, e.g., a substituted or unsubstituted pyridine, a thiazole, an imidazole, a thiophene, a quinoline, an isoquinoline, or a furan group.

In some embodiments, a subject ALDH2 agonist is an N-benzyl-benzamide compound. In some embodiments, a subject ALDH2 agonist is a compound of generic Formula II, as shown below:

Formula II

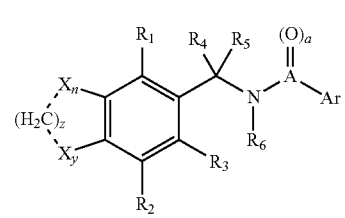

where $X_n$ and $X_y$ are each independently H, C, N, O, or a halogen (e.g., F, Br, Cl, or I); where n is the integer 0 or 1; where y is the integer 0 or 1;

where . . . (dotted line) is an optional bond; where z is the integer 0, 1, or 2;

where A is C or S, and where a=1 when A=C; and where a=2 when A=S;

where Ar is an unsubstituted or substituted aryl group, a substituted heteroaryl group, or an unsubstituted heteroaryl group; and where $R_1$ to $R_6$ is each independently selected from H; a halo (e.g., bromo, fluoro, chloro, iodo); a substituted or unsubstituted phenyl group; an aliphatic group, an alkyl group; a substituted alkyl group; an alkenyl group; an alkynyl group; a substituted or unsubstituted cyclic group; a substituted or unsubstituted heterocyclic group; a substituted or unsubstituted aryl group; and a substituted or unsubstituted heteroaryl group;

or a pro-drug, a pharmaceutically acceptable salt, an analog, or a derivative thereof.

For example, in some embodiments, Ar of Formula II is:

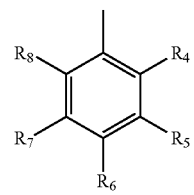

where $R_4$-$R_8$ are each independently selected from H; a halo (e.g., bromo, fluoro, chloro, iodo); a substituted or unsubstituted phenyl group; an aliphatic group, an alkyl group; a substituted alkyl group; an alkenyl group; an alkynyl group; a substituted or unsubstituted cyclic group; a substituted or unsubstituted heterocyclic group; a substituted or unsubstituted aryl group; and a substituted or unsubstituted heteroaryl group. In some embodiments, $R_4$ and $R_8$ are methyl groups, and $R_5$, $R_6$, and $R_7$ are H. In some embodiments, $R_4$ and $R_8$ are halogen groups (e.g., bromo, fluoro, chloro, iodo), and $R_5$, $R_6$, and $R_7$ are H.

In other embodiments, Ar of Formula II is a substituted or unsubstituted heterocyclic group, e.g., a substituted or unsubstituted pyridine, a thiazole, an imidazole, a thiophene, a quinoline, an isoquinoline, or a furan group. In some embodiments, Ar of Formula II is a substituted pyridinyl group, e.g., a dihalogeno-substituted pyridinyl group.

In some embodiments, a subject ALDH2 agonist is a compound of generic formula Ia, as shown below:

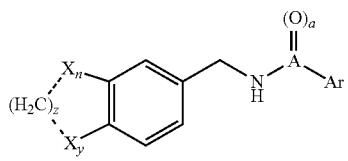

Formula Ia where $X_n$ and $X_y$ are each independently H, C, N, O, or a halogen (e.g., F, Br, Cl, or I);

where . . . (dotted line) is an optional bond;

where z is the integer 0, 1, or 2, with the provisos that: 1) z=0 when X=halogen and . . . is not a bond; and 2) when z=0, X=O, . . . is not a bond, and one or more oxygen atoms (X) are present, oxygen is attached to a methyl group;

where n is the integer 0 or 1;

where y is the integer 0 or 1;

where A=C or S, and where a=1 when A=C; and where a=2 when A=S;

where Ar is a phenyl or thiophene ring; wherein the Ar is optionally substituted at the position(s) ortho to the carbonyl or sulfonyl group by one or more substituents independently selected from methyl, halo, trifluoromethyl, or phenyl; wherein Ar is optionally substituted by a halogen meta or para to the carbonyl or sulfonyl group; and wherein, when Ar is a thiophene ring, the carbonyl or sulfonyl group is attached to a thiophene ring at the 2 or 3 position;

or a pro-drug, a pharmaceutically acceptable salt, an analog, or a derivative thereof.

In some embodiments, a subject ALDH2 agonist has the structure of Compound 1, as shown below.

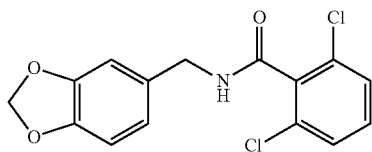

Compound 1: (N-(1,3-benzodioxol-5-ylmethyl)-2,6-dichlorobenzamide)

In some embodiments, a subject ALDH2 agonist has the structure of Compound 2, as shown below:

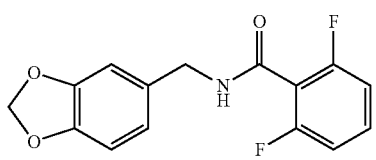

Compound 2: (N-(1,3-benzodioxol-5-ylmethyl)-2,6-difluorobenzamide)

In some embodiments, a subject ALDH2 agonist has the structure of Compound 3, as shown below.

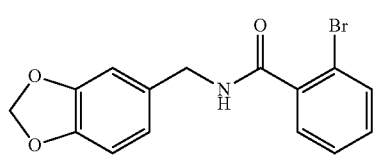

Compound 3: (N-(1,3-benzodioxol-5-ylmethyl)-2-bromobenzamide)

In some embodiments, one or more of Compound 1, Compound 2, and Compound 3 is specifically excluded.

In some embodiments, a subject ALDH2 agonist has the structure of Compound 4, as shown below.

Compound 4: (N-(1,3-benzodioxol-5-ylmethyl)-2-iodobenzamide)

In some embodiments, a subject ALDH2 agonist has the structure of one of the compounds designated XO-3, XO-4, XO-5, XO-9, XO-28, XO-29, XO-33, XO-36, XO-39, XO-12, XO-13, XO-6, XO-7, XO-8, XO-11, XO-22, XO-25, and XO-26, as shown below.

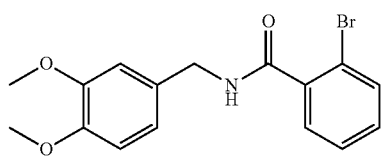

XO-3

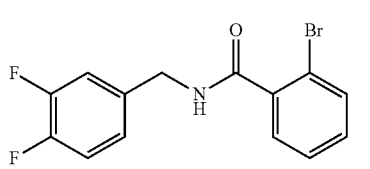

XO-4

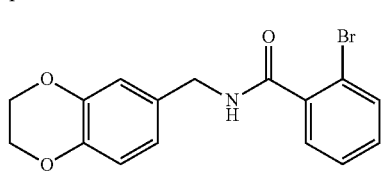

XO-5

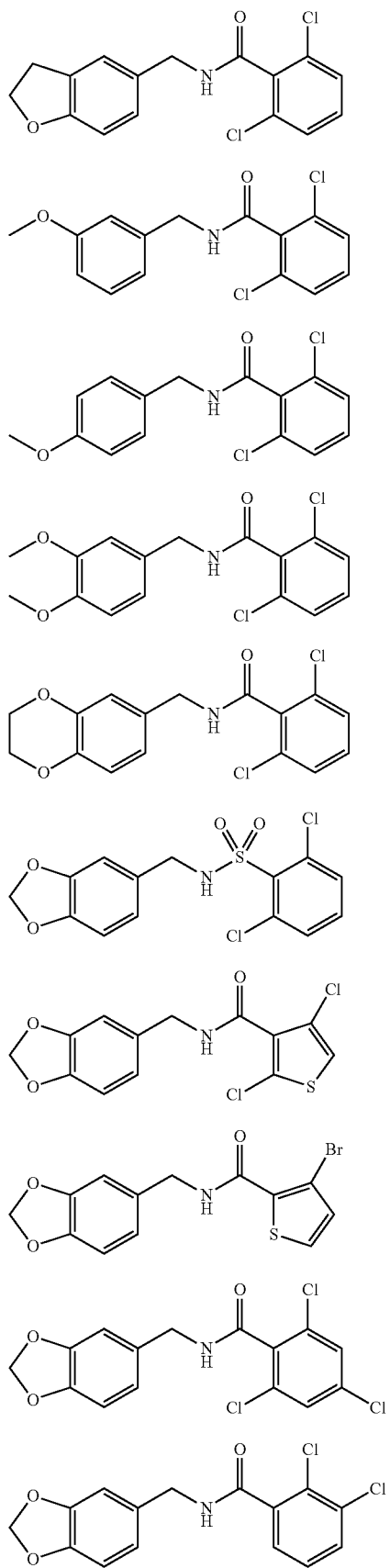
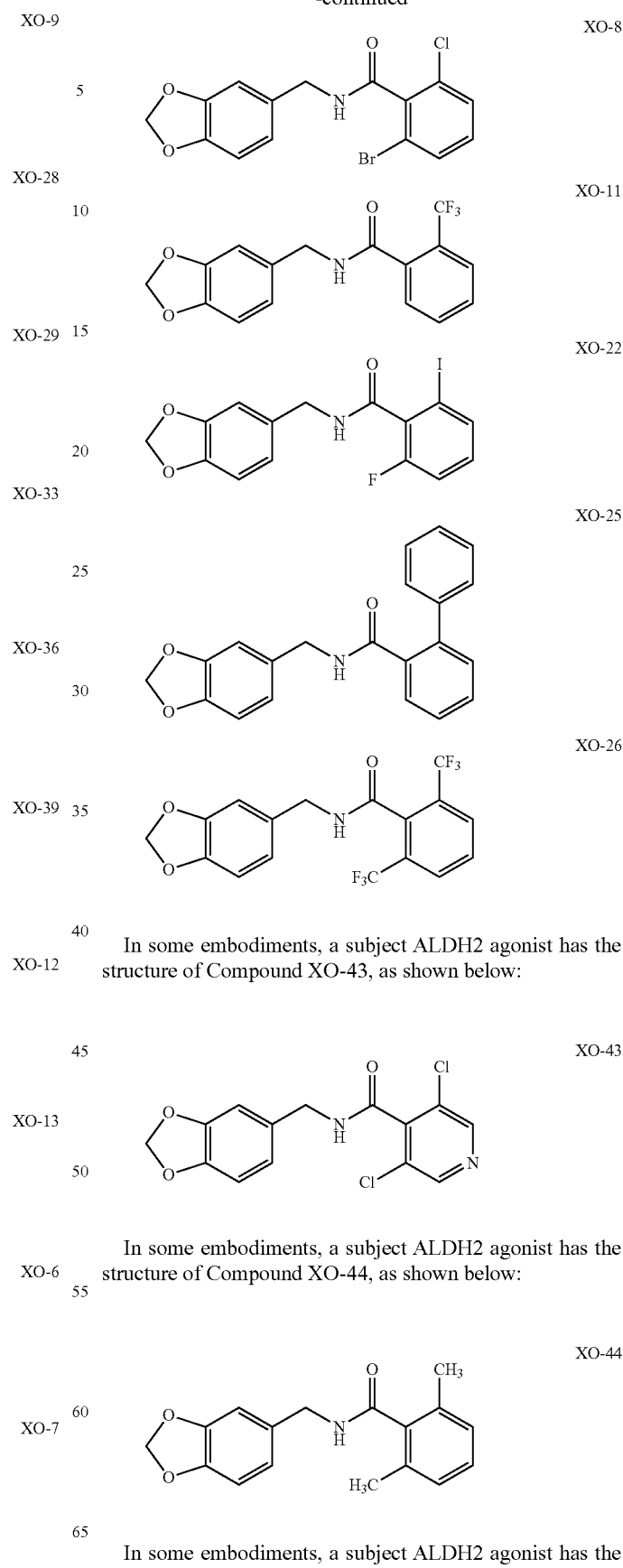
In some embodiments, a subject ALDH2 agonist has the structure of Compound XO-43, as shown below:
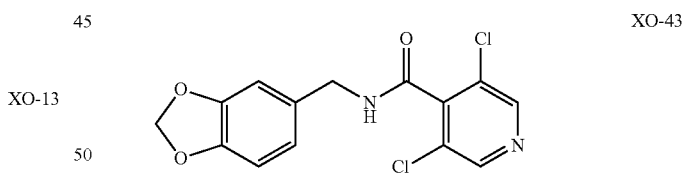
In some embodiments, a subject ALDH2 agonist has the structure of Compound XO-44, as shown below:
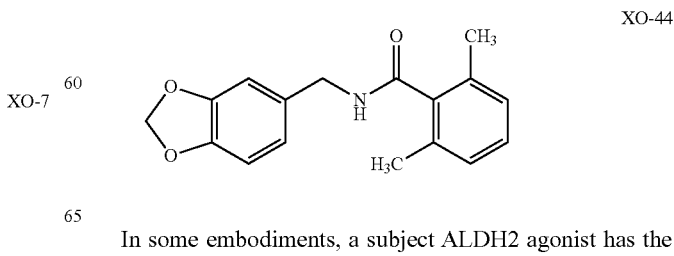
In some embodiments, a subject ALDH2 agonist has the structure of Compound XO-45, as shown below:

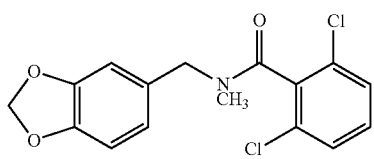

XO-45

In some embodiments, a subject ALDH2 agonist has the structure of Compound XO-46, as shown below:

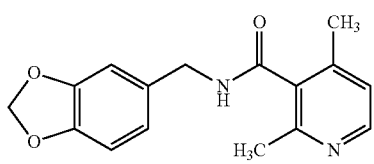

XO-46

Whether a compound is an ALDH2 agonist can be readily ascertained. Assays for dehydrogenase activity of ALDH2 are known in the art, and any known assay can be used. Examples of dehydrogenase assays are found in various publications, including, e.g., Sheikh et al. ((1997) *J. Biol. Chem.* 272: 18817-18822); Vallari and Pietruszko (1984) *J. Biol. Chem.* 259:4922; and Farres et al. ((1994) *J. Biol. Chem.* 269:13854-13860).

As an example of an assay for dehydrogenase activity, ALDH2 is assayed at 25° C. in 50 mM sodium pyrophosphate HCl buffer, pH 9.0, 100 mM sodium phosphate buffer, pH 7.4, or 50 mM sodium phosphate buffer, pH 7.4, where the buffer includes $NAD^+$ (e.g., 0.8 mM $NAD^+$, or higher, e.g., 1 mM, 2 mM, or 5 mM $NAD^+$) and an aldehyde substrate such as 14 μM propionaldehyde. Reduction of $NAD^+$ is monitored at 340 nm using a spectrophotometer, or by fluorescence increase using a fluoromicrophotometer. Enzymatic activity can be assayed using a standard spectrophotometric method, e.g., by measuring a reductive reaction of the oxidized form of nicotinamide adenine dinucleotide ($NAD^+$) to its reduced form, NADH, at 340 nm, as described in US 2005/0171043; and WO 2005/057213, and as depicted schematically in FIG. 2. In an exemplary assay, the reaction is carried out at 25° C. in 0.1 NaPPi buffer, pH 9.5, 2.4 mM $NAD^+$ and 10 mM acetaldehyde as the substrate. Enzymatic activity is measured by a reductive reaction of $NAD^+$ to NADH at 340 nm, as described in US 2005/0171043; and WO 2005/057213. Alternatively, the production of NADH can be coupled with another enzymatic reaction that consumes NADH and that provides for a detectable signal. An example of such an enzymatic reaction is a diaphorase-based reaction, which reduces resazurin to its oxidized fluorescent compound resorufin, as described in US 2005/0171043; and WO 2005/057213, and as depicted schematically in FIG. 2. Detection of fluorescent resorufin at 590 nm provides amplified and more sensitive signals for any change in ALDH2 enzymatic activity.

Whether a compound increases an esterase activity of ALDH2 can be determined using any known assay for esterase activity. For example, esterase activity of ALDH2 can be determined by monitoring the rate of p-nitrophenol formation at 400 nm in 25 mM N,N-Bis (2-hydroxyethyl)-2-amino ethanesulfonic acid (BES) (pH 7.5) with 800 μM p-nitrophenyl acetate as the substrate at room temperature in the absence or presence of added $NAD^+$. A pH-dependent molar extinction coefficient of 16 $mM^{-1}$ $cm^{-1}$ at 400 nm for nitrophenol can be used. See, e.g., Larson et al. (2007) *J. Biol. Chem.* 282:12940). Esterase activity of ALDH2 can be determined by measuring the rate of p-nitrophenol formation at 400 nm in 50 mM Pipes (pH 7.4) with 1 mM p-nitrophenylacetate as the substrate. A molar extinction coefficient of $18.3 \times 10^3$ $M^{-1}$ $cm^{-1}$ at 400 nm for p-nitrophenolate can be used for calculating its rate of formation. See, e.g., Ho et al. (2005) *Biochemistry* 44:8022).

Whether a compound increases a reductase activity of ALDH2 can be determined using any known assay for reductase activity. A reductase activity of ALDH2 can be determined by measuring the rate of 1,2-glyceryl dinitrate and 1,3-glyceryl dinitrate formation using a thin layer chromatography (TLC) or liquid scintillation spectrometry method, using a radioactively labeled substrate. For example, 0.1 mM or 1 mM GTN (glyceryl trinitrate) is incubated with the assay mixture (1 ml) containing 100 mM KPi (pH 7.5), 0.5 mM EDTA, 1 mM NADH, 1 mM NADPH in the presence ALDH2. After incubation at 37° C. for about 10 minutes to about 30 minutes, the reaction is stopped and GTN and its metabolites are extracted with 3×4 ml ether and pooled, and the solvent is evaporated by a stream of nitrogen. The final volume is kept to less than 100 ml in ethanol for subsequent TLC separation and scintillation counting. See, e.g., Zhang and Stamler (2002) *Proc. Natl. Acad. Sci. USA* 99:8306.

Another method for determining whether a compound increases enzymatic activity of an ALDH2 is described in more detail below, where the E487K ALDH2 variant is used.

ALDH2 Antagonists

The present invention provides ALDH2 antagonists (also referred to as "ALDH2 inhibitors"), and pharmaceutical compositions comprising ALDH2 antagonists. In some embodiments, ALDH2 antagonists are useful for treating alcohol addiction. In other embodiments, ALDH2 antagonists increase the sensitivity of a cancerous cell to a cancer chemotherapeutic agent. Thus, in some embodiments, ALDH2 antagonists are useful as adjuvants to standard cancer therapies, in the treatment of cancer.

In some embodiments, a subject ALDH2 antagonist reduces an enzymatic activity of an ALDH2 polypeptide by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, compared to the enzymatic activity of the ALDH2 polypeptide in the absence of the antagonist.

In some embodiments, a subject ALDH2 antagonist reduces a dehydrogenase activity of an ALDH2 polypeptide by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, compared to the dehydrogenase activity of the ALDH2 polypeptide in the absence of the antagonist.

In some embodiments, a subject ALDH2 antagonist reduces an esterase activity of an ALDH2 polypeptide by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, compared to the esterase activity of the ALDH2 polypeptide in the absence of the antagonist.

In some embodiments, a subject ALDH2 antagonist reduces a reductase activity of an ALDH2 polypeptide by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, compared to the reductase activity of the ALDH2 polypeptide in the absence of the antagonist.

In some embodiments, an ALDH2 antagonist reduces an enzymatic activity of an ALDH2 polypeptide comprising an amino acid sequence set forth in SEQ ID NO:1 (depicted in FIG. 1A), or as set forth in amino acids 18-517 of SEQ ID NO:1, by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, when compared to the enzymatic activity of the ALDH2 polypeptide in the absence of the antagonist.

In some embodiments, an ALDH2 antagonist reduces a dehydrogenase activity of an ALDH2 polypeptide comprising an amino acid sequence set forth in SEQ ID NO:1 (depicted in FIG. 1A), or as set forth in amino acids 18-517 of SEQ ID NO:1, by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, when compared to the dehydrogenase activity of the ALDH2 polypeptide in the absence of the antagonist.

In some embodiments, an ALDH2 antagonist reduces an esterase activity of an ALDH2 polypeptide comprising an amino acid sequence set forth in SEQ ID NO:1 (depicted in FIG. 1A), or as set forth in amino acids 18-517 of SEQ ID NO:1, by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, when compared to the esterase activity of the ALDH2 polypeptide in the absence of the antagonist.

In some embodiments, an ALDH2 antagonist reduces a reductase activity of an ALDH2 polypeptide comprising an amino acid sequence set forth in SEQ ID NO:1 (depicted in FIG. 1A), or as set forth in amino acids 18-517 of SEQ ID NO:1, by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, or at least about 90%, when compared to the reductase activity of the ALDH2 polypeptide in the absence of the antagonist.

In some embodiments, a subject ALDH2 antagonist is specific for (e.g., selective for) ALDH2, e.g., a subject ALDH2 antagonist reduces the enzymatic activity of an ALDH2 enzyme, but does not substantially reduce the enzymatic activity of cytosolic aldehyde dehydrogenase-1 (ALDH1), e.g., a subject ALDH2 antagonist reduces the enzymatic activity of an ALDH1 enzyme, if at all, by less than about 10%, less than about 5%, less than about 2%, or less than about 1%, when used at a concentration that reduces the enzymatic activity of an ALDH2 enzyme by at least about 10% or more. In some embodiments, a subject ALDH2 antagonist does not substantially reduce the enzymatic activity of alcohol dehydrogenase (ADH), e.g., a subject ALDH2 antagonist reduces the enzymatic activity of an ADH, if at all, by less than about 10%, less than about 5%, less than about 2%, or less than about 1%, when used at a concentration that reduces the enzymatic activity of an ALDH2 enzyme by at least about 10% or more.

For example, in some embodiments, a subject ALDH2 antagonist is specific for (e.g., selective for) ALDH2, e.g., a subject ALDH2 antagonist reduces a dehydrogenase activity of an ALDH2 enzyme, but does not substantially reduce the dehydrogenase activity of cytosolic aldehyde dehydrogenase-1 (ALDH1), e.g., a subject ALDH2 antagonist reduces the dehydrogenase activity of an ALDH1 enzyme, if at all, by less than about 10%, less than about 5%, less than about 2%, or less than about 1%, when used at a concentration that reduces the dehydrogenase activity of an ALDH2 enzyme by at least about 10% or more. In some embodiments, a subject ALDH2 antagonist does not substantially reduce the dehydrogenase activity of alcohol dehydrogenase (ADH), e.g., a subject ALDH2 antagonist reduces the dehydrogenase activity of an ADH, if at all, by less than about 10%, less than about 5%, less than about 2%, or less than about 1%, when used at a concentration that reduces the dehydrogenase activity of an ALDH2 enzyme by at least about 10% or more.

In some embodiments, a subject ALDH2 antagonist has an $IC_{50}$ of less than 50 μM, e.g., a subject ALDH2 antagonist has an $IC_{50}$ of from about 50 μM to about 5 nm, or less than 5 nM. For example, in some embodiments, a subject ALDH2 antagonist has an $IC_{50}$ of from about 50 μM to about 25 μM, from about 25 μM to about 10 μM, from about 10 μM to about 5 μM, from about 5 μM to about from about 1 μM to about 500 nM, from about 500 nM to about 400 nM, from about 400 nM to about 300 nM, from about 300 nM to about 250 nM, from about 250 nM to about 200 nM, from about 200 nM to about 150 nM, from about 150 nM to about 100 nM, from about 100 nM to about 50 nM, from about 50 nM to about 30 nM, from about 30 nM to about 25 nM, from about 25 nM to about 20 nM, from about 20 nM to about 15 nM, from about 15 nM to about 10 nM, from about 10 nM to about 5 nM, or less than about 5 nM.

For example, in some embodiments, a subject ALDH2 antagonist has an $IC_{50}$ of less than 50 μM, e.g., a subject ALDH2 antagonist has an $IC_{50}$ of from about 50 μM to about 5 nm, or less than 5 nM. For example, in some embodiments, a subject ALDH2 antagonist has an $IC_{50}$ of from about 50 μM to about 25 μM, from about 25 μM to about 10 μM, from about 10 μM to about 5 μM, from about 5 μM to about from about 1 μM to about 500 nM, from about 500 nM to about 400 nM, from about 400 nM to about 300 nM, from about 300 nM to about 250 nM, from about 250 nM to about 200 nM, from about 200 nM to about 150 nM, from about 150 nM to about 100 nM, from about 100 nM to about 50 nM, from about 50 nM to about 30 nM, from about 30 nM to about 25 nM, from about 25 nM to about 20 nM, from about 20 nM to about 15 nM, from about 15 nM to about 10 nM, from about 10 nM to about 5 nM, or less than about 5 nM, for a dehydrogenase activity of mitochondrial ALDH2.

In some embodiments, a subject ALDH2 agonist has an $IC_{50}$ for an ALDH2 polypeptide comprising an amino acid sequence set forth in SEQ ID NO:1 (depicted in FIG. 1A), or as set forth in amino acids 18-517 of SEQ ID NO:1, of from about 50 μM to about 25 μM, from about 25 μM to about 10 μM, from about 10 μM to about 5 μM, from about 5 μM to about from about 1 μM to about 500 nM, from about 500 nM to about 400 nM, from about 400 nM to about 300 nM, from about 300 nM to about 250 nM, from about 250 nM to about 200 nM, from about 200 nM to about 150 nM, from about 150 nM to about 100 nM, from about 100 nM to about 50 nM, from about 50 nM to about 30 nM, from about 30 nM to about 25 nM, from about 25 nM to about 20 nM, from about 20 nM to about 15 nM, from about 15 nM to about 10 nM, from about 10 nM to about 5 nM, or less than about 5 nM.

In some embodiments, a subject ALDH2 agonist has an IC$_{50}$ for a dehydrogenase activity of an ALDH2 polypeptide comprising an amino acid sequence set forth in SEQ ID NO:1 (depicted in FIG. 1A), or as set forth in amino acids 18-517 of SEQ ID NO:1, of from about 50 µM to about 25 µM, from about 25 µM to about 10 µM, from about 10 µM to about 5 µM, from about 5 µM to about 1 µM, from about 1 µM to about 500 nM, from about 500 nM to about 400 nM, from about 400 nM to about 300 nM, from about 300 nM to about 250 nM, from about 250 nM to about 200 nM, from about 200 nM to about 150 nM, from about 150 nM to about 100 nM, from about 100 nM to about 50 nM, from about 50 nM to about 30 nM, from about 30 nM to about 25 nM, from about 25 nM to about 20 nM, from about 20 nM to about 15 nM, from about 15 nM to about 10 nM, from about 10 nM to about 5 nM, or less than about 5 nM.

In some embodiments, a subject ALDH2 antagonist is a compound of generic Formula III, as shown below:

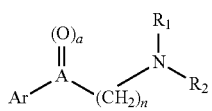

Formula III where Ar is an unsubstituted or substituted phenyl group;

where n=0, 1, 2, or 3;

where A=C or S, and where a=1 when A=C; and where a=2 when A=S; and where R$_1$ and R$_2$ are independently H; a halo; a substituted or unsubstituted phenyl group; an amide, an aliphatic group, an alkyl group; a substituted alkyl group; an alkenyl group; an alkynyl group; a substituted or unsubstituted cyclic group; a substituted or unsubstituted heterocyclic group; a substituted or unsubstituted aryl group; and a substituted or unsubstituted heteroaryl group;

or a pro-drug, a pharmaceutically acceptable salt, an analog, or a derivative thereof.

In some embodiments, a subject ALDH2 antagonist is a compound of generic Formula IV, as shown below:

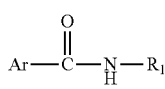

Formula IV where Ar is a substituted or unsubstituted phenyl or pyridyl group; and where R$_1$ is selected from H; a halo (e.g., bromo, fluoro, chloro, iodo); a substituted or unsubstituted phenyl group; an amide, an aliphatic group, an alkyl group; a substituted alkyl group; an alkenyl group; an alkynyl group; a substituted or unsubstituted cyclic group; a substituted or unsubstituted heterocyclic group; a substituted or unsubstituted aryl group; and a substituted or unsubstituted heteroaryl group;

or a pro-drug, a pharmaceutically acceptable salt, an analog, or a derivative thereof.

In some embodiments, R$_1$ of Formula IV is selected from:

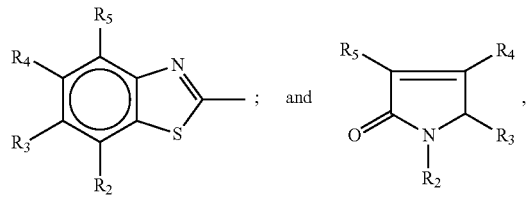

where each of R$_2$, R$_3$, R$_4$, and R$_5$ is independently selected from H; a halo (e.g., bromo, fluoro, chloro, iodo); an amide; a substituted or unsubstituted phenyl group; an aliphatic group, an alkyl group; a substituted alkyl group; an alkenyl group; an alkynyl group; a substituted or unsubstituted cyclic group; a substituted or unsubstituted heterocyclic group; a substituted or unsubstituted aryl group; and a substituted or unsubstituted heteroaryl group.

In some embodiments, a subject ALDH2 antagonist is a compound of generic Formula V, as shown below:

(Formula V)

where n is an integer from 0 to 20 (e.g., 0, 1, 2, 2, 3, 4, 5-10, 10-15, or 15-20);

where Ar is an unsubstituted or substituted phenyl, naphthyl, or pyridyl;

where R$_1$H; a halo (e.g., bromo, fluoro, chloro, iodo); an amide; a substituted or unsubstituted phenyl group; an aliphatic group, an alkyl group; a substituted alkyl group; an alkenyl group; an alkynyl group; a substituted or unsubstituted cyclic group; a substituted or unsubstituted heterocyclic group; a substituted or unsubstituted aryl group; and a substituted or unsubstituted heteroaryl group;

where Z is H; a halo (e.g., bromo, fluoro, chloro, iodo); an amide; a substituted or unsubstituted phenyl group; an aliphatic group, an alkyl group; a substituted alkyl group; an alkenyl group; an alkynyl group; a substituted or unsubstituted cyclic group; a substituted or unsubstituted heterocyclic group; a substituted or unsubstituted aryl group; and a substituted or unsubstituted heteroaryl group;

or a pro-drug, a pharmaceutically acceptable salt, an analog, or a derivative thereof.

In some embodiments, Z of Formula V is selected from:

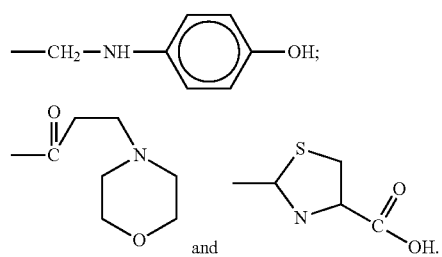

In some embodiments, a subject ALDH2 antagonist is a compound of generic Formula VI, as shown below:

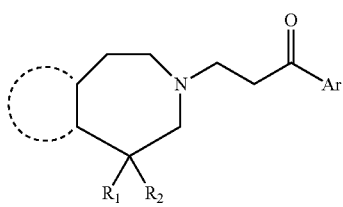

(Formula VI)

where Ar is a substituted or unsubstituted phenyl or benzodioxaryl;

where $R_1$ and $R_2$ are independently H; a halo (e.g., bromo, fluoro, chloro, iodo); an amide; a substituted or unsubstituted phenyl group; an aliphatic group, an alkyl group; a substituted alkyl group; an alkenyl group; an alkynyl group; a substituted or unsubstituted cyclic group; a substituted or unsubstituted heterocyclic group; a substituted or unsubstituted aryl group; and a substituted or unsubstituted heteroaryl group;

where the dotted line is an optional benzene ring which may be substituted or unsubstituted;

or a pro-drug, a pharmaceutically acceptable salt, an analog, or a derivative thereof.

In some embodiments, a subject ALDH2 antagonist is a compound of generic Formula VII, as shown below:

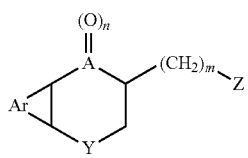

Formula VII wherein:
Ar=substituted or unsubstituted aryl group;
Z=substituted or unsubstituted heterocyclic group;
Y=C, O, N, or S;
A=C or S, wherein when A=C, n=1, and wherein when A=S, n=2; and
m=an integer from 0 to 20 (e.g., 0, 1, 2, 3, 4, 5, 5-10, 10-15, or 15-20), or a pro-drug, a pharmaceutically acceptable salt, an analog, or a derivative thereof.

In some embodiments, a subject ALDH2 antagonist is a compound of generic Formula VIIa, as shown below:

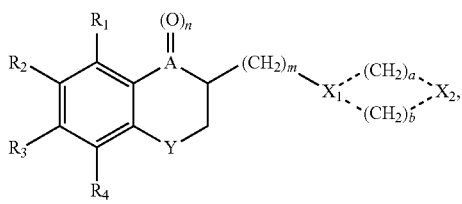

Formula VIIa wherein:
Y=C, O, N, or S;
A=C or S, wherein when A=C, n=1, and wherein when A=S, n=2;
m=0, 1, 2, or 3;
each of $R_1$, $R_2$, $R_3$, and $R_4$ is independently selected from H, halogen, alkyl group, substituted alkyl group, alkenyl group, alkynyl group, hydroxyl, —$CF_3$, —$OCF_3$, —$NO_2$, substituted or unsubstituted amine, substituted or unsubstituted amide, substituted or unsubstituted cyclic group, substituted or unsubstituted heterocyclic group, substituted or unsubstituted aryl group, or substituted or unsubstituted heteroaryl group; and $X_1$ and $X_2$ are each independently C, N, O, or S, wherein a is 0, 1, 2, 3, or 4, and wherein b is 0, 1, 2, 3, or 4, or a pro-drug, a pharmaceutically acceptable salt, an analog, or a derivative thereof.

In some embodiments, a subject ALDH2 antagonist is Compound 5 (referred to in FIG. 9 as Compound 62923), as shown below:

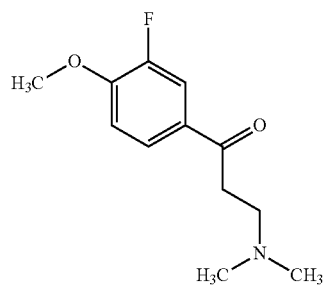

Compound 5

In some embodiments, a subject ALDH2 antagonist is Compound 6 (referred to in FIG. 9 as Compound 46072), as shown below:

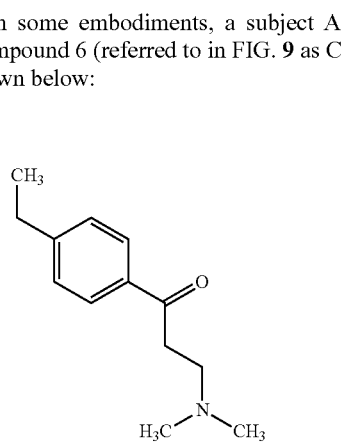

Compound 6

In some embodiments, a subject ALDH2 antagonist is Compound 7 (referred to in FIG. 10 as Compound 32208), as shown below:

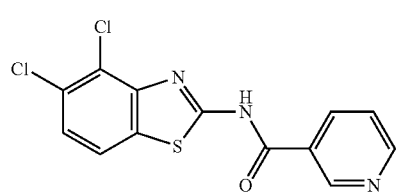

Compound 7

In some embodiments, a subject ALDH2 antagonist is selected from Compounds 8-18, as shown below:

(Compound 8)

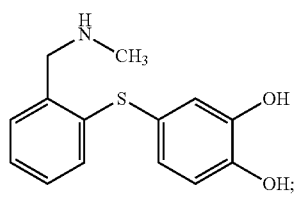

(Compound 9)

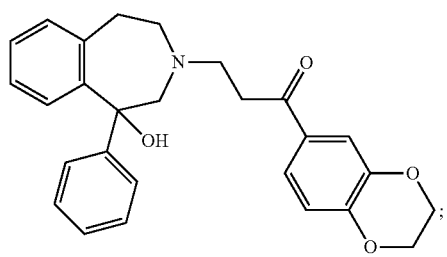

(Compound 10)

(Compound 11)

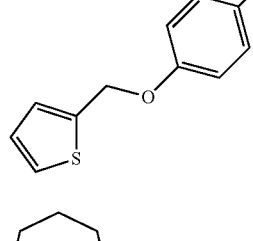

(Compound 12)

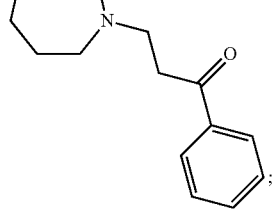

(Compound 13)

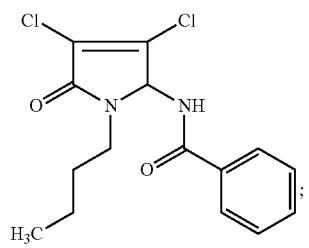

-continued (Compound 14)

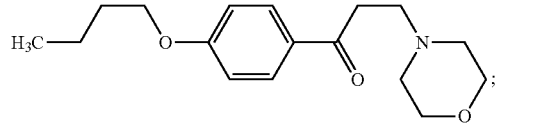

(Compound 15)

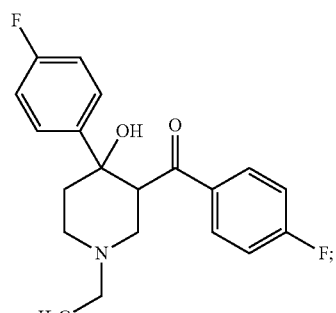

(Compound 16)

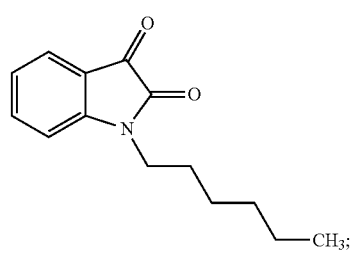

(Compound 17)

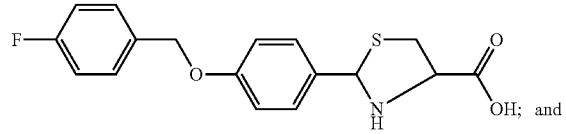

(Compound 18)

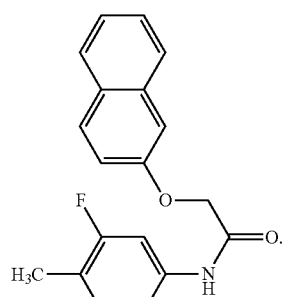

Whether a compound is an ALDH2 antagonist can be readily ascertained. Assays for ALDH2 are known in the art, and any known assay can be used. Examples of assays are found in various publications, including, e.g., Sheikh et al. ((1997) *J. Biol. Chem.* 272:18817-18822) and Farres et al. ((1994) *J. Biol. Chem.* 269:13854-13860). For example, ALDH2 is assayed at 25° C. in 50 mM sodium pyrophosphate HCl buffer, pH 9.0, 100 mM sodium phosphate buffer, pH 7.4, or 50 mM sodium phosphate buffer, pH 7.4, where the buffer includes NAD (e.g., 0.8 mM NAD$^+$, or higher, e.g., 1 mM, 2 mM, or 5 mM NAD$^+$) and a substrate such as 14 μM propionaldehyde. Reduction of NAD$^+$ is monitored at 340 nm using a spectrophotometer, or by fluorescence increase using a fluoromicrophotometer. Enzymatic activity can be assayed using a standard spectrophotometric method, e.g., by measuring a reductive reaction of the oxidized form of nicotinamide adenine dinucleotide (NAD$^+$) to its reduced form, NADH, at 340 nm, as described in US 2005/0171043; and WO 2005/057213. In an exemplary assay, the reaction is carried out at 25° C. in 0.1 NaPPi buffer, pH 9.5, 2.4 mM NAD$^+$ and 10 mM acetaldehyde as the substrate. Enzymatic activity is measured by a reductive reaction of NAD$^+$ to NADH at 340 nm, as described in US 2005/0171043; and WO 2005/057213. Alternatively, the production of NADH can be coupled with another enzymatic reaction that consumes NADH and that provides for a detectable signal. An example of such an enzymatic reaction is a diaphorase-based reaction, which reduces resazurin to its oxidized fluorescent compound resorufin, as described in US 2005/0171043; and WO 2005/057213. Detection of fluorescent resorufin at 590 nm provides amplified and more sensitive signals for any change in ALDH2 enzymatic activity.

Pharmaceutical Compositions, Dosages, Routes of Administration

The present invention provides pharmaceutical compositions comprising a subject ALDH2 agonist. The present invention provides pharmaceutical compositions comprising a subject ALDH2 antagonist. The terms "ALDH2 agonist" and "ALDH2 antagonist" are referred to collectively herein as "ALDH2 activity modulator" or "active agent." A subject ALDH2 activity modulator is formulated with one or more pharmaceutically acceptable excipients. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7$^{th}$ ed., Lippincott, Williams, & Wilkins; and Handbook of Pharmaceutical Excipients (2000) A. H. Kibbe et al., eds., 3$^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public In the subject methods, a subject ALDH2 activity modulator may be administered to the host using any convenient means capable of resulting in the desired reduction in autoimmune disease. Thus, a subject ALDH2 activity modulator can be incorporated into a variety of formulations for therapeutic administration. More particularly, a subject ALDH2 activity modulator can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, a subject active agent may be administered in the form of their pharmaceutically acceptable salts, or a subject active agent may be used alone or in appropriate association, as well as in combination, with other pharmaceutically active compounds. The following methods and excipients are merely exemplary and are in no way limiting.

For oral preparations, a subject active agent can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

A subject active agent can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

A subject active agent can be utilized in aerosol formulation to be administered via inhalation. A subject active agent can be formulated into pressurized acceptable propellants such as dichlorodifluoromethane, propane, nitrogen and the like.

Furthermore, a subject active agent can be made into suppositories by mixing with a variety of bases such as emulsifying bases or water-soluble bases. An active agent can be administered rectally via a suppository. The suppository can include vehicles such as cocoa butter, carbowaxes and polyethylene glycol monomethyl ethers, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the subject active agent. Similarly, unit dosage forms for injection or intravenous administration may comprise a subject active agent in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of a subject active agent calculated in an amount sufficient to produce the desired effect in association with a pharmaceutically acceptable diluent, carrier or vehicle. The specifications for a subject active agent depend on the particular compound employed and the effect to be achieved, and the pharmacodynamics associated with each compound in the host.

A subject active agent can be formulated for administration by injection. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

In some embodiments, a subject active agent is delivered by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with the present invention. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, delivery of active agent can be accomplished using any of a variety of refillable, pump systems. Pumps provide consistent, controlled release over time. In some embodiments, the agent is in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to a subdermal, subcutaneous, intramuscular, or other suitable site within a subject's body. Subcutaneous implantation sites are used in some embodiments because of convenience in implantation and removal of the drug delivery device.

Drug release devices suitable for use in the invention may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, etc.

Drug release devices based upon a mechanical or electromechanical infusion pump can also be suitable for use with the present invention. Examples of such devices include those described in, for example, U.S. Pat. Nos. 4,692,147; 4,360,019; 4,487,603; 4,360,019; 4,725,852, and the like. In general, a subject treatment method can be accomplished using any of a variety of refillable, non-exchangeable pump systems. Pumps and other convective systems are generally preferred due to their generally more consistent, controlled release over time. Osmotic pumps are used in some embodiments due to their combined advantages of more consistent controlled release and relatively small size (see, e.g., PCT published application no. WO 97/27840 and U.S. Pat. Nos. 5,985,305 and 5,728,396)). Exemplary osmotically-driven devices suitable for use in the invention include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

In some embodiments, the drug delivery device is an implantable device. The drug delivery device can be implanted at any suitable implantation site using methods and devices well known in the art. As noted infra, an implantation site is a site within the body of a subject at which a drug delivery device is introduced and positioned. Implantation sites include, but are not necessarily limited to a subdermal, subcutaneous, intramuscular, or other suitable site within a subject's body.

In some embodiments, an active agent is delivered using an implantable drug delivery system, e.g., a system that is programmable to provide for administration of a subject active agent. Exemplary programmable, implantable systems include implantable infusion pumps. Exemplary implantable infusion pumps, or devices useful in connection with such pumps, are described in, for example, U.S. Pat. Nos. 4,350,155; 5,443,450; 5,814,019; 5,976,109; 6,017,328; 6,171,276; 6,241,704; 6,464,687; 6,475,180; and 6,512,954. A further exemplary device that can be adapted for the present invention is the Synchromed infusion pump (Medtronic).

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

Dosages and Dosing

Depending on the subject and condition being treated and on the administration route, the subject compounds may be administered in dosages of, for example, 0.1 µg to 10 mg/kg body weight per day. The range is broad, since in general the efficacy of a therapeutic effect for different mammals varies widely with doses typically being 20, 30 or even 40 times smaller (per unit body weight) in man than in the rat. Similarly the mode of administration can have a large effect on dosage. Thus, for example, oral dosages may be about ten times the injection dose. Higher doses may be used for localized routes of delivery.

For example, a subject ALDH2 activity modulator can be administered in an amount of from about 1 mg to about 1000 mg per dose, e.g., from about 1 mg to about 5 mg, from about 5 mg to about 10 mg, from about 10 mg to about 20 mg, from about 20 mg to about 25 mg, from about 25 mg to about 50 mg, from about 50 mg to about 75 mg, from about 75 mg to about 100 mg, from about 100 mg to about 125 mg, from about 125 mg to about 150 mg, from about 150 mg to about 175 mg, from about 175 mg to about 200 mg, from about 200 mg to about 225 mg, from about 225 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 750 mg, or from about 750 mg to about 1000 mg per dose.

An exemplary dosage may be a solution suitable for intravenous administration; a tablet taken from two to six times daily, or one time-release capsule or tablet taken once a day and containing a proportionally higher content of active ingredient, etc. The time-release effect may be obtained by capsule materials that dissolve at different pH values, by capsules that release slowly by osmotic pressure, or by any other known means of controlled release.

Those of skill in the art will readily appreciate that dose levels can vary as a function of the specific compound, the severity of the symptoms and the susceptibility of the subject to side effects. Preferred dosages for a given compound are readily determinable by those of skill in the art by a variety of means.

Although the dosage used will vary depending on the clinical goals to be achieved, a suitable dosage range is in some embodiments one which provides up to about 1 µg to about 1,000 µg or about 10,000 µg of subject compound in a blood sample taken from the individual being treated, about 24 hours after administration of the compound to the individual.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the invention. Similarly, unit dosage forms for injection or intravenous administration may comprise the compound (s) in a composition as a solution in sterile water, normal saline or another pharmaceutically acceptable carrier.

In some embodiments, multiple doses of a subject compound are administered. The frequency of administration of a subject compound can vary depending on any of a variety of factors, e.g., severity of the symptoms, etc. For example, in some embodiments, a subject compound is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid). As discussed above, in some embodiments, a subject compound is administered continuously.

The duration of administration of a subject compound, e.g., the period of time over which a subject compound is administered, can vary, depending on any of a variety of factors, e.g., patient response, etc. For example, a subject compound can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more. In some embodiments, a subject compound is administered for the lifetime of the individual.

Routes of Administration

A subject ALDH2 activity modulator is administered to an individual using any available method and route suitable for drug delivery, including in vivo and ex vivo methods, as well as systemic and localized routes of administration. Administration can be acute (e.g., of short duration, e.g., a single administration, administration for one day to one week), or chronic (e.g., of long duration, e.g., administration for longer than one week, e.g., administration over a period of time of from about 2 weeks to about one month, from about one month to about 3 months, from about 3 months to about 6 months, from about 6 months to about 1 year, or longer than one year).

Conventional and pharmaceutically acceptable routes of administration include intranasal, intramuscular, intratracheal, subcutaneous, intradermal, transdermal, sublingual, topical application, intravenous, rectal, nasal, oral, and other enteral and parenteral routes of administration. Routes of administration may be combined, if desired, or adjusted depending upon the agent and/or the desired effect. The compound can be administered in a single dose or in multiple doses.

An active agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

The agent can also be delivered to the subject by enteral administration. Enteral routes of administration include, but are not necessarily limited to, oral and rectal (e.g., using a suppository) delivery.

Methods of administration of the agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

Treatment Methods

The present invention provides various treatment methods, generally involving administering to an individual in need thereof an effective amount of a subject agonist, or an effective amount of a subject antagonist. A subject ALDH2 agonist is suitable for treating a variety of disorders, including, e.g., conditions involving ischemic stress, chronic free-radical associated diseases, acute free-radical associated diseases, insensitivity to nitroglycerin (e.g., in angina and heart failure), hypertension, diabetes, and osteoporosis. A subject ALDH2 antagonist is suitable for sensitizing a cancerous cell to a cancer chemotherapeutic agent or other standard cancer therapy; for treating alcohol (e.g., ethanol; ethyl alcohol) addiction; and for treating narcotic addiction.

Methods of Treating Conditions Involving Ischemic Stress

The present invention provides methods for treating conditions involving ischemic stress, including prophylactic methods, in an individual, the methods generally involving administering to an individual in need thereof an effective amount of a subject ALDH2 agonist. Conditions involving ischemic stress include ischemic conditions, ischemic events, conditions that can give rise to ischemia, and conditions that result from an ischemic event. Conditions involving ischemic stress that are amenable to treatment with a subject method include ischemia that result from any condition or event, including, but not limited to, myocardial infarct (e.g., acute myocardial infarction), cardiac surgery, brain trauma, cerebrovascular disease, stroke, spinal cord injury, subarachnoid hemorrhage, major surgery in which ischemia to variety of organs occur, organ transplantation, limb ischemia (e.g., resulting from Type 1 or Type 2 diabetes), and the like.

In some embodiments, the agent is administered before a predicted or anticipated ischemic event, e.g., from about 1 hour to about 1 week before the ischemic event, e.g., from about 1 hour to about 2 hours, from about 2 hours to about 4 hours, from about 4 hours to about 8 hours, from about 8 hours to about 12 hours, from about 12 hours to about 16 hours, from about 16 hours to about 24 hours, from about 24 hours to about 36 hours, from about 36 hours to about 48 hours, from about 48 hours to about 72 hours, or from about 72 hours to about 1 week preceding the predicted or anticipated ischemic event.

Pretreatment with an active agent is desirable under certain circumstances, for example, when a subject has already experienced a stroke, when a subject is about to undergo cardiac surgery, etc. For example, a patient who has already experienced a stroke will have an increased probability of experiencing a second stroke. Subjects who are susceptible to transient ischemic attacks also have an increased risk of a stroke. Subjects who suffer a subarachnoid hemorrhage may experience further ischemic events induced by vasospasms that constrict the blood vessels. Subjects who experience trauma to organs such as the brain are also susceptible to an ischemic event. Subjects undergoing surgery over an extended period of time are also susceptible to an ischemic event. The above situations exemplify circumstances when a subject would benefit from pretreatment with a subject ALDH2 agonist.

In some embodiments, a subject ALDH2 agonist is administered after an ischemic event. For example, a subject ALDH2 agonist is effective in reducing the adverse effects of an ischemic event such as cardiac ischemia, reperfusion injury, cerebrovascular disease, acute myocardial infarction, subarachnoid hemorrhage, and trauma. In some embodiments, a subject ALDH2 agonist is administered within 1 minute to within 15 hours, e.g., from about 1 minute to about 5 minutes, from about 5 minutes to about 10 minutes, from about 10 minutes to about 15 minutes, from about 15 minutes to about 30 minutes, from about 30 minutes to about 60 minutes, from about 60 minutes to about 2 hours, from about 2 hours to about 4 hours, from about 4 hours to about 8 hours, from about 8 hours to about 12 hours, or from about 12 hours to about 15 hours, following the ischemic event. In some embodiments, an increased concentration of a subject ALDH2 agonist is maintained in the plasma for at least several hours to several days following the ischemic event.

For example, in some embodiments, a subject ALDH2 agonist is administered to an individual who has suffered an acute myocardial infarction (AMI) within 1 minute to within 15 hours, e.g., from about 1 minute to about 5 minutes, from about 5 minutes to about 10 minutes, from about 10 minutes to about 15 minutes, from about 15 minutes to about 30 minutes, from about 30 minutes to about 60 minutes, from about 60 minutes to about 2 hours, from about 2 hours to about 4 hours, from about 4 hours to about 8 hours, from about 8 hours to about 12 hours, or from about 12 hours to about 15 hours, following the AMI.

Methods of Treating Chronic and Acute Free-Radical Associated Diseases

The present invention provides methods for treating acute and chronic free-radical associated diseases in an individual, the methods generally involving administering to an individual in need thereof an effective amount of a subject ALDH2 agonist.

Acute Free-Radical Associated Disorders

The present invention provides methods for treating acute free-radical associated diseases in an individual, the methods generally involving administering to an individual in need thereof an effective amount of a subject ALDH2 agonist. Acute free radical-associated disorders that are amenable to treatment with a subject method include seizures (Patel et al. (2001) *Journal of Neurochemistry* 79:1065-1069); skin damage resulting from UV exposure, and photodamage of skin (e.g., "sunburn") (Aldini et al. (2007) *Chem Res Toxicol.* 20(3):416-23); acute thermal skin burn injury (Pintaudi et al. (2000) *Free Radic Res.* 33(2):139-46); and tissue hyperoxia (e.g., hyperoxia-induced chronic lung disease; and bronchopulmonary dysplasia) (Xu et al. (2006) *Am J Physiol Lung Cell Mol. Physiol.* 291(5):L966-75).

The present invention provides methods for treating sunburn in an individual, the methods generally involving administering to an individual in need thereof an effective amount of a subject ALDH2 agonist. In some embodiments, a subject method for treating sunburn comprises topically applying a formulation comprising a subject ALDH2 agonist to an area of the skin affected by sunburn.

The present invention provides methods for treating a seizure in an individual, the methods generally involving administering to an individual in need thereof an effective amount of a subject ALDH2 agonist. In some embodiments, a subject ALDH2 agonist is administered after a seizure has occurred, e.g., within from about 1 minute to about 5 minutes, from about 5 minutes to about 15 minutes, from about 15 minutes to about 30 minutes, from about 30 minutes to about 1 hour, or from about 1 hour to about 4 hours following a seizure. In other embodiments, a subject ALDH2 agonist is administered prophylactically, e.g., a subject ALDH2 agonist is administered to an individual who has experienced a seizure in the past, to reduce the likelihood that another seizure will occur. In some embodiments, an effective amount of a subject ALDH2 agonist is an amount that is effective to reduce at least one of the severity of a seizure, the frequency of seizures, and the duration of a seizure.

Chronic Free-Radical Associated Diseases

The present invention provides methods for treating chronic free-radical associated diseases in an individual, the methods generally involving administering to an individual in need thereof an effective amount of a subject ALDH2 agonist. Chronic free radical-associated disorders that are amenable to treatment with a subject method include neurodegenerative diseases such as Parkinson's Disease and Alzheimer's Disease (Burke et al. (2003) *Neurol. Dis.* 2(2):143; and Ohta and Ohsawa (2006) *J. Alzheimer's Disease* 9(2):155); amyotrophic lateral sclerosis (ALS); cancer such as esophageal cancer (Chen et al. (2006) *Int J Cancer* 2119(12):2827-31); upper aerodigestive tract cancer (Hashibe et al. (2006) *Cancer Epidemiol Biomarkers Prev.* 15(4):696-703); head and neck squamous cell carcinoma (Hashimoto et al. (2006) *Tumour Biol.* 27(6):334-8; Yokoyama et al. (2005) *Alcohol.* 35(3):175-85); cardiovascular diseases such as atherosclerosis (Narita et al. (2003) *Ultrasound in Medicine and Biology* 29(10):1415-1419); and the like. In some embodiments, a chronic free radical-associated disease is treated by chronic (e.g., daily) treatment with a subject ALDH2 agonist.

The present invention provides a method for treating Alzheimer's Disease (AD) in an individual suffering from AD, the method generally involving administering to the individual an effective amount of a subject ALDH2 agonist. In some embodiments, an "effective amount" of a subject ALDH2 agonist is an amount that is effective to at least slow the decline in cognitive function in the individual. In some embodiments, an "effective amount" of a subject ALDH2 agonist is an amount that is effective to improve memory in the individual being treated. In some embodiments, a subject ALDH2 agonist is administered to the individual systemically, over a period of time of from about 3 months to about 6 months, from about 6 months to about 1 year, or more than 1 year.

The present invention provides a method for treating Parkinson's Disease in an individual, the method generally involving administering to the individual an effective amount of a subject ALDH2 agonist. In some embodiments, an "effective amount" of a subject ALDH2 agonist is an amount that is effective to ameliorate one or more symptoms of Parkinson's Disease. In some embodiments, an "effective amount" of a subject ALDH2 agonist is an amount that is effective to slow the progress of the disease. In some embodiments, a subject ALDH2 agonist is administered to the individual systemically, over a period of time of from about 3 months to about 6 months, from about 6 months to about 1 year, or more than 1 year.

Methods of Treating Heart Conditions

The present invention provides methods of treating disorders such as angina, heart failure, insensitivity to nitroglycerin in angina and heart failure (Li et al. (2006) *J. Clin. Invest.* 116:506-511), hypertension (As selin et al. (2006) *Free Radical Biol. and Med.* 41:97), and heart disease. The methods generally involve administering to an individual in need thereof an effective amount of a subject ALDH2 agonist.

In some embodiments, a subject ALDH2 agonist is administered to an individual in conjunction with nitroglycerin treatment. The subject ALDH2 agonist and the nitroglycerin can be administered by the same route of administration (e.g., oral, sublingual, transdermal, translingual, etc.). In the alternative, subject ALDH2 agonist and the nitroglycerin can be administered by different routes of administration. For example, in some embodiments, nitroglycerin is administered sublingually, translingually, transdermally, or orally; and a subject ALDH2 agonist is administered via a different route of administration (e.g., intravenous, intramuscular, etc.). The ALDH2 agonist can be administered before, during, or after administration of the nitroglycerin.

An effective amount of a subject ALDH2 agonist is an amount that, when administered in combination therapy with nitroglycerin, is effective to reduce angina by at least about 10%, at least about 20%, at least about 30%, at least about 40%, at least about 50%, at least about 60%, at least about 70%, at least about 80%, or at least about 90%, or more, within a period of time of from about 1 minute to about 2 minutes, from about 2 minutes to about 3 minutes, from about 3 minutes to about 4 minutes, from about 4 minutes to about 5 minutes, or from about 5 minutes to about 10 minutes, following administration of the ALDH2 agonist. In some embodiments, a subject ALDH2 agonist and nitroglycerin are administered substantially simultaneously, e.g., within about two minutes, within about 1 minute, or within about 30 seconds of one another. The term "combination therapy with nitroglycerin" encompasses administration of a subject ALDH2 agonist substantially simultaneously with nitroglycerin; administration of a subject ALDH2 agonist before administration of nitroglycerin; administration of a subject ALDH2 agonist after administration of nitroglycerin; etc.

In some embodiments, an effective amount of a subject ALDH2 agonist is an amount that is effective to treat hypertension, e.g., to reduce one or more symptoms or indications of hypertension in an individual. For example, in some embodiments, an effective amount of a subject ALDH2 agonist is an amount that is effective to reduce blood pressure in the individual by at least about 5%, at least about 10%, at least about 15%, at least about 20%, or at least about 25%, or more, or to bring the blood pressure of the individual to within a normal range.

In some embodiments, an effective amount of a subject ALDH2 agonist is an amount that is effective to treat heart disease, e.g., to reduce one or more symptoms or indications of heart disease in an individual. Whether a given ALDH2 agonist is effective to treat heart disease can be determined using standard methods of assessing heart function, e.g., electrocardiogram, angiogram, and the like.

Methods of Detoxification

The present invention provides methods of reducing the levels of a toxic compound in an individual, the methods generally involving administering to an individual in need thereof an effective amount of a subject ALDH2 agonist. The present invention provides methods of treating a disorder associated with or resulting from a toxic level of a compound (e.g., a xenogenic aldehyde; a biogenic aldehyde; or a compound that, when ingested, absorbed, or inhaled, gives rise to an aldehyde substrate for ALDH2), the methods generally involving administering to an individual in need thereof an effective amount of a subject ALDH2 agonist, where the level of the compound in the individual is reduced to a non-toxic level.

Toxic compounds whose levels can be reduced in an individual using a subject method include, but are not limited to, ethanol, methanol, ethylene glycol monomethyl ether, xenogenic aldehydes, biogenic aldehydes, and an aldehyde produced by in vivo metabolism of a compound that is ingested, absorbed, or inhaled. A subject ALDH2 agonist is administered in an amount that is effective, when administered in one or more doses, to reduce a toxic level of a compound such as ethanol, methanol, ethylene glycol monomethyl ether, xenogenic aldehydes, biogenic aldehydes, or an aldehyde produced by in vivo metabolism of a compound that is ingested, absorbed, or inhaled. In some embodiments, the aldehyde is acetaldehyde.

As an example, a subject ALDH2 agonist is administered to an individual following excessive alcohol (e.g., ethanol) consumption; and toxic levels of alcohol or aldehyde (e.g., an aldehyde that is a metabolic product of ethanol) in the individual are reduced by at least about 10%, at least about 20%, at least about 30%, at least about 40%, at least about 50%, at least about 60%, at least about 70%, at least about 80%, or at least about 90%, or more, compared to the alcohol or aldehyde levels in the individual before treatment with the ALDH2 agonist. In some embodiments, a subject ALDH2 agonist is administered in an amount that is effective to reduce a toxic alcohol or aldehyde level by at least about 10%, at least about 20%, at least about 30%, at least about 40%, at least about 50%, at least about 60%, at least about 70%, at least about 80%, or at least about 90%, or more, within from about 5 minutes to about 15 minutes, from about 15 minutes to about 30 minutes, from about 30 minutes to 1 hour, from about 1 hour to about 2 hours, from about 2 hours to about 4 hours, from about 4 hours to about 6 hours, or from about 6 hours to about 8 hours, or more, following administration of the ALDH2 agonist. In some embodiments, a subject ALDH2 agonist is administered in an amount that is effective to reduce a toxic alcohol or aldehyde level to a non-toxic level within from about 5 minutes to about 15 minutes, from about 15 minutes to about 30 minutes, from about 30 minutes to 1 hour, from about 1 hour to about 2 hours, from about 2 hours to about 4 hours, from about 4 hours to about 6 hours, or from about 6 hours to about 8 hours, or more, following administration of the ALDH2 agonist.

As an example, a subject ALDH2 agonist is administered to an individual following excessive alcohol (e.g., ethanol) consumption; and levels of acetaldehyde in the individual are reduced by at least about 10%, at least about 20%, at least about 30%, at least about 40%, at least about 50%, at least about 60%, at least about 70%, at least about 80%, or at least about 90%, or more, compared to the alcohol or aldehyde levels in the individual before treatment with the ALDH2 agonist. In some embodiments, a subject ALDH2 agonist is administered in an amount that is effective to reduce an acetaldehyde level by at least about 10%, at least about 20%, at least about 30%, at least about 40%, at least about 50%, at least about 60%, at least about 70%, at least about 80%, or at least about 90%, or more, within from about 5 minutes to about 15 minutes, from about 15 minutes to about 30 minutes, from about 30 minutes to 1 hour, from about 1 hour to about 2 hours, from about 2 hours to about 4 hours, from about 4 hours to about 6 hours, or from about 6 hours to about 8 hours, or more, following administration of the ALDH2 agonist.

The present invention provides methods of reducing aldehyde toxicity, the methods generally involving administering an effective amount of a subject ALDH2 agonist. In some embodiments, an effective amount of an ALDH2 agonist is an amount that is effective to reduce one or more symptoms of aldehyde toxicity. For example, in some embodiments, an effective amount of an ALDH2 agonist is an amount that is effective to reduce one or more symptoms of excess ethanol consumption, where such symptoms include, e.g., headache, dehydration, fatigue, nausea, vomiting, diarrhea, weakness, anxiety, irritability, photophobia, phonophobia, etc.

As an example, a subject ALDH2 agonist is administered to an individual having a toxic level of an aldehyde (e.g., following excessive ethanol consumption); and toxic levels of an aldehyde in the individual are reduced by at least about 10%, at least about 20%, at least about 30%, at least about 40%, at least about 50%, at least about 60%, at least about 70%, at least about 80%, or at least about 90%, or more, compared to the level of the aldehyde in the individual before treatment with the ALDH2 agonist. In some embodiments, a subject ALDH2 agonist is administered in an amount that is effective to reduce a toxic aldehyde level by at least about 10%, at least about 20%, at least about 30%, at least about 40%, at least about 50%, at least about 60%, at least about 70%, at least about 80%, or at least about 90%, or more, within from about 5 minutes to about 15 minutes, from about 15 minutes to about 30 minutes, from about 30 minutes to 1 hour, from about 1 hour to about 2 hours, from about 2 hours to about 4 hours, from about 4 hours to about 6 hours, or from about 6 hours to about 8 hours, or more, following administration of the ALDH2 agonist. In some embodiments, a subject ALDH2 agonist is administered in an amount that is effective to reduce a toxic aldehyde level to a non-toxic level within from about 5 minutes to about 15 minutes, from about 15 minutes to about 30 minutes, from about 30 minutes to 1 hour, from about 1 hour to about 2 hours, from about 2 hours to about 4 hours, from about 4 hours to about 6 hours, or from about 6 hours to about 8 hours, or more, following administration of the ALDH2 agonist.

In some embodiments, a subject ALDH2 agonist reduces the level of both ethanol and an aldehyde, e.g., following excessive ethanol consumption, as described above.

As another example, a subject ALDH2 agonist is administered to an individual having toxic levels of methanol or ethylene glycol monomethyl ether; and the toxic level of methanol or ethylene glycol monomethyl ether is reduced by at least about 10%, at least about 20%, at least about 30%, at least about 40%, at least about 50%, at least about 60%, at least about 70%, at least about 80%, or at least about 90%, or more, compared to the methanol or ethylene glycol monomethyl ether level in the individual before treatment with the ALDH2 agonist. In some embodiments, a subject ALDH2 agonist is administered in an amount that is effective to reduce a toxic methanol or ethylene glycol monomethyl ether level by at least about 10%, at least about 20%, at least about 30%, at least about 40%, at least about 50%, at least about 60%, at least about 70%, at least about 80%, or at least about 90%, or more, within from about 5 minutes to about 15 minutes, from about 15 minutes to about 30 minutes, from about 30 minutes to 1 hour, from about 1 hour to about 2 hours, from about 2 hours to about 4 hours, from about 4 hours to about 6 hours, or from about 6 hours to about 8 hours, or more, following administration of the ALDH2 agonist. In some embodiments, a subject ALDH2 agonist is administered in an amount that is effective to reduce a toxic methanol or ethylene glycol monomethyl ether level to a non-toxic level within from about 5 minutes to about 15 minutes, from about 15 minutes to about 30 minutes, from about 30 minutes to 1 hour, from about 1 hour to about 2 hours, from about 2 hours to about 4 hours, from about 4 hours to about 6 hours, or from about 6 hours to about 8 hours, or more, following administration of the ALDH2 agonist.

As another example, a subject ALDH2 agonist is administered to an individual exhibiting drug toxicity, e.g., a toxic level of an aldehyde following ingestion, absorption, or inhalation of a drug (e.g., a pharmaceutical compound, an illicit drug, etc.). In some embodiments, the aldehyde is produced following ingestion, absorption, or inhalation of a drug, by metabolism of the drug in the body. The toxic level of aldehyde is reduced by at least about 10%, at least about 20%, at least about 30%, at least about 40%, at least about 50%, at least about 60%, at least about 70%, at least about 80%, or at least about 90%, or more, compared to the level of the aldehyde in the individual before treatment with the ALDH2 agonist. In some embodiments, a subject ALDH2 agonist is administered in an amount that is effective to reduce a toxic aldehyde level by at least about 10%, at least about 20%, at least about 30%, at least about 40%, at least about 50%, at least about 60%, at least about 70%, at least about 80%, or at least about 90%, or more, within from about 5 minutes to about 15 minutes, from about 15 minutes to about 30 minutes, from about 30 minutes to 1 hour, from about 1 hour to about 2 hours, from about 2 hours to about 4 hours, from about 4 hours to about 6 hours, or from about 6 hours to about 8 hours, or more, following administration of the ALDH2 agonist. In some embodiments, a subject ALDH2 agonist is administered in an amount that is effective to reduce a toxic aldehyde level to a non-toxic level within from about 5 minutes to about 15 minutes, from about 15 minutes to about 30 minutes, from about 30 minutes to 1 hour, from about 1 hour to about 2 hours, from about 2 hours to about 4 hours, from about 4 hours to about 6 hours, or from about 6 hours to about 8 hours, or more, following administration of the ALDH2 agonist.

Methods of Reducing Salsolinol Levels

The present invention provides methods of reducing salsolinol levels in an individual, the methods generally involving administering to the individual an effective amount of a subject ALDH2 agonist. Salsolinol (1-methyl-6,7-dihydroxy-1,2,3,4-tetrahydroisoquionoline) is a condensation product of dopamine with acetaldehyde. Acetaldehyde is a metabolic product of ethanol. Plasma salsolinol levels are higher in alcoholic compared to non-alcoholics. Reduction of salsolinol levels is useful in reducing alcohol addiction.

In some embodiments, an effective amount of a subject ALDH2 agonist is administered to an individual in need thereof following excessive alcohol (e.g., ethanol) consumption; where the effective amount provides for a reduction in the levels of salsolinol in the individual of at least about 10%, at least about 20%, at least about 30%, at least about 40%, at least about 50%, at least about 60%, at least about 70%, at least about 80%, or at least about 90%, or more, compared to the salsolinol levels in the individual before treatment with the ALDH2 agonist. In some embodiments, an effective amount of a subject ALDH2 agonist is administered to an individual in need thereof at any time (e.g., not necessarily following excessive alcohol consumption). In some embodiments, a subject ALDH2 agonist is administered in an amount that is effective to reduce a salsolinol level by at least about 10%, at least about 20%, at least about 30%, at least about 40%, at least about 50%, at least about 60%, at least about 70%, at least about 80%, or at least about 90%, or more, within from about 5 minutes to about 15 minutes, from about 15 minutes to about 30 minutes, from about 30 minutes to 1 hour, from about 1 hour to about 2 hours, from about 2 hours to about 4 hours, from about 4 hours to about 6 hours, or from about 6 hours to about 8 hours, or more, following administration of the ALDH2 agonist. In some of these embodiments, the individual is one who has been diagnosed with alcoholism. Symptoms and diagnosis of alcoholism are described in, e.g., Enoch and Goldman (2002) American Family Physician 65:441.

Methods of Treating Alcohol Addiction

The present invention provides methods of treating alcohol (ethanol) addiction in an individual. The methods generally involve administering to an individual in need thereof an effective amount of a subject ALDH2 antagonist.

A subject ALDH2 antagonist can be administered to an individual on a regular basis to treat alcohol addiction. For example, in some embodiments, a subject ALDH2 antagonist is administered to an individual in need thereof twice daily, daily, every other day, twice weekly, once per week, or twice per month. A subject ALDH2 antagonist can be administered in the form of a transdermal "patch" to treat alcohol addiction.

"Treating alcohol addiction," as used herein, includes achieving one or more of the following: a reduction in the amount of alcohol consumed; a reduction in the frequency at which alcohol is consumed; a reduction in the craving for alcohol; and a reduction in one or more of the symptoms of excessive alcohol consumption. "Alcohol," as used herein in the context of alcohol addiction, refers to ethanol, e.g., beverages containing 2%, 3%, 4% 5%, or more, by volume, ethanol, e.g., wine, beer, vodka, whiskey, and the like.

Methods of Treating Cancer

The present invention provides methods of treating cancer in an individual. The methods generally involve administering to an individual in need thereof an effective amount of a subject ALDH2 antagonist in conjunction with a standard cancer therapy. Standard cancer therapies include surgery (e.g., surgical removal of cancerous tissue), radiation therapy, bone marrow transplantation, chemotherapeutic treatment, biological response modifier treatment, and certain combinations of the foregoing.

Radiation therapy includes, but is not limited to, x-rays or gamma rays that are delivered from either an externally applied source such as a beam, or by implantation of small radioactive sources.

Chemotherapeutic agents are non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (CYTOXAN™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., *vinca* alkaloids, antitumor antibiotics, enzymes, lymphokines, and epipodophyllotoxins), include, but are not limited to, Ara-C, paclitaxel (TAXOL®), docetaxel (TAXOTERE®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (TAXOL®), TAXOL® derivatives, docetaxel (TAXOTERE®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and ZOLADEX®. Estrogens stimulate proliferation and differentiation; therefore, compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); IRESSA® (ZD 1839, 4-(3-chloro-4-fluorophenylamino)-7-methoxy-6-(3-(4-morpholinyl)propoxy)quinazoline); etc.

"Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., TAXOTERE™ docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

Biological response modifiers suitable for use in connection with the methods of the invention include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) IFN-α; (7) IFN-γ; (8) colony-stimulating factors; (9) inhibitors of angiogenesis; and (10) antagonists of tumor necrosis factor.

A subject method is effective to reduce a tumor load by at least about 5%, at least about 10%, at least about 20%, at least about 25%, at least about 50%, at least about 75%, at least about 85%, or at least about 90%, up to total eradication of the tumor, when compared to a suitable control. Thus, in these embodiments, an "effective amount" of a subject ALDH2 antagonist is an amount that, when administered in conjunction with a standard cancer therapy, is effective to reduce a tumor load by at least about 5%, at least about 10%, at least about 20%, at least about 25%, at least about 50%, at least about 75%, at least about 85%, or at least about 90%, up to total eradication of the tumor, when compared to a suitable control. In an experimental animal system, a suitable control may be a genetically identical animal not treated with the agent. In non-experimental systems, a suitable control may be the tumor load present before administering the agent. Other suitable controls may be a placebo control.

Whether a tumor load has been decreased can be determined using any known method, including, but not limited to, measuring solid tumor mass; counting the number of tumor cells using cytological assays; fluorescence-activated cell sorting (e.g., using antibody specific for a tumor-associated antigen); computed tomography scanning, magnetic resonance imaging, and/or x-ray imaging of the tumor to estimate and/or monitor tumor size; measuring the amount of tumor-associated antigen in a biological sample, e.g., blood; and the like.

Other Disorders

A subject ALDH2 agonist can be administered to an individual in need thereof in the treatment of diabetes. A subject ALDH2 agonist can be administered to an individual in need thereof in the treatment of osteoporosis.

Diabetes

The present invention provides methods of treating diabetes, the methods generally involving administering to an individual in need thereof an effective amount of a subject ALDH2 agonist. In some embodiments, a subject method of treating diabetes provides for treatment of a disorder that is a result of diabetes, e.g., diabetic nephropathy, diabetic neuropathy, and the like.

In some embodiments, a subject ALDH2 agonist is administered in an amount that is effective to reduce a blood glucose level in an individual, e.g., to reduce a blood glucose level in an individual by at least about 10%, at least about 15%, at least about 20%, at least about 25%, at least about 30%, at least about 40%, or at least about 50% when compared to the blood glucose levels in the absence of treatment with the agonist. In some embodiments, an effective amount of an ALDH2 agonist is an amount that is effective to reduce blood glucose levels to a normal range. Normal fasting blood glucose levels are typically in the range of from about 70 mg/dL to about 110 mg/dL before a meal. Normal blood glucose levels 2 hours after a meal are usually less than about 120 mg/dL. Normal blood glucose levels during an oral glucose tolerance test (involving drinking a sugar solution containing about 75 g glucose; then measuring blood glucose levels at various times following drinking the sugar solution) include: less than 140 mg/dL 2 hours after drinking the sugar solution; and all readings between 0 and 2 hours after drinking the sugar solution less than 200 mg/dL. Blood glucose levels are also sometimes expressed in mmol/L. Normal blood glucose levels are generally between about 4 mmol/L and 8 mmol/L. Normal blood glucose levels are generally less than about 10 mmol/L 90 minutes after a meal; and from about 4 mmol/L to about 7 mmol/L before meals.

In some embodiments, a subject treatment method comprises administering a subject ALDH2 agonist, and co-administering at least a second therapeutic agent (e.g., insulin) for the treatment of diabetes. Insulin that is suitable for use herein includes, but is not limited to, regular insulin, semilente, NPH, lente, protamine zinc insulin (PZI), ultralente, insuline glargine, insulin aspart, acylated insulin, monomeric insulin, superactive insulin, hepatoselective insulin, and any other insulin analog or derivative, and mixtures of any of the foregoing. Insulin that is suitable for use herein includes, but is not limited to, the insulin forms disclosed in U.S. Pat. Nos. 4,992,417; 4,992,418; 5,474,978; 5,514,646; 5,504,188; 5,547,929; 5,650,486; 5,693,609; 5,700,662; 5,747,642; 5,922,675; 5,952,297; and 6,034,054; and published PCT applications WO 00/121197; WO 09/010,645; and WO 90/12814. Insulin analogs include, but are not limited to, superactive insulin analogs, monomeric insulins, and hepatospecific insulin analogs.

Osteoporosis

The present invention provides methods of treating osteoporosis, the methods generally involving administering to an individual in need thereof an effective amount of a subject ALDH2 agonist. In some embodiments, an "effective amount" of an ALDH2 agonist is an amount effective to increase bone density in the individual. In other embodiments, an "effective amount" of an ALDH2 agonist is an amount that is effective to reduce the rate of bone density loss.

Subjects Suitable for Treatment

Subjects suitable for treatment with a subject ALDH2 activity modulator include individuals suffering from a condition described above; individuals at risk for developing a condition described above; individuals who have been treated for a condition described above with an agent other than a subject ALDH2 activity modulator, and who either failed to respond to such treatment, or who initially responded to such treatment, but subsequently relapsed; individuals who are refractory to treatment with an agent other than a subject ALDH2 activity modulator for a condition described above; and individuals who cannot tolerate treatment with an agent other than a subject ALDH2 activity modulator for a condition described above.

Methods Involving Administering an ALDH2 Agonist

A subject treatment method involving administration of a subject ALDH2 agonist is suitable for treating various conditions, as noted above, including disorders or conditions associated with or resulting from oxidative stress; disorders or conditions associated with nitroglycerin insensitivity; disorders or conditions associated with toxic levels of ethyl alcohol, aldehyde, methanol, ethylene glycol monomethyl ether, biogenic or xenogenic aldehydes, etc.; and heart diseases and conditions, such as coronary artery disease, angina, etc. In some embodiments, the individual is a human who is homozygous for an ALDH2 allele that encodes an ALDH2 having an amino acid sequence as depicted in FIG. 1A. In other embodiments, the individual is a human who carries one or two ALDH2*2 alleles, where an ALDH2*2 allele encodes an ALDH2 having the E487K variant as depicted in FIG. 1B.

Approximately 40% of the East Asian population carries the semidominant ALDH2*2 allele. Such individuals can be characterized by a response to ethanol consumption that includes one or more of facial flushing, nausea, and tachycardia. In addition, ALDH2*2 individuals are also less responsive to nitroglycerin treatment for such disorders as angina and coronary artery disease. Individuals who are heterozygous or homozygous for the ALDH2*2 allele are suitable for treatment with a subject method involving administration of a subject ALDH2 agonist.

Methods of Treating Conditions Associated with Ischemic Stress

Subjects suitable for treatment with subject ALDH2 agonist include individuals who are scheduled to undergo cardiac surgery or who have undergone cardiac surgery; individuals who have experienced a stroke; individuals who have suffered brain trauma; individuals who have prolonged surgery; individuals who have suffered a myocardial infarct (e.g., acute myocardial infarction); individuals who suffer from cerebrovascular disease; individuals who have spinal cord injury; individuals having a subarachnoid hemorrhage; and individuals who will be subjected to organ transplantation. Subjects suitable for treatment with a subject ALDH2 agonist also include individuals having an ischemic limb disorder, e.g., resulting from Type 1 or Type 2 diabetes.

Methods of Treating Acute Free-Radical Associated Diseases

Subjects suitable for treatment with subject ALDH2 agonist include individuals who are having or who have experienced a seizure; individuals having skin damage resulting from UV exposure; individuals having photodamage of the skin; individuals having an acute thermal skin burn injury; and individuals suffering from tissue hyperoxia.

Methods of Treating Chronic Free-Radical Associated Diseases

Subjects suitable for treatment with subject ALDH2 agonist include individuals who have been diagnosed with Alzheimer's disease, Parkinson's disease, amyotrophic lateral sclerosis, or other neurodegenerative disease; individuals having atherosclerosis; individuals having esophageal cancer; individuals having head and neck squamous cell carcinoma; and individuals having upper aerodigestive tract cancer.

Methods of Treating Cardiac Conditions

Subjects suitable for treatment with a subject ALDH2 agonist include individuals having angina; individuals having heart failure; individuals who exhibit an insensitivity to nitroglycerin in the treatment of angina or heart failure; individuals having hypertension; and individuals having heart disease.

Detoxification Methods

Subjects suitable for treatment with a subject ALDH2 agonist include individuals who have toxic levels of an aldehyde, e.g., via ingestion of a toxic compound, via inhalation of a toxic compound, via ingestion or inhalation of toxic levels of a compound, or via production of the aldehyde during normal metabolism. Such individuals include, but are not limited to, individuals who have ingested or inhaled ethanol, methanol, ethylene glycol monomethyl ether, or other xenogenic or biogenic aldehyde compounds. For example, such individuals include individuals who have ingested or inhaled pesticides, fungicides, or other such compounds; individuals who have consumed excessive levels of ethanol; and the like.

Methods of Treating Alcohol Addiction

Subjects suitable for treatment with a subject ALDH2 antagonist include individuals who have alcohol addiction, including individuals who are considered to be alcoholics (e.g., an individual having a primary, chronic disease characterized by one or more of: impaired control over drinking alcohol, preoccupation with the drug alcohol, use of alcohol despite adverse consequences, and distortions in thinking following consumption of alcohol); individuals suffering from withdrawal symptoms following cessation of alcohol consumption; individuals experiencing alcohol dependence (e.g., alcohol abuse combined with tolerance, withdrawal, and an uncontrollable urge to drink alcohol); and the like.

Methods of Treating Diabetes

Subjects suitable for treatment with a subject ALDH2 agonist include individuals having Type 1 or Type 2 diabetes. Subjects suitable for treatment include individuals who have been diagnosed with Type 1 diabetes mellitus, where such individuals include those having a fasting blood glucose level greater than about 126 mg/dL. Such individuals include those having blood glucose levels of greater than about 200 mg/dL following a two-hour glucose tolerance test (75 g anhydrous glucose orally). Subjects suitable for treatment include individuals who have been diagnosed with Type 2 diabetes; individuals who have not yet been diagnosed with Type 2 diabetes, but who are at risk of developing Type 2 diabetes, e.g., individuals having a body mass index (weight in kilograms divided by height (in meters) squared) greater than 25, e.g., individuals having a body mass index from about 25 to about 27, from about 27 to about 30, or greater than 30.

Methods of Treating Cancer

Subjects suitable for treatment with a subject ALDH2 antagonist for the treatment of cancer, as described above, include individuals having a solid tumor. Solid tumors include, but are not limited to, histiocytic lymphoma, cancers of the brain, genitourinary tract, lymphatic system, stomach, larynx and lung, including lung adenocarcinoma and small cell lung cancer.

Screening Assays

The present invention provides methods for identifying an ALDH2 agonist. The methods generally involve contacting a variant ALDH2 enzyme having reduced enzymatic activity with a test compound, in the presence of a substrate for the variant ALDH2 enzyme; and determining the effect, if any, of the test compound on the enzymatic activity of the variant ALDH2 enzyme.

A "variant ALDH2 enzyme having reduced enzymatic activity" is a variant ALDH2 enzyme that has reduced enzymatic activity relative to an ALDH2 enzyme comprising an amino acid sequence depicted in FIG. 1A (SEQ ID NO:1), or comprising amino acids 18-517 of the an amino acid sequence depicted in FIG. 1A, e.g., the variant ALDH2 enzyme exhibits, in vitro or in vivo, less than about 90%, less than about 80%, less than about 75%, less than about 70%, less than about 60%, less than about 50%, less than about 40%, less than about 30%, less than about 20%, less than about 10%, less than about 5%, or less than about 2%, of the enzymatic activity exhibited by an ALDH2 enzyme comprising an amino acid sequence depicted in FIG. 1A (SEQ ID NO:1), or comprising amino acids 18-517 of the an amino acid sequence depicted in FIG. 1A. In some embodiments, a variant ALDH2 enzyme comprises an amino acid sequence depicted in FIG. 1B (SEQ ID NO:2), or amino acids 18-517 of the an amino acid sequence depicted in FIG. 1B.

As used herein, the term "determining" refers to both quantitative and qualitative determinations and as such, the term "determining" is used interchangeably herein with "assaying," "measuring," and the like.

The terms "candidate agent," "test agent," "agent," "substance," and "compound" are used interchangeably herein. Candidate agents encompass numerous chemical classes, typically synthetic, semi-synthetic, or naturally-occurring inorganic or organic molecules. Candidate agents include those found in large libraries of synthetic or natural compounds. For example, synthetic compound libraries are commercially available from Maybridge Chemical Co. (Trevillet, Cornwall, UK), ComGenex (South San Francisco, Calif.), and MicroSource (New Milford, Conn.). A rare chemical library is available from Aldrich (Milwaukee, Wis.). Alternatively, libraries of natural compounds in the form of bacterial, fungal, plant and animal extracts are available from Pan Labs (Bothell, Wash.) or are readily producible.

Candidate agents may be small organic or inorganic compounds having a molecular weight of more than 50 and less than about 10,000 daltons, e.g., a candidate agent may have a molecular weight of from about 50 daltons to about 100 daltons, from about 100 daltons to about 150 daltons, from about 150 daltons to about 200 daltons, from about 200 daltons to about 500 daltons, from about 500 daltons to about 1000 daltons, from about 1,000 daltons to about 2500 daltons, from about 2500 daltons to about 5000 daltons, from about 5000 daltons to about 7500 daltons, or from about 7500 daltons to about 10,000 daltons. Candidate agents may comprise functional groups necessary for structural interaction with proteins, particularly hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Assays of the invention include controls, where suitable controls include a sample (e.g., a sample comprising the variant ALDH2 enzyme and substrate in the absence of the test agent). Generally a plurality of assay mixtures is run in parallel with different agent concentrations to obtain a differential response to the various concentrations. Typically, one of these concentrations serves as a negative control, i.e. at zero concentration or below the level of detection.

A variety of other reagents may be included in the screening assay. These include reagents like salts, neutral proteins, e.g. albumin, detergents, etc., including agents that are used to facilitate optimal enzyme activity and/or reduce non-specific or background activity. Reagents that improve the efficiency of the assay, such as protease inhibitors, anti-microbial agents, etc. may be used. The components of the assay mixture are added in any order that provides for the requisite activity. Incubations are performed at any suitable temperature, typically between 4° C. and 40° C. Incubation periods are selected for optimum activity, but may also be optimized to facilitate rapid high-throughput screening. Typically between 0.1 hour and 1 hour will be sufficient.

A test compound of interest is a compound that increases the enzymatic activity of the variant ALDH2 by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the enzymatic activity of the ALDH2 polypeptide in the absence of the test compound.

In some embodiments, a test compound of interest is a compound that increases the enzymatic activity of an ALDH2 polypeptide comprising an amino acid sequence set forth in SEQ ID NO:2 (depicted in FIG. 1B), or as set forth in amino acids 18-517 of SEQ ID NO:2, by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100% (or two-fold), at least about 2.5-fold, at least about 5-fold, at least about 10-fold, at least about 15-fold, at least about 20-fold, at least about 25-fold, or at least about 50-fold, or greater than 50-fold, when compared to the enzymatic activity of the ALDH2 polypeptide in the absence of the test compound.

In some embodiments, a test compound of interest is a compound that is specific for ALDH2, e.g., the test compound increases the enzymatic activity of a variant ALDH2 enzyme, but does not substantially increase the enzymatic activity of cytosolic aldehyde dehydrogenase-1 (ALDH1), e.g., the test compound increases the enzymatic activity of an ALDH1 enzyme, if at all, by less than about 5%, less than about 2%, or less than about 1%, when used at a concentration that increases the enzymatic activity of a variant ALDH2 enzyme by at least about 5% or more. In some embodiments, a test agent of interest does not substantially increase the enzymatic activity of alcohol dehydrogenase (ADH), e.g., a test agent of interest increases the enzymatic activity of an ADH, if at all, by less than about 5%, less than about 2%, or less than about 1%, when used at a concentration that increases the enzymatic activity of a variant ALDH2 enzyme by at least about 5% or more.

In some embodiments, a test compound of interest has an $EC_{50}$ of from about 1 nM to about 1 mM, e.g., from about 1 nM to about 10 nM, from about 10 nM to about 15 nM, from about 15 nM to about 25 nM, from about 25 nM to about 50 nM, from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 350 nM, from about 350 nM to about 400 nM, from about 400 nM to about 450 nM, from about 450 nM to about 500 nM, from about 500 nM to about 750 nM, from about 750 nM to about from about 1 µM to about 10 µM, from about 10 µM to about 25 µM, from about 25 µM to about 50 µM, from about 50 µM to about 75 µM, from about 75 µM to about 100 µM, from about 100 µM to about 250 µM, from about 250 µM to about 500 µM, or from about 500 µM to about 1 mM.

A candidate agent is assessed for any cytotoxic activity it may exhibit toward the cell used in the assay, using well-known assays, such as trypan blue dye exclusion, an MTT (3-(4,5-dimethylthiazol-2-yl)-2,5-diphenyl-2H-tetrazolium bromide) assay, and the like. Agents that do not exhibit cytotoxic activity are considered candidate agents.

In many embodiments, the screening method is carried out in vitro, in a cell-free assay. In some embodiments, the in vitro cell-free assay will employ a purified variant ALDH2, where "purified" refers to free of contaminants or any other undesired components. Purified variant ALDH2 that is suitable for a subject screening method is at least about 50% pure, at least about 60% pure, at least about 70% pure, at least about 75% pure, at least about 80% pure, at least about 85% pure, at least about 90% pure, at least about 95% pure, at least about 98% pure, at least about 99% pure, or greater than 99% pure.

Purified variant ALDH2 will in some embodiments be stabilized by addition of one or more stabilizing agents, to maintain enzymatic activity. In some embodiments, a solution of purified variant ALDH2 comprises an aqueous solution of mitochondrial AldDH2 and from about 10% to about 50% glycerol, e.g., from about 10% to about 15%, from about 15% to about 20%, from about 20% to about 25%, from about 25% to about 30%, from about 30% to about 35%, from about 35% to about 40%, from about 40% to about 45%, or from about 45% to about 50% glycerol. In some embodiments, a solution of mitochondrial AldDH2 further comprises one or more of a chelating agent (e.g., EDTA or EGTA); salts such as NaCl, $MgCl_2$, KCl, and the like; buffers, such as a Tris buffer, phosphate-buffered saline, sodium pyrophosphate buffer, and the like; one or more protease inhibitors; and the like.

In some embodiments, the in vitro cell-free assay will employ a recombinant variant ALDH2. Recombinant variant ALDH2 is readily prepared in a variety of host cells such as unicellular microorganisms, or cells of multicellular organisms grown in in vitro culture as unicellular entities. Suitable host cells include bacterial cells such as *Escherichia coli*; yeast cells such as *Saccharomyces cerevisiae, Pichia pastoris, Hansenula polymorpha, Kluyveromyces lactis, Yarrowia lipolytica, Candida utilis, Schizosaccharomyces pombe*, and the like; insect cells such as *Drosophila melanogaster* cells; amphibian cells such as *Xenopus* cells; mammalian cells, such as CHO cells, 3T3 cells, and the like. In some embodiments, the in vitro cell-free assay will employ a human variant ALDH2, e.g., a variant ALDH2 enzyme comprising an amino acid sequence as set forth in amino acids 18-517 of the sequence depicted in FIG. 1B. In some embodiments, the in vitro cell-free assay will employ a variant ALDH2 produced recombinantly in *E. coli* cells.

In some embodiments, the in vitro cell-free assay will employ a fusion protein, comprising a variant ALDH2 fused in-frame to a fusion partner. In some embodiments, the fusion partner is attached to the amino terminus of the variant ALDH2 polypeptide. In other embodiments, the fusion partner is attached to the carboxyl terminus of the variant ALDH2 polypeptide. In other embodiments, the fusion partner is fused in-frame to the variant ALDH2 polypeptide at a location internal to the variant ALDH2 polypeptide. Suitable fusion partners include immunological tags such as epitope tags, including, but not limited to, hemagglutinin, FLAG, and the like; proteins that provide for a detectable signal, including, but not limited to, fluorescent proteins, enzymes (e.g., β-galactosidase, luciferase, horse radish peroxidase, etc.), and the like; polypeptides that facilitate purification or isolation of the fusion protein, e.g., metal ion binding polypeptides such as 6His tags (e.g., ALDH2/6His), glutathione-S-transferase, and the like; polypeptides that provide for subcellular localization; and polypeptides that provide for secretion from a cell.

In some embodiments, the fusion partner is an epitope tag. In some embodiments, the fusion partner is a metal chelating peptide. In some embodiments, the metal chelating peptide is a histidine multimer, e.g., $(His)_6$. In some embodiments, a $(His)_6$ multimer is fused to the amino terminus of the variant ALDH2; in other embodiments, a $(His)_6$ multimer is fused to the carboxyl terminus of the variant ALDH2. The (His)-6- variant ALDH2 fusion protein is purified using any of a variety of available nickel affinity columns (e.g. His-bind resin, Novagen).

Assays for ALDH2 are known in the art, and any known assay can be used in a subject screening method. Examples of assays are found in various publications, including, e.g., Sheikh et al. ((1997) *J. Biol. Chem.* 272:18817-18822) and Farres et al. ((1994) *J. Biol. Chem.* 269:13854-13860). For example, ALDH2 enzymatic activity is assayed at 25° C. in 50 mM sodium pyrophosphate HCl buffer, pH 9.0, 100 mM sodium phosphate buffer, pH 7.4, or 50 mM sodium phosphate buffer, pH 7.4, where the buffer includes $NAD^+$ (e.g., 0.8 mM $NAD^+$, or higher, e.g., 1 mM, 2 mM, or 5 mM $NAD^+$) and a substrate such as 14 μM propionaldehyde. Reduction of NAD is monitored at 340 nm using a spectrophotometer, or by fluorescence increase using a fluoromicrophotometer.

ALDH2 enzymatic activity can be assayed using a standard spectrophotometric method, e.g., by measuring a reductive reaction of the oxidized form of nicotinamide adenine dinucleotide ($NAD^+$) to its reduced form, NADH, at 340 nm, as described in US 2005/0171043, or WO 2005/057213. In an exemplary assay, the reaction is carried out at 25° C. in 0.1 NaPPi buffer, pH 9.5, 2.4 mM $NAD^+$ and 10 mM acetaldehyde as the substrate. Enzymatic activity is measured by a reductive reaction of NAD to NADH at 340 nm, as described in US 2005/0171043, or WO 2005/057213. Alternative, the production of NADH can be coupled with another enzymatic reaction that consumes NADH and that provides for a detectable signal. An example of such an enzymatic reaction is a diaphorase-based reaction, which reduces resazurin to its oxidized fluorescent compound resorufin, as described in US 2005/0171043, or WO 2005/057213. Detection of fluorescent resorufin at 590 nm provides amplified and more sensitive signals for any change in ALDH2 enzymatic activity.

As one non-limiting example, a 120 μl reaction mixture for ALDH2 enzymatic activity comprises the following components:

43 μl 150 mM sodium pyrophosphate (NaPPi) buffer, pH 9.0;
30 μl 10 mM $NAD^+$;
15 μl 80 mM acetaldehyde;
1 μl of resazurin (0.2 mg/ml in $H_2O$);
1 μl of diaphorase (1 unit, e.g., from *Clostridium kluyveri*);
2 μl of variant ALDH2 (e.g., 2 μl of variant ALDH2 at (0.5-2 μg/μl); and
28 μl of a solution comprising an agent to be tested, which agent has been resuspended in an appropriate solvent (e.g., an aqueous solution, DMSO, and the like).

Fluorescent detection of the above-described reaction as described in Table 1:

TABLE 1

|  | Excitation | Emission | Cutoff |
| --- | --- | --- | --- |
| Channel 1 | 340 nm | 445 nm | 410 nm |
| Channel 2 | 565 nm | 590 nm | 570 nm |

This reaction can be carried out in a 96-well, a 384-well, a 1536-well micro-well plate, etc., or adapted to other screening formats.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Identification and Characterization of ALDH2 Agonists

Methods
In Vitro Screen for ALDH2 Agonists (Activators) and Antagonists (Inhibitors)

Compounds were screened using a method as depicted schematically in FIG. 2. Essentially, the reaction is carried out at 25° C. in 0.1 NaPPi buffer, pH 9.5, 2.4 mM $NAD^+$ and 10 mM acetaldehyde as the substrate. Enzymatic activity is measured by a reductive reaction of $NAD^+$ to NADH at 340 nm. Alternatively, the production of NADH can be coupled with another enzymatic reaction that consumes NADH and that provides for a detectable signal. An example of such an enzymatic reaction is a diaphorase-based reaction, which reduces resazurin to its oxidized fluorescent compound resorufin.

For example, a 120 μl reaction mixture for ALDH2 enzymatic activity comprises the following components:
  43 μl 150 mM sodium pyrophosphate (NaPPi) buffer, pH 9.0;
  30 μl 10 mM $NAD^+$;
  15 μl 80 mM acetaldehyde;
  1 μl of resazurin (0.2 mg/ml in $H_2O$);
  1 μl of diaphorase (1 unit, e.g., from *Clostridium kluyveri*);
  2 μl of variant ALDH2 (e.g., 2 μl of variant ALDH2 at (0.5-2 μg/μl); and
  28 μl of a solution comprising an agent to be tested, which agent has been resuspended in an appropriate solvent (e.g., an aqueous solution, DMSO, and the like).

Fluorescent detection of the above-described reaction as described in Table 1:

TABLE 1

|  | Excitation | Emission | Cutoff |
| --- | --- | --- | --- |
| Channel 1 | 340 nm | 445 nm | 410 nm |
| Channel 2 | 565 nm | 590 nm | 570 nm |

Histidine-Tagged E487K ALDH2 Protein

A fusion protein that includes the E487K variant of human ALDH2 (see amino acid sequence depicted in FIG. 1B) and a poly-histidine tag was synthesized and used in screens for ALDH2 agonists. An expression construct that encodes the E87K variant fused in-frame to a poly-histidine (His) tag was introduced into *E. coli*, and expression was induced by the addition of isopropyl-1-thio-3-D-galactoside (IPTG); and His-tagged E487K ALDH2 variant was produced. The His-tagged E487K ALDH2 variant was purified from *E. coli* extract using a metal ion affinity column to bind the His-tagged E487K ALDH2 variant. His-tagged E487K ALDH2 variant was eluted from the column and used in screening assays to identify ALDH2 agonists.

The His-tagged E487 ALDH2 was derived from amino acids 18-517 as shown in FIG. 1B, with the His-tag fused to the N-terminus of the E487 variant.

Ex Vivo Assay

Ex vivo Langendorff preparations of rat hearts were used as a model to assess the damage incurred by no-flow ischemia and reperfusion injury. This is an experimental model that mimics the clinical situation of myocardial infarction in patients. Rat hearts were excised and cannulated on a Langendorff apparatus via the aorta. Retrograde perfusion was carried out using the standard oxygenated Kreb-Hensleit buffer maintained at 37° C. All hearts were stabilized by an initial 5- to 10-minute perfusion period followed by delivery of different cardioprotective agents or AldDH2 inhibitors for 10-30 minutes, depending on the reagent. Reagents used in some of the representative experiments including ethanol (50 mM), εPKC isozyme-selective activator and inhibitor peptides (1 μM), cyanamide (5 mM) and nitroglycerin (2 μM). Ischemia was then introduced by 25 minutes of no-flow followed by 60 minutes of reperfusion.

The degree of ischemia/reperfusion damage was measured by two independent commonly accepted parameters. In one assay, a cross-section of heart slices were obtained immediately after reperfusion and stained with 2,3,5-triphenyl-tetrazolium chloride (TTC) for infarct size measurement. In another assay, creatine phosphate kinase activity was measured from reperfusate of each heart collected during reperfusion. The data indicated that the two methods yielded comparable results for the assessment of cardiac damage. Homogenates from each heart was also obtained from a separate section of the identical sample and analyzed for aldehyde dehydrogenase enzymatic activity. Enzymatic activity was determined by a standard spectrophotometric method described above using acetaldehyde as the substrate and NAD as a cofactor.

Results

The histidine-tagged E487K ALDH2 variant was used to screen for ALDH2 activators. Of 63,000 compounds tested, 3 compounds were identified as ALDH2 activators. The initial 3 compounds were as follows:

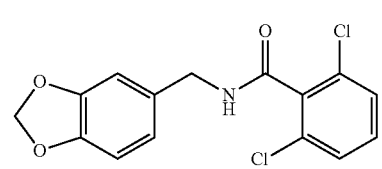

Compound 1

This compound is also referred to as Compound 1, and is N-(1,3-benzodioxol-5-ylmethyl)-2,6-dichlorobenzamide.

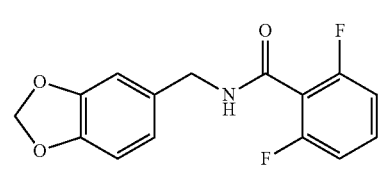

Compound 2

This compound is also referred to as Compound 2, and is N-(1,3-benzodioxol-5-ylmethyl)-2,6-difluorobenzamide.

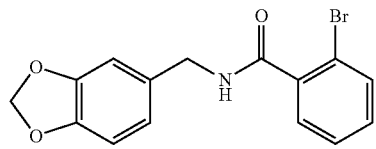

Compound 3

This compound is also referred to as Compound 3, and is N-(1,3-benzodioxol-5-ylmethyl)-2-bromobenzamide.

Figure 3:
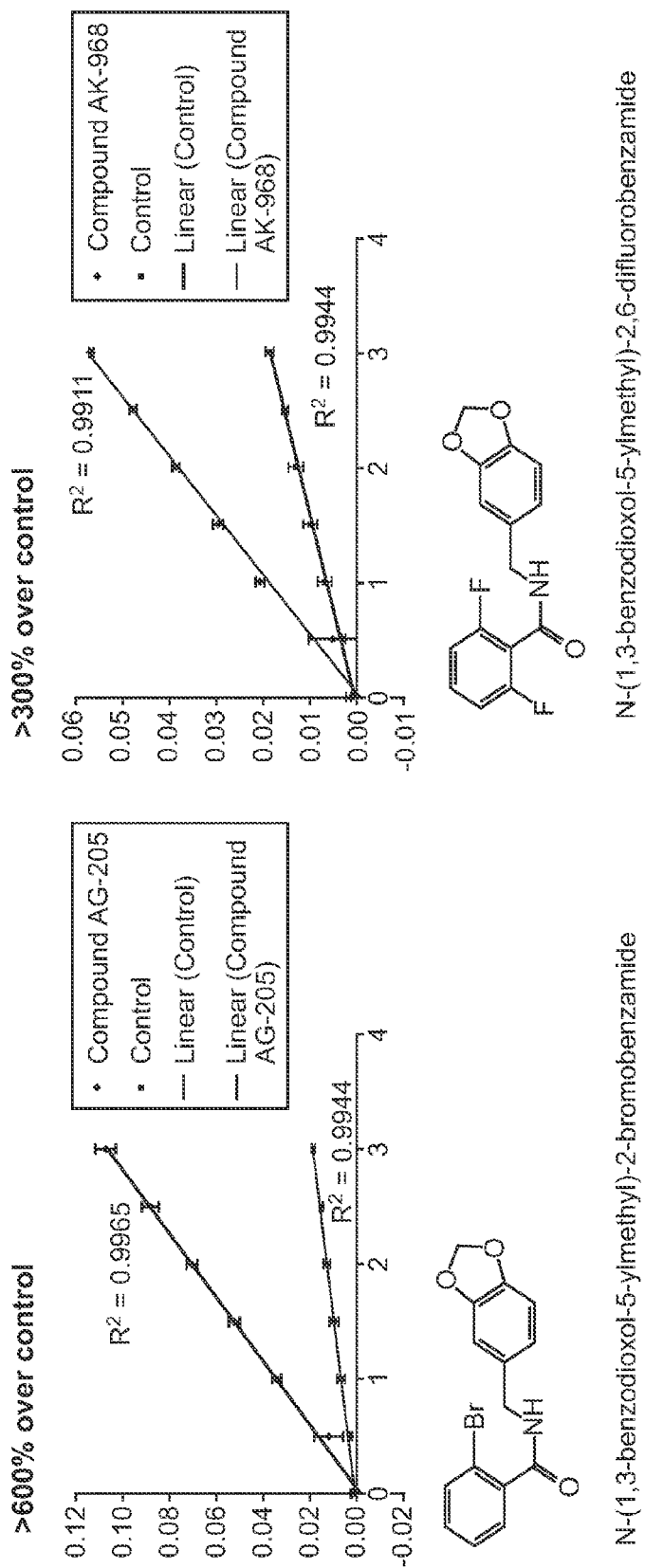
FIG. 3 depicts the effect of two exemplary ALDH2 agonists on enzymatic activity of an E487K variant of human ALDH2.

The activity of compounds 2 and 3 was tested against the E487K ALDH2 variant. The results are depicted in FIG. 3. Compound 2 and Compound 3 increased enzymatic activity of the E487K ALDH2 variant approximately 300% and 600%, respectively, over control (without activator compound) activity. (FIG. 3: n=3 for both left and right panels.)

Figure 4:
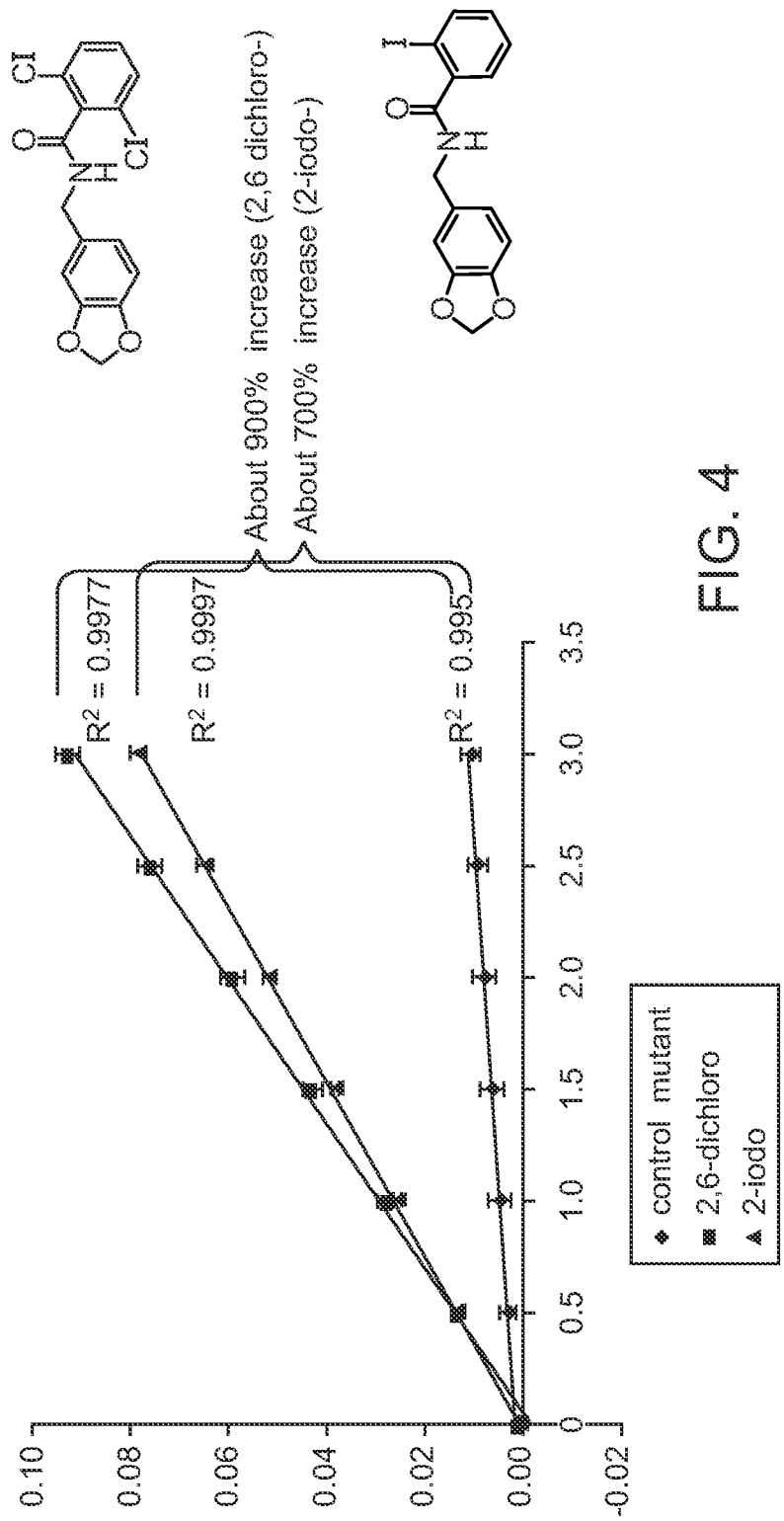
FIG. 4 depicts the effect of two exemplary ALDH2 agonists on enzymatic activity of an E487K variant of human ALDH2.

A 2-iodo variant of Compound 3 was synthesized. The variant is N-(1,3-benzodioxol-5-ylmethyl)-2-iodobenzamide. The activity of the 2-iodo variant and Compound 1 was tested against the E487K ALDH2 variant. The results are depicted in FIG. 4. Compound 1 and the 2-iodo variant of Compound 3 increased enzymatic activity of the E487K ALDH2 variant approximately 900% and 700%, respectively, over control (without activator compound) activity. (FIG. 4: n=3).

Specificity of ALDH2 Agonists

The activity of Compounds 1, 2, and 3 was tested against wild-type ALDH2 (where "wild-type" ALDH2 has a glutamic acid at position 487, as depicted in FIG. 1A), against the E487K ALDH2 variant, and against ALDH1A1. Compound structures are depicted in FIG. 5A. The results are depicted in FIGS. 5B and 5C. In in vitro assays, activity of the wild-type ALDH2 enzyme is from 41% to 65%. Compounds 1-3 activated the E487K ALDH2 variant by from 300% to 900% at 10 µM to 20 µM. Activation of ALDH2 by benzo-dioxol benzamide compounds (e.g., Compounds 1-3) appeared to be selective: There was no significant effect of these compounds on the enzymatic activity of ADH1 or the closely related cytosolic form of aldehyde dehydrogenase 1 (ALDH1).

Activity of ALDH2 Agonists in Myocardial Infarction Model.

Figure 6:
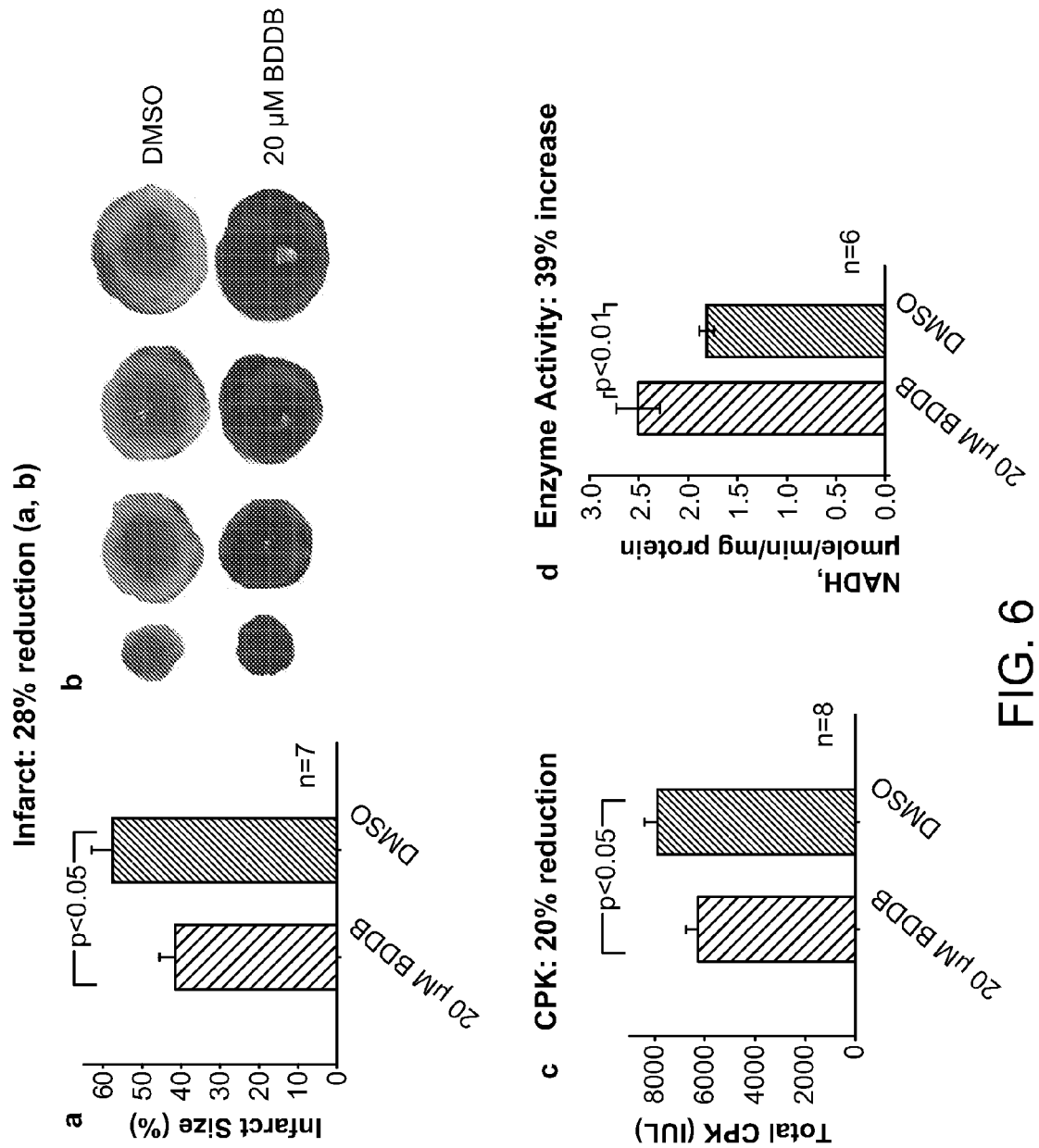
FIGS. 6A-D depict the effect of an exemplary ALDH2 agonist in an ex vivo model of myocardial infarction.

The effect of compound 1 was tested in an ex vivo model of myocardial infarction, to determine whether Compound 1 could protect myocardium from ischemia-reperfusion damage. The results are shown in FIGS. 6A-6D. As shown in FIG. 6A, infarct size was significantly reduced from 57.7±5.4% to 41.6±4.1, p<0.05, n=7. FIG. 6B depicts images of heart sections exposed to IR injury in the presence and absence of N-(1,3-benzodioxol-5-ylmethyl)-2,6-dichlorobenzamide (BDDB). White tissue is infarcted. FIG. 6C depicts CPK release. CPK release was significantly decreased from 5530±329 Units/Liter to 4396 Units/Liter*P<0.05, n=8). FIG. 6D depicts the increase in ALDH2 enzymatic activity in compound 1-treated hearts 3.3±0.30 to 2.5±0.11 µmole NADH/min/mg protein, **p<0.01, n=6).

Synthesis of Additional Compounds

Several additional compounds were synthesized. The structures of these compounds (referred to as XO-3, XO-4, XO-5, XO-6, XO-7, XO-8, XO-9, XO-11, XO-12, XO-13, XO-22, XO-25, XO-26, XO-28, XO-29, XO-33, XO-36, and XO-39) are depicted above.

The compounds referred to as XO-3, XO-4, XO-5, XO-6, XO-7, XO-8, XO-9, XO-11, XO-12, XO-13, XO-22, XO-25, XO-26, XO-28, XO-29, XO-33, XO-36, and XO-39 were synthesized by reacting an amine with an acid chloride or a sulfonic acid chloride in the presence of a base. In one case, 3,4-difluoro-benzylamine was reacted with 2-bromo-benzoyl chloride in the presence of N,N-diisopropylethylamine in dichloromethane to form compound XO-4.

All compounds were confirmed by thin layer chromatography, $^1$H-nuclear magnetic resonance, and mass spectrometry.

Figure 7:
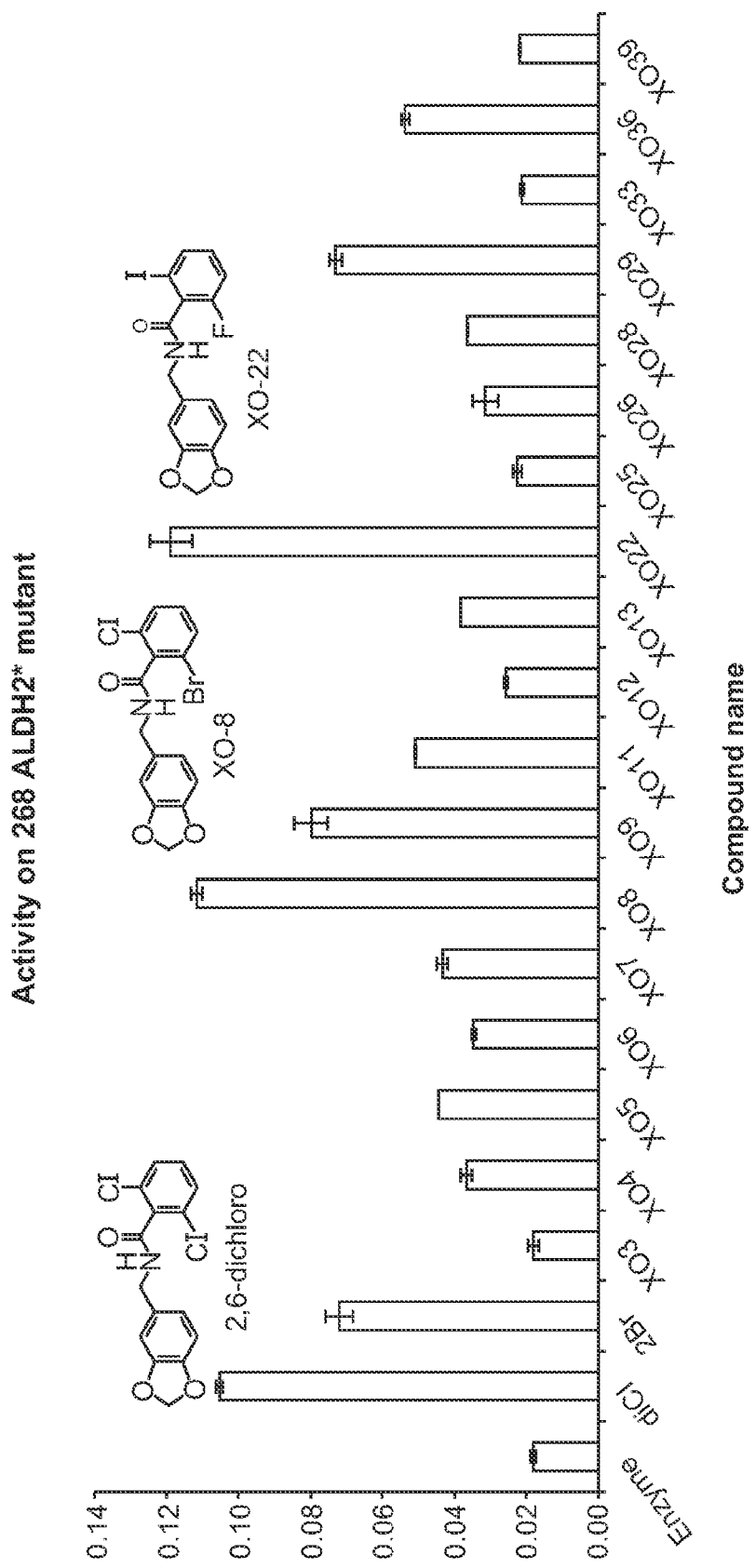
FIG. 7 depicts the activity of various ALDH2 agonists on an E487K variant of human ALDH2.

FIG. 7 depicts the effect of these compounds (XO-3, XO-4, XO-5, XO-6, XO-7, XO-8, XO-9, XO-11, XO-12, XO-13, XO-22, XO-25, XO-26, XO-28, XO-29, XO-33, XO-36, and XO-39) on activity of the E487K ALDH2 variant. All compounds were used at 10 µM, and assays were carried out in duplicate. (FIG. 7: n=3).

Example 2

Identification and Characterization of ALDH2 Inhibitors

Figure 8:
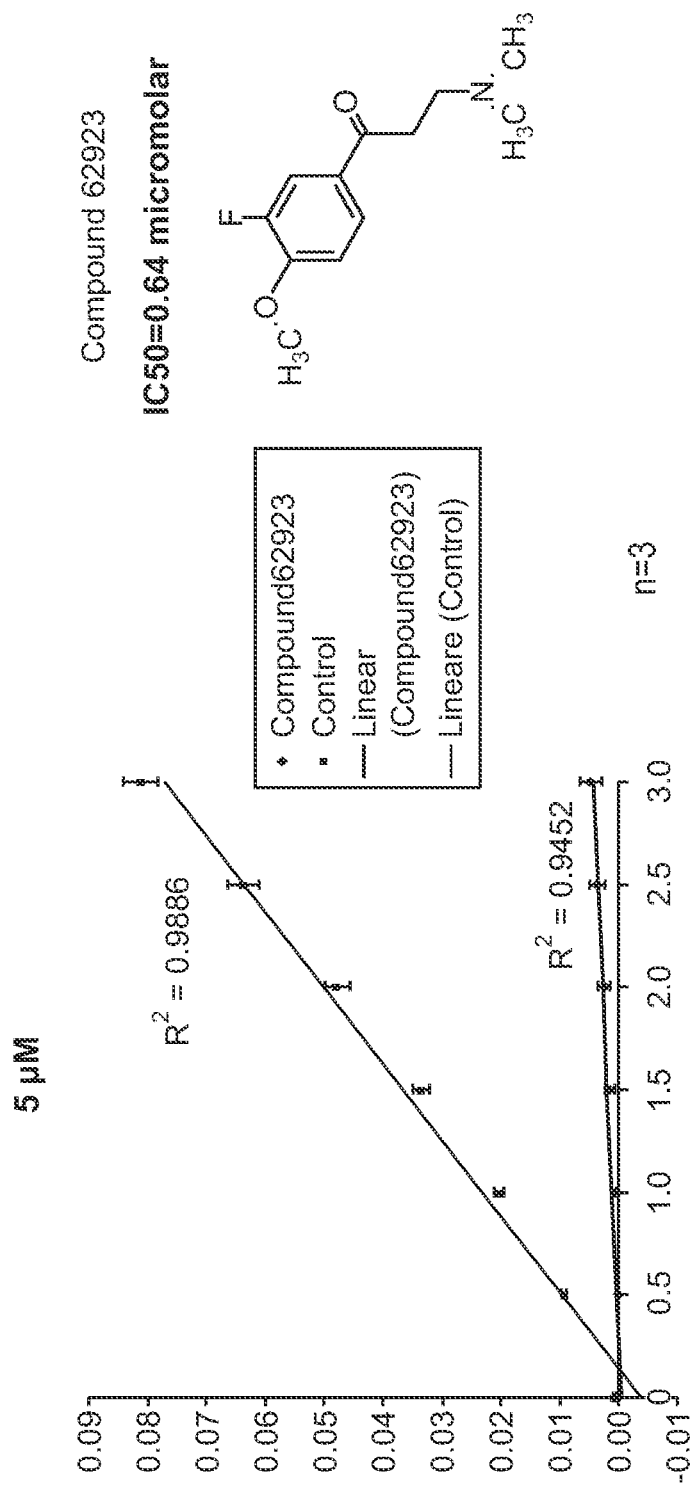
FIG. 8 depicts inhibition of ALDH2 by an exemplary ALDH2 antagonist.
Figure 9:
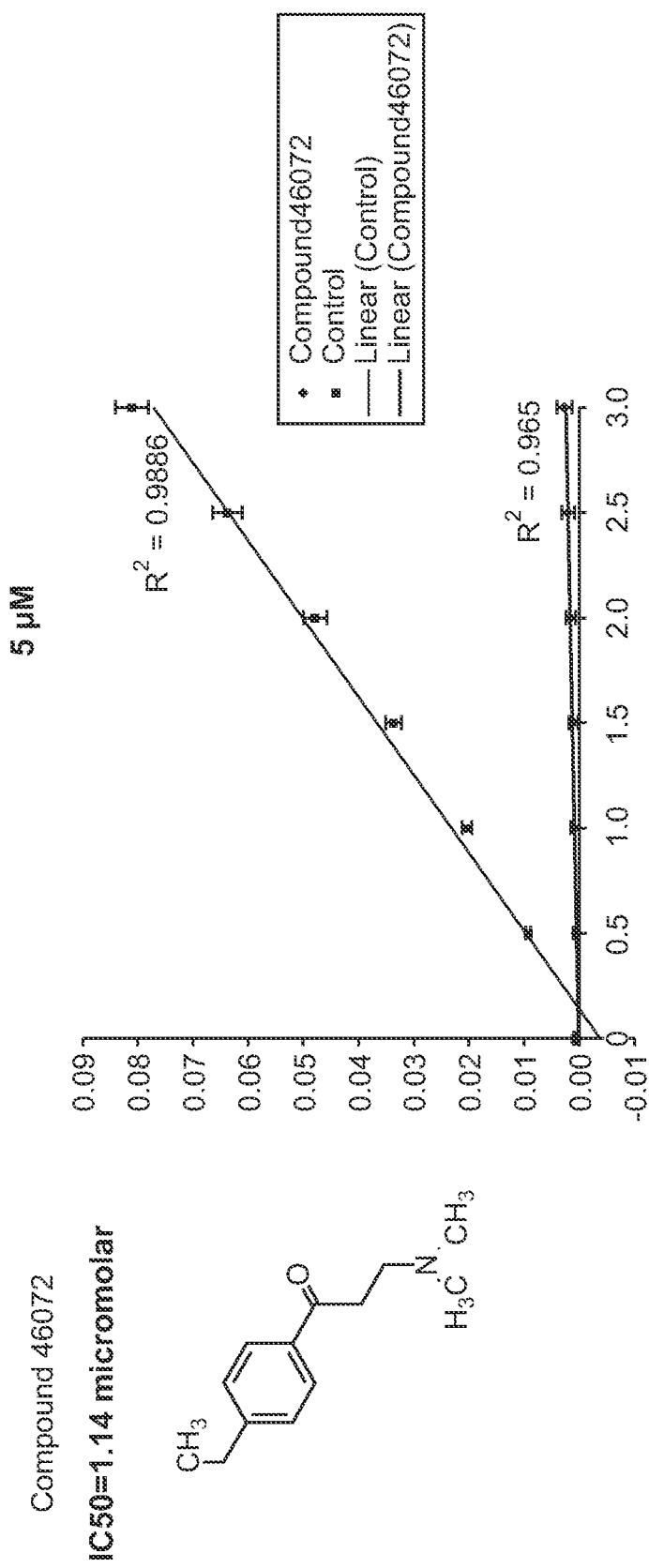
FIG. 9 depicts inhibition of ALDH2 by an exemplary ALDH2 antagonist.
Figure 10:
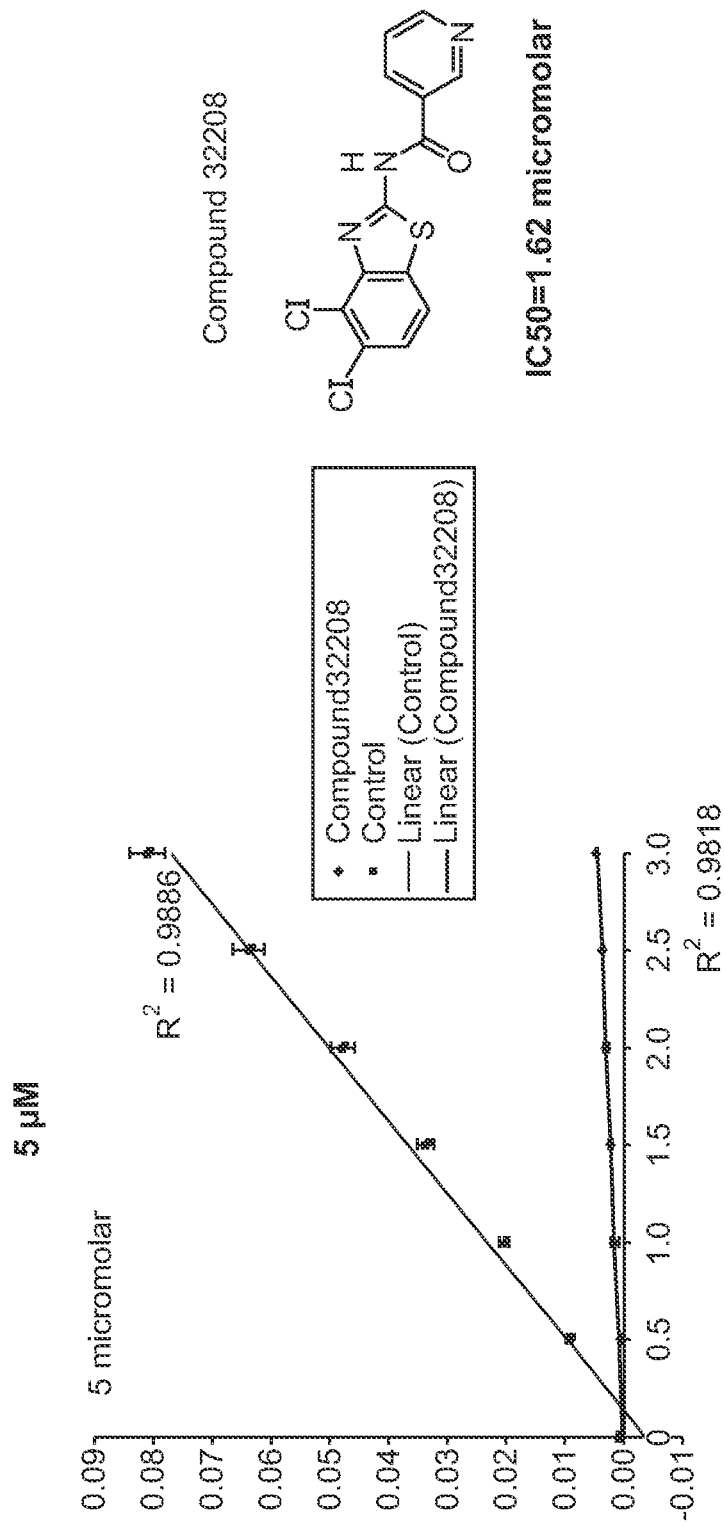
FIG. 10 depicts inhibition of ALDH2 by an exemplary ALDH2 antagonist.

Compounds were screened, as described above, but using the "wild-type" ALDH2 enzyme. Of 63,000 compounds screened, six inhibitors were identified. Three of the compounds, referred to in FIGS. 8, 9, and 10 as #062923, #046072, and #032208, respectively, were assayed for their effect on ALDH2 enzymatic activity. The results are shown in FIGS. 8-10. As shown in FIG. 8, compound #062923 inhibited ALDH2 activity at an IC$_{50}$ of 0.63 µM. (Note that for FIGS. 3, 4, and 8-10, the x-axis unit is: OD at 340 nm. For FIGS. 3, 4, and 7-10, the y-axis unit is: Time (in minutes). As shown in FIG. 9, compound #046072 inhibited ALDH2 activity at an IC$_{50}$ of 1.14 µM. (FIG. 9: n=3). As shown in FIG. 10, compound #032208 inhibited ALDH2 activity at an IC$_{50}$ of 1.62 µM. (FIG. 10: n=3).

The structures of additional compounds (referred to as Compounds 8-18, above) that were identified in the initial screen as ALDH2 inhibitors are provided above.

Example 3

BDDB Protects Against Ischemia/Reperfusion Injury In Vivo

Male Wistar rats (250-300 g) were anesthetized by 3% isoflurane. The surgical procedures used for left anterior descending coronary artery (LAD) ligation are based on published protocols. Animals were intubated, and ventilated with a Harvard rodent ventilator at a rate of 80 breaths per minute (5-15 mm Hg). Maintenance anesthesia was provided via 1% inhalational isoflurane, and body temperature was maintained at 37° C. using a rectal probe linked to a thermocoupled thermometer and an appropriate heating blanket. The heart was exposed by median sternotomy. Following a 20-minute period of stabilization, a ligature was placed around the LAD coronary artery, close to its origin from the aortic root. The ends of the ligature were passed through polyethylene tubing forming a small noose in which a syringe plunger was rested upon the myocardial surface. Coronary occlusion was achieved by pressing the tubing against the plunger while pulling on the ligature followed by clamping the tubing with a hemostat. Occlusion was determined by observation of immediate pallor of the left ventricular free wall. Reflow was achieved by release of the ligature.

Following exposure of the heart and stabilization, BDDB was infused directly into the left ventricle using a 30G needle connected to a catheter and inserted through the apex of the heart into the left ventricle. Correct placement was verified by a small backflow of blood into the catheter as well as post-mortem dissection. The catheter was attached to a syringe and BDDB was infused at a rate of 0.08 ml/min with a target volume of 0.16 ml and a final concentration of 8.5 mg/kg. Five minutes after BDDB treatment, the LAD was occluded. Control hearts were injected with the same volume of DMSO at the same flow rate. In all the experiments, the 35-minute occlusion was followed by 60 minutes of reperfusion.

At the end of reperfusion, hearts were excised and flushed with 0.9% saline. Infarct size analysis was carried by the same procedures as described in the ex vivo experiments using TTC. 0.45 ml of the blood sample were withdrawn into a 0.05 ml heparin-primed syringe 15 minute and 30 minute after termination of the LAD occlusion time points via an apical punch of the left ventricle. Serum was separated by centrifugation at 5000 g for 5 minutes on a tabletop centrifuge and creatine phosphate kinase (CPK) values were determined.

Figure 11:
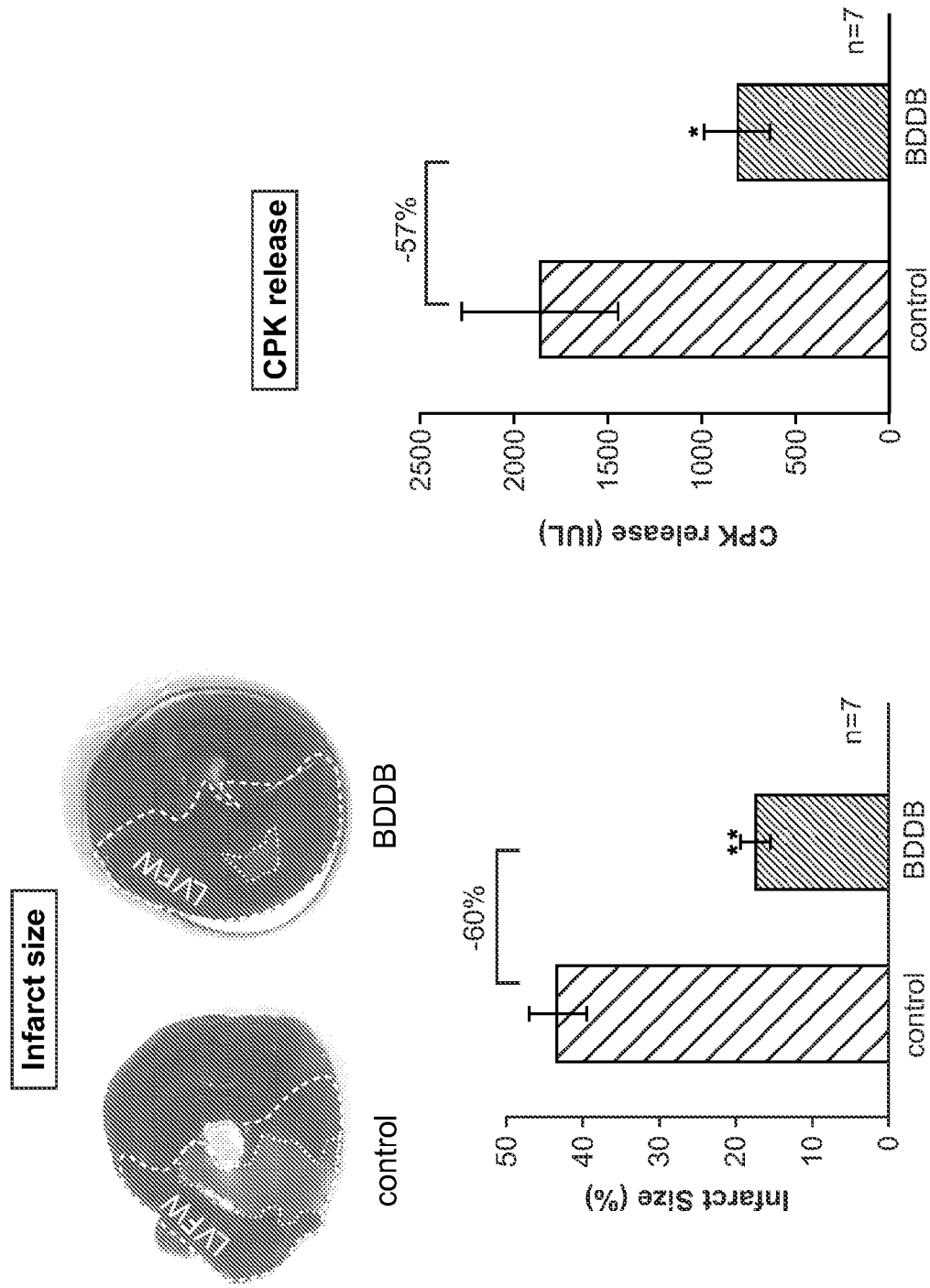
FIG. 11 depicts the effect of an exemplary ALDH2 agonist in an in vivo model of myocardial infarction.

The results are shown in FIG. 11. Ligation of the left anterior descending (LA) coronary artery resulted in 43% infarction of the left ventricular free wall and a significant creatine phosphokinase (CPK) release into the blood (FIG. 11). Administration of 8.5 mg/kg BDDB into the left ventricle five minutes before LAD ligation decreased the extent of myocardial infarction by about 60% and CPK release by about 57% (FIG. 11 p<0.01). These results indicated that ALDH2 activation is sufficient to protect the heart from ischemia damage, in vivo.

Example 4

Activation of ALDH2 by Agonist Compounds XO43, XO44 and BDDB

BDDB derivative compounds, XO43 and XO44 as depicted in FIG. 12, were synthesized and tested in ALDH2 enzymatic assays. Both compounds showed potency in activating ALDH2*1 and ALDH2*2 recombinant enzyme in a standard assay using 0.1 sodium pyrophosphate buffer, pH 9.5, 2.4 mM NAD and 10 mM acetaldehyde as the substrate at 25° C. Enzymatic activity was measured by a reductive reaction of NAD to NADH at 340 nm, as described in US 2005/0171043; and WO 2005/057213. The data are presented in FIG. 12. XO43, XO44 and BDDB showed a dosage dependent effect of ALDH2 activation in the range of 10-200 μM. The ALDH2*1 wild type enzyme showed an increase of about 180% in activity and the ALDH2*2 mutant enzyme showed and increase of >900% at the higher concentration. (FIG. 12: n=3 for both right and left panels.)

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

---

What is claimed is:

1. A compound of one of the following formulas:

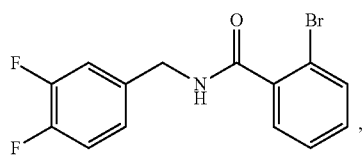
XO-4

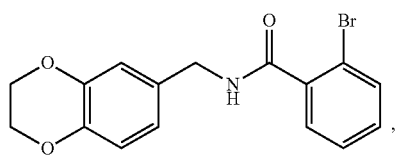
XO-5

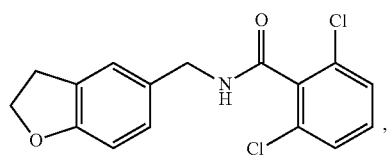
XO-9

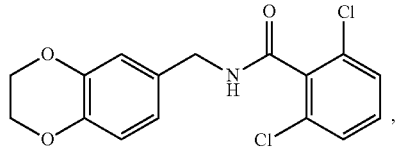
XO-36

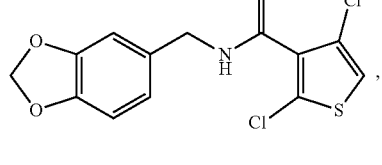
XO-12

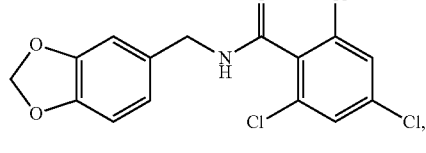
XO-6

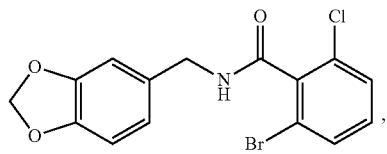
XO-8

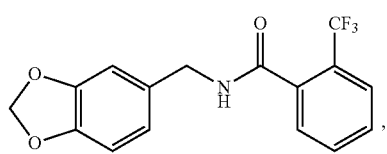
XO-11

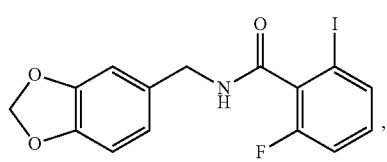
XO-22

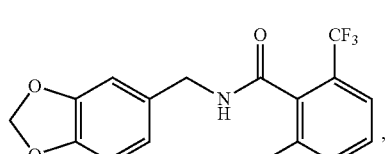
XO-26

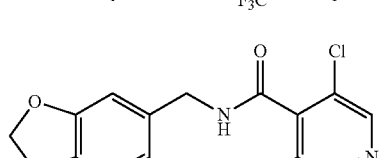
XO-43

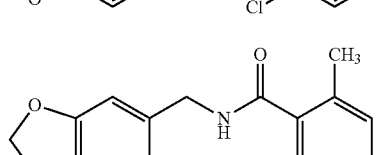
XO-44

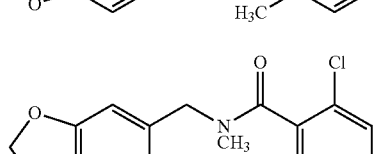
XO-45

, and

-continued
XO-46
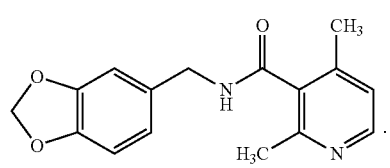
2. A pharmaceutical composition comprising:
(a) a compound of claim 1; and
(b) a pharmaceutically acceptable excipient.
3. A compound of the formula:
XO-44
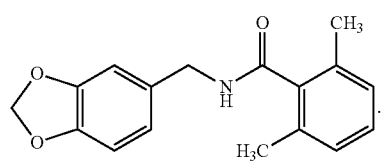
* * * * *

SEQUENCE LISTING

```
<160> NUMBER OF SEQ ID NOS: 2

<210> SEQ ID NO 1
<211> LENGTH: 517
<212> TYPE: PRT
<213> ORGANISM: Homo sapiens

<400> SEQUENCE: 1

Met Leu Arg Ala Ala Ala Arg Phe Gly Pro Arg Leu Gly Arg Arg Leu
1               5                   10                  15

Leu Ser Ala Ala Ala Thr Gln Ala Val Pro Ala Pro Asn Gln Gln Pro
            20                  25                  30

Glu Val Phe Cys Asn Gln Ile Phe Ile Asn Asn Glu Trp His Asp Ala
        35                  40                  45

Val Ser Arg Lys Thr Phe Pro Thr Val Asn Pro Ser Thr Gly Glu Val
    50                  55                  60

Ile Cys Gln Val Ala Glu Gly Asp Lys Glu Asp Val Asp Lys Ala Val
65                  70                  75                  80

Lys Ala Ala Arg Ala Ala Phe Gln Leu Gly Ser Pro Trp Arg Arg Met
                85                  90                  95

Asp Ala Ser His Arg Gly Arg Leu Leu Asn Arg Leu Ala Asp Leu Ile
            100                 105                 110

Glu Arg Asp Arg Thr Tyr Leu Ala Ala Leu Glu Thr Leu Asp Asn Gly
        115                 120                 125

Lys Pro Tyr Val Ile Ser Tyr Leu Val Asp Leu Asp Met Val Leu Lys
    130                 135                 140

Cys Leu Arg Tyr Tyr Ala Gly Trp Ala Asp Lys Tyr His Gly Lys Thr
145                 150                 155                 160
```

Ile Pro Ile Asp Gly Asp Phe Phe Ser Tyr Thr Arg His Glu Pro Val
                165                 170                 175

Gly Val Cys Gly Gln Ile Ile Pro Trp Asn Phe Pro Leu Leu Met Gln
            180                 185                 190

Ala Trp Lys Leu Gly Pro Ala Leu Ala Thr Gly Asn Val Val Val Met
        195                 200                 205

Lys Val Ala Glu Gln Thr Pro Leu Thr Ala Leu Tyr Val Ala Asn Leu
    210                 215                 220

Ile Lys Glu Ala Gly Phe Pro Pro Gly Val Val Asn Ile Val Pro Gly
225                 230                 235                 240

Phe Gly Pro Thr Ala Gly Ala Ala Ile Ala Ser His Glu Asp Val Asp
                245                 250                 255

Lys Val Ala Phe Thr Gly Ser Thr Glu Ile Gly Arg Val Ile Gln Val
            260                 265                 270

Ala Ala Gly Ser Ser Asn Leu Lys Arg Val Thr Leu Glu Leu Gly Gly
        275                 280                 285

Lys Ser Pro Asn Ile Ile Met Ser Asp Ala Asp Met Asp Trp Ala Val
    290                 295                 300

Glu Gln Ala His Phe Ala Leu Phe Phe Asn Gln Gly Gln Cys Cys Cys
305                 310                 315                 320

Ala Gly Ser Arg Thr Phe Val Gln Glu Asp Ile Tyr Asp Glu Phe Val
                325                 330                 335

Glu Arg Ser Val Ala Arg Ala Lys Ser Arg Val Val Gly Asn Pro Phe
            340                 345                 350

Asp Ser Lys Thr Glu Gln Gly Pro Gln Val Asp Glu Thr Gln Phe Lys
        355                 360                 365

Lys Ile Leu Gly Tyr Ile Asn Thr Gly Lys Gln Glu Gly Ala Lys Leu
    370                 375                 380

Leu Cys Gly Gly Gly Ile Ala Ala Asp Arg Gly Tyr Phe Ile Gln Pro
385                 390                 395                 400

Thr Val Phe Gly Asp Val Gln Asp Gly Met Thr Ile Ala Lys Glu Glu
                405                 410                 415

Ile Phe Gly Pro Val Met Gln Ile Leu Lys Phe Lys Thr Ile Glu Glu
            420                 425                 430

Val Val Gly Arg Ala Asn Asn Ser Thr Tyr Gly Leu Ala Ala Ala Val
        435                 440                 445

Phe Thr Lys Asp Leu Asp Lys Ala Asn Tyr Leu Ser Gln Ala Leu Gln
    450                 455                 460

Ala Gly Thr Val Trp Val Asn Cys Tyr Asp Val Phe Gly Ala Gln Ser
465                 470                 475                 480

Pro Phe Gly Gly Tyr Lys Met Ser Gly Ser Gly Arg Glu Leu Gly Glu
                485                 490                 495

Tyr Gly Leu Gln Ala Tyr Thr Glu Val Lys Thr Val Thr Val Lys Val
            500                 505                 510

Pro Gln Lys Asn Ser
        515

<210> SEQ ID NO 2
<211> LENGTH: 517
<212> TYPE: PRT
<213> ORGANISM: Homo sapiens

<400> SEQUENCE: 2

Met Leu Arg Ala Ala Ala Arg Phe Gly Pro Arg Leu Gly Arg Arg Leu

-continued

```
  1               5                  10                 15
Leu Ser Ala Ala Ala Thr Gln Ala Val Pro Ala Pro Asn Gln Gln Pro
             20                 25                 30
Glu Val Phe Cys Asn Gln Ile Phe Ile Asn Asn Glu Trp His Asp Ala
             35                 40                 45
Val Ser Arg Lys Thr Phe Pro Thr Val Asn Pro Ser Thr Gly Glu Val
             50                 55                 60
Ile Cys Gln Val Ala Glu Gly Asp Lys Glu Asp Val Asp Lys Ala Val
 65                 70                 75                 80
Lys Ala Ala Arg Ala Ala Phe Gln Leu Gly Ser Pro Trp Arg Arg Met
             85                 90                 95
Asp Ala Ser His Arg Gly Arg Leu Leu Asn Arg Leu Ala Asp Leu Ile
            100                105                110
Glu Arg Asp Arg Thr Tyr Leu Ala Ala Leu Glu Thr Leu Asp Asn Gly
            115                120                125
Lys Pro Tyr Val Ile Ser Tyr Leu Val Asp Leu Asp Met Val Leu Lys
            130                135                140
Cys Leu Arg Tyr Tyr Ala Gly Trp Ala Asp Lys Tyr His Gly Lys Thr
145                150                155                160
Ile Pro Ile Asp Gly Asp Phe Phe Ser Tyr Thr Arg His Glu Pro Val
            165                170                175
Gly Val Cys Gly Gln Ile Ile Pro Trp Asn Phe Pro Leu Leu Met Gln
            180                185                190
Ala Trp Lys Leu Gly Pro Ala Leu Ala Thr Gly Asn Val Val Val Met
            195                200                205
Lys Val Ala Glu Gln Thr Pro Leu Thr Ala Leu Tyr Val Ala Asn Leu
            210                215                220
Ile Lys Glu Ala Gly Phe Pro Pro Gly Val Val Asn Ile Val Pro Gly
225                230                235                240
Phe Gly Pro Thr Ala Gly Ala Ala Ile Ala Ser His Glu Asp Val Asp
            245                250                255
Lys Val Ala Phe Thr Gly Ser Thr Glu Ile Gly Arg Val Ile Gln Val
            260                265                270
Ala Ala Gly Ser Ser Asn Leu Lys Arg Val Thr Leu Glu Leu Gly Gly
            275                280                285
Lys Ser Pro Asn Ile Ile Met Ser Asp Ala Asp Met Asp Trp Ala Val
            290                295                300
Glu Gln Ala His Phe Ala Leu Phe Phe Asn Gln Gly Gln Cys Cys Cys
305                310                315                320
Ala Gly Ser Arg Thr Phe Val Gln Glu Asp Ile Tyr Asp Glu Phe Val
            325                330                335
Glu Arg Ser Val Ala Arg Ala Lys Ser Arg Val Val Gly Asn Pro Phe
            340                345                350
Asp Ser Lys Thr Glu Gln Gly Pro Gln Val Asp Glu Thr Gln Phe Lys
            355                360                365
Lys Ile Leu Gly Tyr Ile Asn Thr Gly Lys Gln Glu Gly Ala Lys Leu
            370                375                380
Leu Cys Gly Gly Gly Ile Ala Ala Asp Arg Gly Tyr Phe Ile Gln Pro
385                390                395                400
Thr Val Phe Gly Asp Val Gln Asp Gly Met Thr Ile Ala Lys Glu Glu
            405                410                415
Ile Phe Gly Pro Val Met Gln Ile Leu Lys Phe Lys Thr Ile Glu Glu
            420                425                430
```

Val Val Gly Arg Ala Asn Asn Ser Thr Tyr Gly Leu Ala Ala Ala Val
        435                 440                 445

Phe Thr Lys Asp Leu Asp Lys Ala Asn Tyr Leu Ser Gln Ala Leu Gln
    450                 455                 460

Ala Gly Thr Val Trp Val Asn Cys Tyr Asp Val Phe Gly Ala Gln Ser
465                 470                 475                 480

Pro Phe Gly Gly Tyr Lys Met Ser Gly Ser Gly Arg Glu Leu Gly Glu
            485                 490                 495

Tyr Gly Leu Gln Ala Tyr Thr Lys Val Lys Thr Val Thr Val Lys Val
            500                 505                 510

Pro Gln Lys Asn Ser
        515